United States Patent
Nazaré et al.

(10) Patent No.: US 7,223,780 B2
(45) Date of Patent: May 29, 2007

(54) TRIAZOLE-DERIVATIVES AS BLOOD CLOTTING ENZYME FACTOR XA INHIBITORS

(75) Inventors: Marc Nazaré, Idstein (DE); Volker Laux, Mainz (DE); Armin Bauer, Sulzbach (DE); Michael Wagner, Alsbach (DE)

(73) Assignee: Sanofi-Aventis Deutschland GmbH, Frankfurt (DE)

( * ) Notice: Subject to any disclaimer, the term of this patent is extended or adjusted under 35 U.S.C. 154(b) by 99 days.

(21) Appl. No.: 10/848,916

(22) Filed: May 19, 2004

(65) Prior Publication Data

US 2005/0009827 A1  Jan. 13, 2005

Related U.S. Application Data

(60) Provisional application No. 60/507,112, filed on Sep. 30, 2003.

(30) Foreign Application Priority Data

May 19, 2003  (EP) .................. 03011309

(51) Int. Cl.
*A61K 31/4196* (2006.01)
*A61K 31/4025* (2006.01)
*A61K 31/44* (2006.01)
*A61K 31/42* (2006.01)
*C07D 207/00* (2006.01)
*C07D 249/08* (2006.01)
*C07D 213/00* (2006.01)

(52) U.S. Cl. .................. 514/383; 514/422; 514/326; 514/329; 514/444; 514/378; 514/360; 514/364; 514/381; 546/209; 546/210; 546/212; 546/224; 548/254.8; 548/266.6; 548/518; 548/247; 549/60; 549/81

(58) Field of Classification Search ........... 514/383, 514/422, 378, 444; 548/266.2, 264.8, 518, 548/266.6, 247; 549/81, 60
See application file for complete search history.

(56) References Cited

U.S. PATENT DOCUMENTS

| | | | |
|---|---|---|---|
| 5,525,733 A | 6/1996 | Novack et al. | |
| 5,998,424 A | 12/1999 | Galemmo, Jr. et al. | |
| 6,020,357 A | 2/2000 | Pinto et al. | |
| 6,339,099 B1 | 1/2002 | Lam et al. | |
| 6,906,084 B2 | 6/2005 | Nazaré et al. | |
| 6,953,857 B2 | 10/2005 | Nazaré et al. | |
| 7,067,665 B2 | 6/2006 | Nazaré et al. | |
| 2002/0091116 A1 | 7/2002 | Zhu et al. | |
| 2004/0106614 A1* | 6/2004 | Lange et al. | ................ 514/241 |
| 2004/0171604 A1 | 9/2004 | Nazaré et al. | |
| 2004/0204406 A1 | 10/2004 | Nazaré et al. | |
| 2004/0235824 A1 | 11/2004 | Nazaré et al. | |
| 2005/0009829 A1 | 1/2005 | Nazaré et al. | |
| 2005/0033049 A1 | 2/2005 | Nazaré et al. | |
| 2005/0043302 A1 | 2/2005 | Nazaré et al. | |

FOREIGN PATENT DOCUMENTS

| | | |
|---|---|---|
| EP | 0987274 | 3/2000 |
| WO | WO 92/06711 | 4/1992 |
| WO | WO 95/29189 | 11/1995 |
| WO | WO 96/12800 | 5/1996 |
| WO | WO 97/47651 | 12/1997 |
| WO | WO 99/32454 | 7/1999 |
| WO | WO 01/07436 | 2/2001 |
| WO | WO 01/32628 | 5/2001 |
| WO | WO 02/00651 | 1/2002 |

OTHER PUBLICATIONS

STN search results of Chemical Abstract of Indian Journal of Chemistry, Section B, 1976, 14B(10), 744-6, Harhash, et al.*
Farag et al. Chem. Research, 1994, p. 10-11.*
Adang, et al., A New Generation Of Orally Active Antithrombotics: Comparing Strategies in the GPIIb/IIIa, Thrombin and Factor Xa Areas, Drugs of the Future 2000, 25(4) 369-383.
Altural, et al., Preparation And Some Simple Reactions Of 1-Substituted Imidazole-2,4,5-Triones, Organic Preparation and Procedures Int., 23(2), 147-151 (1991).
Artico, et al., Aromatic hydrazides As Specific Inhibitors Of Bovine Serum Amine Oxidase, Eur. J. Med. Chem. Chim. Ther. (1992), 27, 219-228.
Bruche, et al., An Improved Synthesis of 1H-1,2,4-Triazoles from C-Triphenylphosphinimino-Hydrazones, Synthesis (1986) 9, 772-774.

(Continued)

*Primary Examiner*—Kamal A. Saeed
*Assistant Examiner*—Yong Chu
(74) *Attorney, Agent, or Firm*—Jiang Lin; Julie Anne Knight; Joseph D. Rossi

(57) ABSTRACT

The present invention is directed to the compound of formula I which is useful for inhibiting the activity of blood clotting enzyme Factor Xa. The present invention is also directed to compositions containing said compounds, processes for their preparation, their use, such as for inhibiting the formation of thrombin or for therapeutically treating a patient suffering from, or subject to, a disease state associated with a cardiovascular disorder.

9 Claims, No Drawings

OTHER PUBLICATIONS

Butler, et al., New General Methods For The Substitution Of 5-Chloropyrazoles. The Synthesis Of 1,3-Dialkyl-5-Chloropyrazol-4-yl Aryl Ketones And New 1,3-Dialkyl-2-Pyrazolin-5-Ones, J. Org. Chem. (1971) 36, 2542-2547.

Cerrada, et al., Synthesis Of p-Nitrophenylazoles By Phase Transfer Catalysis Without Solvent, Synthetic Communications, (1993), 23(14), 1947-1952.

Chan, et al., New N- And O-Arylations Wth Phenylboronic Acids And Cupric Acetate, Tetrahedron Letters 39 (1998) 2933-2936.

Cheng, et al., Relationship Between The Inhibition Constant (KI) And The Concentration Of Inhibitor Which Causes 50 Per Cent Inhibition (I50) Of An Enzymatic Reaction, Biochem. Pharmacol. 22 (1973) 3099-3108.

Collot, et al., First Combined Selective N-and C-Arylations With Boronic Acids: Application To The Synthesis Of 1,3-Diarylindazoles, Tetrahedron Letters 41 (2000) 9053-9057.

Cooper, et al., 1,4-Dihydropyridines As Antagonists Of Platelet Activating Factor. 1. Synthesis And Structure-Activity Relationships Of 2-(4-Heterocyclyl) Phenyl Derivatives, J. Med. Chem. (1992), 35, 3115-3129.

Cozzi, et al., Ethyl 2-{[5,6-Dihydro-7-(1H-Imidazol-1-YL)2-Naphthalenyl] Oxy}-2-Methylpropanoate As A New Potent Oxyisobutyrate Hypolipidaemic With Unusual Features, Farmaco (1987) 42, 205-218.

Danoun, et al., Etude De La Reactivite De Nitriles Vis-A-Vis Du Diazomethane: Synthese Et Etude Structurale De N-Methyl-V-Triazoles, Bull. Soc. Chim. Fr. (1995) 132, 943-951.

Duncia, et al., Three Synthetic Routes To A Sterically Hindered Tetrazole. A New One-Step Mild Conversion Of An Amide Into A Tetrazole, J. Org. Chem. (1991) 56, 2395-2400.

El-Ahl, et al., A Novel Approach For the Synthesis Of 5-Substituted Tetrazole Derivatives From Primary Amides In Mild One-Step Method, Tetrahedron Letters, vol. 38, No. 7, pp. 1257-1260. 1997.

Fleisher, et al., Improved Oral Drug Delivery: Solubility Limitations Overcome By The Use Of Prodrugs, Advanced Drug Delivery Reviews 19 (1996) 115-130.

Fusco, et al., Reaktionen Von Arylsulfonylaziden Mit Enaminen Aus Ketomethylenverbindungen, Chem. Ber. (1963) 96, 802-812.

Gardner et al., A Versatile Approach To Analogues Of The Cannabinoid-like Anti-emetic Nonabine (BRL 4664), J. Heterocycl. Chem. (1984), 21, 121-127.

Grimmett, et al., Synthesis And Reactions Of Lithiated Monocyclic Azoles Containing Two Or More Hetero-Atoms. Part III. Pyrazoles, Heterocycles (1994) 37, 2087-2147.

Hartwig, John, Ubergangsmetall-Katalysierte Synthese Von Arylaminen Und Arylethern Aus Arylhalogeniden Und—Triflaten: Anwendungen Und Reaktionsmechanismus, Angew. Chem. 110 (1998) 2154-2177.

Hartwig, et al., Room-Temperature Palladium-Catalyzed Amination Of Aryl Bromides And Chlorides And Extended Scope Of Aromatic C-N Bond Formation With A Commercial Ligand, J. Org. Chem. (1999), 64, 5575-5580.

Huisgen, et al., 1.3-Dipolare Additionen, II Synthese Von 1.2.4-Triazolen Aus Nitriliminen Und Nitrilen, Liebigs Ann. Chem. (1963) 653, 105.

Hans Bundgaard, Novel Chemical Approaches in Prodrug Design, Drugs Of The Future 1991, 16(5): 443-458.

Dehne, Heinz 1,2,3-Triazole, Methoden Der Organischen Chemie (Methods of Organic Chemistry), Georg Thieme Verlag, Stuttgart, Germany, 1994, vol. E8d Hetarene III, 305-405.

Kang, et al., Copper-Catalyzed N-Arylation Of Aryl Iodides With Benzamides Or Nitrogen Heterocycles In the Presence Of Ethylenediamine, Synlett (2002) 3, 427-430.

Klapars, et al., A General and Efficient Copper Catalyst For the Amidation Of Aryl Halides And The N-Arylation Of Nitrogen Heterocycles, J. Am. Chem. Soc. (2001), 123, 7727-7729.

Kwong, et al., Cooper-Catalyzed Coupling Of Alkylamines And Aryl Iodides: An Efficient System Even In An Air Atmosphere, Organic Letters (2002) vol. 4 (4) 581-584.

Lam, et al., Copper-Catalyzed General C-N And C-O Bond Cross-Coupling With Arylbornonic Acid, Tetrahedron Letters 42 (2001) 3415-3418.

Lam, et al., New Aryl/Heteroaryl C-N Bond Cross-Coupling Reactions Via Arylboronic Acid/Cupric Acetate Arylation, Tetrahedron Letters 39 (1998) 2941-2944.

Makino, et al., Selective Fluorination Of Ehtyl 1-Methylpyrazole-4-Carboxylates With Poly (Hydrogen Fluoride)—Amine Complex Under Electrolyic Anodic Oxidation, Journal Of Fluorine Chemistry, (1988), 39, 435-440.

Mann, et al., Palladium-Catalyzed C-N(sp2) Bond Formation: N-Arylation Of Aromatic And Unsaturated Nitrogen And The Reductive Elimination Chemistry Of Palladium Azolyl And Methyleneamido Complexes, J. Am. Chem. Soc. (1998), 120, 827-828.

Meier, et al., Tetrazole, Methoden Der Organischen Chemie (Methods of Organic Chemistry) Georg Thieme Verlag, Stuttgart, Germany 1994, vol. E8d Hetarene III, 664-794.

Murray-Rust, et al., An Expeditious Synthesis Of 4-Alkoxycarbonyl-5-Hydroxy-1,2,3-Triazoles: The Crystal And Molecular Structure Of The 2-Thienylammonium Salt Of 5-Hydroxy-4-Methoxycarbonyl-1-(2-thienyl)-1,2,3-Triazole, J. Chem. Soc. Perkin Trans. I (1984) 713-716.

Nachbaur, et al., 1,2,4-Triazole, Methoden der Organischen Chemie (Methods of Organic Chemistry), Georg Thieme Verlag, Stuttgart, Germany 1994, vol. E8d Hetarene III, 479-597.

Nichols, et al., 1-(2,5-Dimethoxy-4-(Trifluromethyl) Phenyl)-2-Aminopropane: A Potent Serotonin 5-HT2A/2C Agonist, J. Med Chem. (1994), 37, 4346-4351.

Old, et al., Efficient Palladium-Catalyzed N-Arylation Of Indoles, Organic Letters (2000) vol. 2, No. 10, 1403-1406.

Ostrem, et al., Discovery Of A Novel, Potent, And Specific Family Of Factor Xa Inhibitors Via Combinatorial Chemistry, Biochemistry (1998), 37, 1053-1059.

Pedersen, Christian, Rearrangement Of 4-Phenylazo-5-Hydroxy-1,2,3-Triazoles To Amides Of 2-Phenyl-5-Carboxytetrazole, Acta Chem. Scand. (1958) 12, 1236.

Qing, et al., First Synthesis Of Ortho-Trifluoromethylated Aryl Triflates, J. Chem. Soc. Perkin Trans I (1997) 3053-3057.

Sakamoto, et al., Palladium-Catalyzed Cyanation Of Aryl And Heteroaryl Iodides With Copper (I) Cyanide, J. Chem. Soc. Perkin Trans I (1999) 2323-2326.

Sauer, et al., Thermolyse Und Photolyse Von 3.4-Diphenyl-1.2.4-Oxidazolinon-(5) Und 2.4-Diphenyl-1.3.4-Oxidazolinon-5, Tetrahedron Letters (1968), No. 3, pp. 325-330.

Segel, Irwin, Behavior And Analysis Of Rapid Equilibrium And Steady-State Enzyme Systems, Enzyme Kinetics, (1975) John Wiley & Sons, New York, 100-125.

Sheehan, et al., Synthesis Of Phenyl-Substituted Triazole Analogs Of Histamine, J. Am. Chem. Soc. (1951) 73, 1207-1210.

Su, et al., Methyl Chlorodifluoroacetate A Convenient Trifluoromethylating Agent , Tetrahedron Letters, vol. 32, No. 52, 7689-7690, (1991).

Summers, et al., Structure Of 3-Alkyl-4-Arylazoisoxazol-5-ones And Related Compounds, J. Chem. Soc. (1965) 3312-3318.

Tamura, et al., One-Pot Synthesis Of Trifluroacetimidoyl Halides, J. Org. Chem. (1993) 58, 32-35.

Thomas, Edward. W., The Conversion Of Secondary Amides To Tetrazoles With Trifluoromethanesulfonic Anhydride And Sodium Azide, Synthesis (1993) 767.

Tokmakov, et al., Rearrangement Of 1-Arylindoles to 5H-Dibenz(b,f)azepines, Tetrahedron (1995), vol. 51, No. 7, pp. 2091-2098.

Umemoto, et al., Power and Structure-Variable Fluorinatiing Agents. The N-Flurorpyridinium Salt System, J. Am. Chem. Soc. (1990) 112, 8563-8575.

Unangst, et al., Synthesis Of Novel 1-Phenyl-1H-Indole-2-Carboxylic Acids. I. Utilization Of Ullmann And Dieckmann Reactions For The Preparation Of 3-Hydroxy, 3-Alkoxy, And 3-Alkyl Derivatives, J. Heterocycl. Chem. (1987) 24, 811.

Urata, et al., A Novel And Convenient Method For Trifluoromethylation Of Organic Halides Using CF3SiR3/KF/Cu(I) System, Tetrahedron Lett. (1991) 32 (1) 91-94.

Wang, et al., Practical Synthesis Of 1,3-Diaryl-5-Alkylpyrazoles By A Highly Regioselective N-Arylation Of 3,5-Disubstituted Pyrazoles With 4-Fluoronitrobenzene, Tetrahedron Letters 41 (2000) 5321-5324.

Wolfe, et al., Simple, Efficient Catalyst System For The Palladium-Catalyzed Amination Of Aryl Chlorides, Bromides, And Triflates, J. Org. Chem. 2000, 65, 1158-1174.

Yang, et al., Palladium-Catalyzed Amination of Aryl halides And Sulfonates, Journal of Organometallic Chemistry 576 (1999) 125-146.

Ykman, et al., Reactions Of Aryl Azides With Alpha-Keto Phosphorus Ylides, Tetrahedron (1971) 27, 845-849.

Cesar, et al., Use Of 3,5-Disubstituted 1,2,4-Triazoles For The Synthesis Of Peptidomimetics, Synthetic Communications, 30(22), 4147-4158 (2000).

U.S. Appl. No. 11/467,277, filed Aug. 25, 2006, Bauer et al.

U.S. Appl. No. 11/469,513, filed Sep. 01, 2006, Urmann et al.

* cited by examiner

TRIAZOLE-DERIVATIVES AS BLOOD CLOTTING ENZYME FACTOR XA INHIBITORS

This application claims the benefit of U.S. Provisional Application No. 60/507,112, filed Sep. 30, 2003,
This application claims the priority of EP Application No. 03011309.6, filed May 19, 2003.

FIELD OF THE INVENTION

The present invention relates to compounds of the formulae I and II,

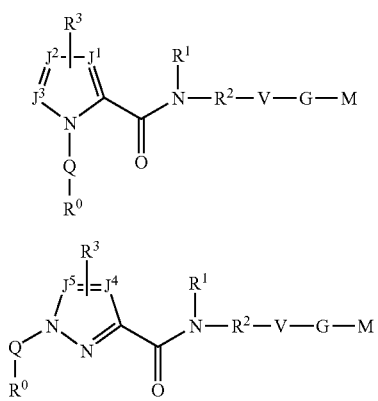

in which $R^0$; $R^1$; $R^2$; $R^3$; Q; $J^1$; $J^2$; $J^3$; $J^4$; $J^5$; V; G and M have the meanings indicated below. The compounds of the formulae I and II are valuable pharmacologically active compounds. They exhibit a strong anti-thrombotic effect and are suitable, for example, for the therapy and prophylaxis of cardio-vascular disorders like thromboembolic diseases or restenoses. They are reversible inhibitors of the blood clotting enzymes factor Xa (FXa) and/or factor VIIa (FVIIa), and can in general be applied in conditions in which an undesired activity of factor Xa and/or factor VIIa is present or for the cure or prevention of which an inhibition of factor Xa and/or factor VIIa is intended. The invention furthermore relates to processes for the preparation of compounds of the formulae I and II, their use, in particular as active ingredients in pharmaceuticals, and pharmaceutical preparations comprising them.

BACKGROUND OF THE INVENTION

Normal haemeostasis is the result of a complex balance between the processes of clot initiation, formation and clot dissolution. The complex interactions between blood cells, specific plasma proteins and the vascular surface, maintain the fluidity of blood unless injury and blood loss occurs (EP-A-987274). Many significant disease states are related to abnormal haemeostasis. For example, local thrombus formation due to rupture of atheroslerotic plaque is a major cause of acute myocardial infarction and unstable angina. Treatment of an occlusive coronary thrombus by either thrombolytic therapy or percutaneous angioplasty may be accompanied by acute thrombolytic reclosure of the affected vessel.

There continues to be a need for safe and effective therapeutic anticoagulants to limit or prevent thrombus formation. It is most desirable to develop agents that inhibit coagulation without directly inhibiting thrombin but by inhibiting other steps in the coagulation cascade like factor Xa and/or factor VIIa activity. It is now believed that inhibitors of factor Xa carry a lower bleeding risk than thrombin inhibitors (A. E. P. Adang & J. B. M. Rewinkel, Drugs of the Future 2000, 25, 369–383). Low molecular weight, factor Xa-specific blood clotting inhibitors that are effective but do not cause unwanted side effects have been described, for example, in WO-A-95/29189. However, besides being an effective factor Xa-specific blood clotting inhibitor, it is desirable that such inhibitors also have further advantageous properties, for instance stability in plasma and liver and selectivity versus other serine proteases whose inhibition is not intended, such as thrombin. There is an ongoing need for further low molecular weight factor Xa specific blood clotting inhibitors, which are effective and have the above advantages as well.

Specific inhibition of the factor VIIa/tissue factor catalytic complex using monoclonal antibodies (WO-A-92/06711) or a protein such as chloromethyl ketone inactivated factor VIIa (WO-A-96/12800, WO-A-97/47651) is an extremely effective means of controlling thrombus formation caused by acute arterial injury or the thrombotic complications related to bacterial septicemia. There is also experimental evidence suggesting that inhibition of factor VIIa/tissue factor activity inhibits restenosis following balloon angioplasty. Bleeding studies have been conducted in baboons and indicate that inhibition of the factor VIIa/tissue factor complex has the widest safety window with respect to therapeutic effectiveness and bleeding risk of any anticoagulant approach tested including thrombin, platelet and factor Xa inhibition. Certain inhibitors of factor VIIa have already been described. EP-A-987274, for example discloses compounds containing a tripeptide unit, which inhibit factor VIIa. However, the property profile of these compounds is still not ideal, and there is an ongoing need for further low molecular weight factor VIIa inhibitory blood clotting inhibitors The present invention satisfies the above needs by providing novel compounds of the formulae I and II, which exhibit better factor Xa and/or factor VIIa inhibitory activity and are favorable agents with high bioavailability.

SUMMARY OF THE INVENTION

Thus, the present invention relates to compounds of the formulae I and II,

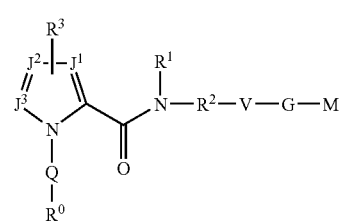

-continued

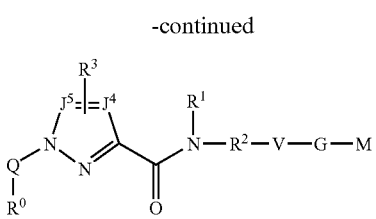

(II)

wherein $J^1$ is N or C, $J^2$ is N or C, $J^3$ is N or C, $J^4$ is N or C and $J^5$ is N or C,
provided that
a) $J^1$ is N and $J^2$ is N and $J^3$ is N, or
b) $J^1$ is N and $J^2$ is N and $J^3$ is C, or
c) $J^1$ is N and $J^2$ is C and $J^3$ is N, or
d) $J^1$ is C and $J^2$ is N and $J^3$ is N, or
e) $J^4$ is N and $J^5$ is N, or
f) $J^4$ is N and $J^5$ is C, or
g) $J^4$ is C and $J^5$ is N, and
$R^0$ is 1) a monocyclic or bicyclic 6- to 14-membered aryl, wherein aryl is mono-, di- or trisubstituted independently of one another by R8,
2) a monocyclic or bicyclic 4- to 15-membered heterocyclyl out of the group pyridyl, pyrimidinyl, indolyl, isoindolyl, indazolyl, phthalazinyl, quinolyl, isoquinolyl, benzothiophen, quinazolinyl and phenylpyridyl, wherein said heterocyclyl is unsubstituted or mono-, di- or trisubstituted independently of one another by R8, or
3) a monocyclic or bicyclic 4- to 15-membered heterocyclyl, containing one, two, three or four heteroatoms chosen from nitrogen, sulfur or oxygen,
wherein said heterocyclyl is unsubstituted or mono-, di- or trisubstituted independently of one another by R8, and which is additionally substituted by a monocyclic or bicyclic 4- to 15-membered heterocyclyl, containing one, two, three or four heteroatoms chosen from nitrogen, sulfur or oxygen,
wherein heterocyclyl is unsubstituted or mono-, di- or trisubstituted independently of one another by R8,
R8 is 1) halogen,
2) —$NO_2$,
3) —CN,
4) —C(O)—$NH_2$,
5) —OH,
6) —$NH_2$,
7) —O—$CF_3$,
8) a monocyclic or bicyclic 6- to 14-membered aryl, wherein aryl is mono-, di- or trisubstituted independently of one another by halogen or —O—($C_1$–$C_8$)-alkyl,
9) —($C_1$–$C_8$)-alkyl, wherein alkyl is unsubstituted or mono-, di- or trisubstituted independently of one another by halogen, $NH_2$, —OH or a methoxy residue,
10) —O—($C_1$–$C_8$)-alkyl, wherein alkyl is unsubstituted or mono-, di- or trisubstituted independently of one another by halogen, $NH_2$, —OH or a methoxy residue,
11) —$SO_2$—$CH_3$ or
12) —$SO_2$—$CF_3$,
provided that R8 is at least one halogen, —C(O)—$NH_2$ or —O—($C_1$–$C_8$)-alkyl residue, if $R^0$ is a monocyclic or bicyclic 6- to 14-membered aryl,
Q is a direct bond, —($C_0$–$C_2$)-alkylene-C(O)—$NR^{10}$—, —$NR^{10}$—C(O)—$NR^{10}$—, —$NR^{10}$—C(O)—, —$SO_2$—, —($C_1$–$C_6$)-alkylene, —$(CH_2)_m$—$NR^{10}$—C(O)—$NR^{10}$—$(CH_2)_n$—, —$(CH_2)_m$—$NR^{10}$—C(O)—$(CH_2)_n$—, —$(CH_2)_m$—S—$(CH_2)_n$—, —$(CH_2)_m$—C(O)—$(CH_2)_n$—, —$(CH_2)_m$—$SO_2$—$NR^{10}$—$(CH_2)_n$—, —$(CH_2)_m$—$NR^{10}$—$SO_2$—$(CH_2)_n$—, —$(CH_2)_m$—$NR^{10}$—$SO_2$—$NR^{10}$—$(CH_2)_n$—, —$(CH_2)_m$—CH(OH)—$(CH_2)_n$—, —$(CH_2)_m$—O—C(O)—$NR^{10}$—$(CH_2)_n$—, —($C_2$–$C_3$)-alkylene-O—($C_0$–$C_3$)-alkylene-, —($C_2$–$C_3$)-alkylene-S(O)—, —($C_2$–$C_3$)-alkylene-S(O)$_2$—, —$(CH_2)_m$—$NR^{10}$—C(O)—O—$(CH_2)_n$—, —($C_2$–$C_3$)-alkylene-S(O)$_2$—NH—($R^{10}$)—, —($C_2$–$C_3$)-alkylene-N($R^{10}$)— or
—($C_0$–$C_3$)-alkylene-C(O)—O—$(CH_2)_m$—,
wherein $R^{10}$ is as defined below, and wherein n and m are independently of one another identical or different and are the integers zero, 1, 2, 3, 4, 5 or 6, wherein the alkylene residues which are formed by —$(CH_2)_m$— or —$(CH_2)_n$— are unsubstituted or mono-, di- or trisubstituted independently of one another by halogen, —$NH_2$ or —OH; or
—$C_3$–$C_6$)-cycloalkylen, wherein cycloalkylen is unsubstituted or mono-, di- or trisubstituted independently of one another by halogen, —$NH_2$ or —OH;
$R^1$ is a hydrogen atom, —($C_1$–$C_4$)-alkyl, wherein alkyl is unsubstituted or substituted one to three times by R13; —($C_1$–$C_3$)-alkylene-C(O)—NH—$R^0$, —($C_1$–$C_3$)-alkylene-C(O)—O—$R^{15}$, a monocyclic or bicyclic 6- to 14-membered aryl, wherein aryl is mono-, di- or trisubstituted independently of one another by R8, wherein R8 is as defined above; a monocyclic or bicyclic 4- to 15-membered heterocyclyl, containing one, two, three or four heteroatoms chosen from nitrogen, sulfur or oxygen; —($C_1$–$C_3$)-perfluoroalkylene, —($C_1$–$C_3$)-alkylene-S(O)—($C_1$–$C_4$)-alkyl, —($C_1$–$C_3$)-alkylene-S(O)$_2$—($C_1$–$C_3$)-alkyl, —($C_1$–$C_3$)-alkylene-S(O)$_2$—N($R^{4'}$)—$R^{5'}$, —($C_1$–$C_3$)-alkylene-O—($C_1$–$C_4$)-alkyl, —($C_0$–$C_3$)-alkylene-($C_3$–$C_8$)-cycloalkyl, or —($C_0$–$C_3$)-alkylene-het, wherein het is a 3- to 7-membered cyclic residue, containing up to 1, 2, 3 or 4 heteroatoms chosen from nitrogen, sulfur or oxygen, wherein said cyclic residue is unsubstituted or mono-, di- or trisubstituted independently of one another by R14,
$R^{4'}$ and $R^{5'}$ are independent of one another are identical or different and are hydrogen atom or —($C_1$–$C_4$)-alkyl,
$R^2$ is a direct bond or —($C_1$–$C_4$)-alkylene, or
$R^1$ and $R^3$ together with the atoms to which they are bonded can form a 6- to 8-membered cyclic group, containing 1, 2, 3 or 4 heteroatoms chosen from nitrogen, sulfur or oxygen, wherein said cyclic group is unsubstituted or mono-, di- or trisubstituted independently of one another by R14, or
$R^1$—N—$R^2$—V can form a 4- to 8-membered cyclic group, containing 1, 2, 3 or 4 heteroatoms chosen from nitrogen, sulfur or oxygen, wherein said cyclic group is unsubstituted or mono-, di- or trisubstituted independently of one another by R14,
R14 is halogen, —OH, =O, —($C_1$–$C_8$)-alkyl, —($C_1$–$C_4$)-alkoxy, —$NO_2$, —C(O)—OH, —CN, —$NH_2$, —C(O)—O—($C_1$–$C_4$)-alkyl, —($C_0$–$C_8$)-alkyl-$SO_2$—($C_1$–$C_4$)-alkyl, —($C_0$–$C_8$)-alkyl-$SO_2$—($C_1$–$C_3$)-perfluoroalkyl, —($C_0$–$C_8$)-alkyl-$SO_2$—N($R^{18}$)—$R^{21}$, —C(O)—NH—($C_1$–$C_8$)-alkyl, —C(O)—N—[($C_1$–$C_8$)-alkyl]$_2$, —$NR^{18}$—C(O)—NH—($C_1$–$C_8$)-alkyl, —C(O)—$NH_2$, —S—$R^{18}$, or —$NR^{18}$—C(O)—NH—[($C_1$–$C_8$)-alkyl]$_2$,
wherein $R^{18}$ and $R^{21}$ are independently from each other hydrogen atom, —($C_1$–$C_3$)-perfluoroalkyl or —($C_1$–$C_6$)-alkyl, V is 1) a 3- to 7-membered cyclic residue, containing 1, 2, 3 or 4 heteroatoms chosen from nitrogen, sulfur or oxygen, wherein said cyclic residue is unsubstituted or mono-, di- or trisubstituted independently of one another by R14,
2) a 6- to 14-membered aryl, wherein aryl is unsubstituted or mono-, di- or trisubstituted independently of one another by R14, or
3) a monocyclic or bicyclic 4- to 15-membered heterocyclyl, wherein said heterocyclyl is unsubstituted or mono-, di- or trisubstituted independently of one another by R14, G is a direct bond, $-(CH_2)_m-NR^{10}-SO_2-NR^{10}-(CH_2)_n-$, $-(CH_2)_m-CH(OH)-(CH_2)_n-$, $-(CH_2)_m-$, $-(CH_2)_m-O-(CH_2)_n-$, $-(CH_2)_m-C(O)-NR^{10}-(CH_2)_n-$, $-(CH_2)-SO_2-(CH_2)_n-$, $-(CH_2)_m-NR^{10}-C(O)-NR^{10}-(CH_2)_n-$, $-(CH_2)_m-NR^{10}-C(O)-(CH_2)_n-$, $-(CH_2)_m-C(O)-(CH_2)_n-$, $-(CH_2)-S-(CH_2)_n-$, $-(CH_2)_m-SO_2-NR^{10}-(CH_2)_n-$, $-(CH_2)_m-NR^{10}-SO_2-(CH_2)_n-$, $-(CH_2)_m-NR^{10}-$, $-(CH_2)_m-O-C(O)-NR^{10}-(CH_2)_n-$ or $-(CH_2)_m-NR^{10}-C(O)-O-(CH_2)_n-$, n and m are independently of one another identical or different and are the integers zero, 1, 2, 3, 4, 5 or 6, M is 1) a hydrogen atom,
2) $-(C_1-C_8)$-alkyl, wherein alkyl is unsubstituted or mono-, di- or trisubstituted independently of one another by R14,
3) $-C(O)-N(R11)-R12$,
4) $-(CH_2)_m-NR^{10}$,
5) a 6- to 14-membered aryl, wherein aryl is unsubstituted or mono-, di- or trisubstituted independently of one another by R14,
6) a monocyclic or bicyclic 4- to 15-membered heterocyclyl, wherein heterocyclyl is unsubstituted or mono-, di- or trisubstituted independently of one another by R14,
7) $-(C_3-C_8)$-cycloalkyl, wherein said cycloalkyl is unsubstituted or mono-, di- or trisubstituted independently of one another by R14, or
8) a 3- to 7-membered cyclic residue, containing 1, 2, 3 or 4 heteroatoms chosen from nitrogen, sulfur or oxygen, wherein said cyclic residue is unsubstituted or mono-, di- or trisubstituted independently of one another by R14, wherein R14 is defined above, R³ is
1) hydrogen atom,
2) halogen,
3) $-(C_1-C_4)$-alkyl, wherein alkyl is unsubstituted or mono-, di- or trisubstituted independently of one another by R13,
4) $-(C_1-C_3)$-perfluoroalkyl,
5) phenyl, wherein phenyl is unsubstituted or mono-, di- or trisubstituted independently of one another by R13,
6) $-(C_0-C_4)$-alkylene-O-R19, wherein R19 is
  a) hydrogen atom,
  b) $-(C_1-C_4)$-alkyl, wherein alkyl is unsubstituted or mono-, di- or trisubstituted independently of one another by R13,
  c) phenyl, wherein phenyl is unsubstituted or mono-, di- or trisubstituted independently of one another by R13,
  d) $-CF_3$ or
  e) $-CHF_2$,
7) $-NO_2$,
8) $-CN$,
9) $-SO_s-R^{11}$, wherein s is 1 or 2,
10) $-SO_t-N(R^{11})-R^{12}$, wherein t is 1 or 2,
11) $-(C_0-C_4)$-alkylene-C(O)-R^{11},
12) $-(C_0-C_4)$-alkylene-C(O)-O-R^{11},
13) $-(C_0-C_4)$-alkylene-C(O)-N(R^{11})-R^{12},
14) $-(C_0-C_4)$-alkylene-N(R^{11})-R^{12},
15) $-NR^{10}-SO_2-R^{10}$,
16) $-S-R^{10}$,
17) $-(C_0-C_2)$alkylene-C(O)-O-(C_2-C_4)$-alkylene-O-C(O)-(C_1-C_4)$-alkyl,
18) $-C(O)-O-C(R15, R16)-O-C(O)-R17$,
19) $-(C_0-C_2)$alkylene-C(O)-O-(C_2-C_4)$-alkylene-O-C(O)-O-(C_1-C_6)$-alkyl,
20) $-C(O)-O-C(R15, R16)-O-C(O)-O-R17$,
21) $-(C_0-C_4)$-alkylene-$(C_6-C_{14})$-aryl, wherein aryl is mono-, di- or trisubstituted independently of one another by R13,
22) $-(C_0-C_4)$-alkylene-$(C_4-C_{15})$-heterocyclyl, wherein heterocyclyl is unsubstituted or mono-, di- or trisubstituted independently of one another by R13
23) $-(C_0-C_4)$-alkylene-$(C_3-C_8)$-cycloalkyl, wherein cycloalkyl is unsubstituted or mono-, di- or trisubstituted independently of one another by R13,
24) $-(C_0-C_4)$-alkylene-het, wherein het is unsubstituted or mono-, di- or trisubstituted independently of one another by R13,
25) $-(C_0-C_4)$-alkylene-O-$CH_2$-$(C_1-C_3)$-perfluoroalkylene-$CH_2$-O-$(C_0-C_4)$-alkyl,
26) $-SO_w-N(R^{11})-R^{13}$, wherein w is 1 or 2,
27) $-(C_0-C_4)$-alkylene-C(O)-N(R^{11})-R^{13},
28) $-(C_0-C_4)$-alkylene-N(R^{11})-R^{13},
29) =O or
30) a residue from the following list

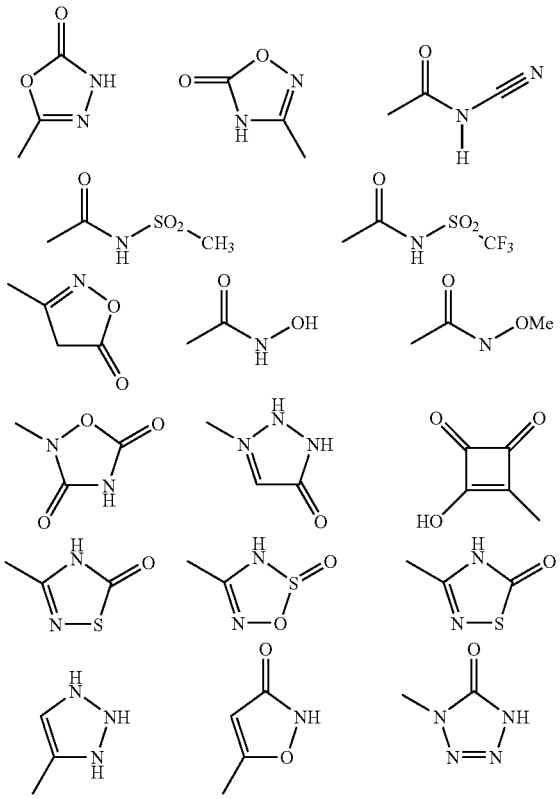

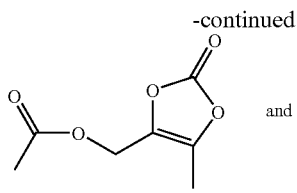 and 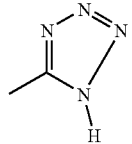

wherein Me is methyl, or if two —OR19 residues are attached to adjacent atoms they can form together with the atoms which they are attached to a 5- or 6-membered ring, which is unsubstituted or substituted one, two, three or four times by R13, provided that $R^3$ can be attached at any position on the ring of formulae I and II and can occur one, two or three times and is independently of one another identical or different, R11 and R12 are independently of one another identical or different and are
1) hydrogen atom,
2) —($C_1$–$C_6$)-alkyl, wherein alkyl is unsubstituted or mono-, di- or trisubstituted independently of one another by R13,
3) —($C_0$–$C_6$)-alkyl-($C_3$–$C_8$)-cycloalkyl,
4) —$SO_t$—$R^{10}$, wherein t is 1 or 2,
5) —($C_0$–$C_6$)-alkyl-($C_6$–$C_{14}$)-aryl, wherein alkyl and aryl independently from one another are unsubstituted or mono-, di- or trisubstituted by R13,
6) —($C_1$–$C_3$)-perfluoroalkyl,
7) —O—$R^{17}$, or
8) —($C_0$–$C_6$)-alkyl-($C_4$–$C_{15}$)-heterocyclyl, wherein alkyl and heterocyclyl independently from one another are unsubstituted or mono-, di- or trisubstituted by R13, or R11 and R12 together with the nitrogen atom to which they are bonded can form a 4- to 8-membered monocyclic heterocyclic ring which in addition to the nitrogen atom can contain one or two identical or different ring heteroatoms chosen from oxygen, sulfur and nitrogen; wherein said heterocyclic ring is unsubstituted or mono-, di- or trisubstituted independently of one another by R13, R13 is halogen, —$NO_2$, —CN, =O, —OH, —$CF_3$, —C(O)—O—$R^{10}$, —C(O)—N($R^{10}$)—$R^{20}$, —N($R^{10}$)—$R^{20}$,
—($C_3$–$C_8$)-cycloalkyl, —($C_0$–$C_3$)-alkylene-O—$R^{10}$, —Si—($CH_3$)$_3$, —N($R^{10}$)—S(O)$_u$—$R^{10}$, wherein u is 1 or 2, —S—$R^{10}$, —$SO_r$—$R^{10}$, wherein r is 1 or 2, —S(O)$_v$—N($R^{10}$)—$R^{20}$, wherein v is 1 or 2, —C(O)—$R^{10}$, —($C_1$–$C_8$)-alkyl, —($C_1$–$C_8$)-alkoxy, phenyl, phenyloxy-, —O—$CF_3$, —($C_0$–$C_4$)-alkyl-C(O)—O—C(R15, R16)—O—C(O)—R17, —($C_1$–$C_4$)-alkoxy-phenyl, —($C_0$–$C_4$)-alkyl-C(O)—O—C(R15, R16)—O—C(O)—O—R17, —($C_1$–$C_3$)-perfluoroalkyl, —O—R15, —NH—C(O)—NH—$R^{10}$, —NH—C(O)—O—$R^{10}$, or a residue from the following list

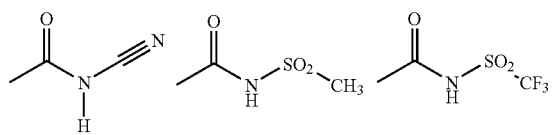

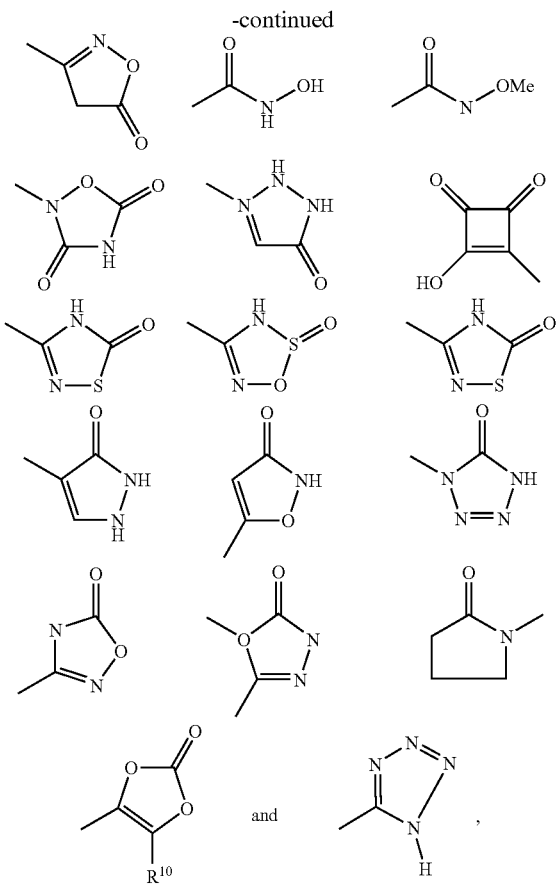

$R^{10}$ and $R^{20}$ are independently of one another hydrogen, —($C_1$–$C_6$)-alkyl, —($C_0$–$C_4$)-alkyl-OH, —($C_0$–$C_4$)-alkyl-O—($C_1$–$C_4$)-akyl or —($C_1$–$C_3$)-perfluoroalkyl, R15 and R16 are independently of one another hydrogen, —($C_1$–$C_6$)-alkyl, or together with the carbon atom to which they are bonded they can form a 3- to 6 membered carbocyclic ring which is unsubstituted or substituted one to three times by $R^{10}$, and R17 is —($C_1$–$C_6$)-alkyl —($C_1$–$C_6$)-alkyl-OH, —($C_1$–$C_6$)-alkyl-O—($C_1$–$C_6$)-alkyl, —($C_3$–$C_8$)-cycloalkyl, —($C_1$–$C_6$)-alkyl-O—($C_1$–$C_8$)-alkyl-($C_3$–$C_8$)-cycloalkyl, —($C_1$–$C_6$)-alkyl-($C_3$–$C_8$)-cycloalkyl, wherein said cycloalkyl ring is unsubstituted or substituted one, two or three times by —OH, —O—($C_1$–$C_4$)-alkyl or $R^{10}$, in all its stereoisomeric forms and mixtures thereof in any ratio, and its physiologically tolerable salts.

2) The present invention also relates to compounds of the formulae I and II, wherein $J^1$ is N or C, $J^2$ is N or C, $J^3$ is N or C, $J^4$ is N or C and $J^5$ is N or C, provided that
a) $J^1$ is N and $J^2$ is N and $J^3$ is N, or
b) $J^1$ is N and $J^2$ is N and $J^3$ is C, or
c) $J^1$ is N and $J^2$ is C and $J^3$ is N, or
d) $J^1$ is C and $J^2$ is N and $J^3$ is N, or
e) $J^4$ is N and $J^5$ is N, or
f) $J^4$ is N and $J^5$ is C, or
g) $J^4$ is C and $J^5$ is N, and $R^0$ is 1) a monocyclic or bicyclic 6- to 14-membered aryl, wherein aryl is mono-, di- or trisubstituted independently of one another by R8, 2) a monocyclic or bicyclic 4- to 15-membered heterocyclyl out of the group benzothiophen, indazolyl, indolyl, isoindolyl, isoquinolyl, phenylpyridyl, phthalazinyl, pyridyl, pyridyl, pyrimidinyl, quinazolinyl and quinolyl, wherein said heterocyclyl is unsubstituted or mono-, di- or trisubstituted independently of one another by R8, or 3) a monocyclic or bicyclic 4- to 15-membered heterocyclyl, containing one, two, three or four heteroatoms chosen from nitrogen, sulfur or oxygen, wherein said heterocyclyl is unsubstituted or mono-, di- or trisubstituted independently of one another by R8, and which is additionally substituted by a monocyclic or bicyclic 4- to 15-membered heterocyclyl, containing one, two, three or four heteroatoms chosen from nitrogen, sulfur or oxygen, wherein heterocyclyl is unsubstituted or mono-, di- or trisubstituted independently of one another by R8, R8 is 1) halogen,
2) —$NO_2$,
3) —CN,
4) —C(O)—$NH_2$,
5) —OH,
6) —$NH_2$,
7) —O—$CF_3$
8) a monocyclic or bicyclic 6- to 14-membered aryl, wherein aryl is mono-, di- or trisubstituted independently of one another by halogen or —O—($C_1$–$C_8$)-alkyl,
9) —($C_1$–$C_8$)-alkyl, wherein alkyl is unsubstituted or mono-, di- or trisubstituted independently of one another by halogen, $NH_2$, —OH or a methoxy residue, or
10) —O—($C_1$–$C_8$)-alkyl, wherein alkyl is unsubstituted or mono-, di- or trisubstituted independently of one another by halogen, $NH_2$, —OH or a methoxy residue,
11) —$SO_2$—$CH_3$ or
12) —$SO_2$—$CF_3$,
provided that R8 is at least one halogen, —C(O)—$NH_2$ or —O—($C_1$–$C_8$)-alkyl residue, if $R^0$ is a monocyclic or bicyclic 6- to 14-membered aryl, Q is a direct bond, —($C_0$–$C_2$)-alkylene-C(O)—$NR^{10}$—, —$NR^{10}$—C(O)—$NR^{10}$—, —$NR^{10}$—C(O)—, —$SO_2$—, —($C_1$–$C_6$)-alkylene, —$(CH_2)_m$—$NR^{10}$—C(O)—$NR^{10}$—$(CH_2)_n$—, —$(CH_2)_m$—$NR^{10}$—C(O)—$(CH_2)_n$—, —$(CH_2)_m$—S—$(CH_2)_n$—, —$(CH_2)_m$—C(O)—$(CH_2)_n$—, —$(CH_2)_m$—$SO_2$—$NR^{10}$—$(CH_2)_n$—, —$(CH_2)_m$—$NR^{10}$—$SO_2$—$(CH_2)_n$—, —$(CH_2)_m$—$NR^{10}$—$SO_2$—$NR^{10}$—$(CH_2)_n$—, —$(CH_2)_m$—CH(OH)—$(CH_2)_n$—, —$(CH_2)_m$—O—C(O)—$NR^{10}$—$(CH_2)_n$—, —($C_2$–$C_3$)-alkylene-O—($C_0$–$C_3$)-alkylene-, —($C_2$–$C_3$)-alkylene-S(O)—, —($C_2$–$C_3$)-alkylene-$S(O)_2$—, —$(CH_2)_m$—$NR^{10}$—C(O)—O—$(CH_2)_n$—, —($C_2$–$C_3$)-alkylene-$S(O)_2$—NH—($R^{10}$)—, —($C_2$–$C_3$)-alkylene-N($R^{10}$)— or
—($C_0$–$C_3$)-alkylene-C(O)—O—$(CH_2)_m$—, wherein $R^{10}$ is as defined below, and wherein n and m are independently of one another identical or different and are the integers zero, 1, 2, 3, 4, 5 or 6, wherein the alkylene residues which are formed by —$(CH_2)_m$— or —$(CH_2)_n$— are unsubstituted or mono-, di- or trisubstituted independently of one another by halogen, —$NH_2$ or —OH; or —$C_3$–$C_6$)-cycloalkylen, wherein cycloalkylen is unsubstituted or mono-, di- or trisubstituted independently of one another by halogen, —$NH_2$ or —OH;

$R^1$ is a hydrogen atom, —($C_1$–$C_4$)-alkyl, wherein alkyl is unsubstituted or substituted one to three times by R13;

—($C_1$–$C_3$)-alkylene-C(O)—NH—$R^0$, —($C_1$–$C_3$)-alkylene-C(O)—O—R15, a monocyclic or bicyclic 6- to 14-membered aryl, wherein aryl is mono-, di- or trisubstituted independently of one another by R8, wherein R8 is as defined above; a monocyclic or bicyclic 4- to 15-membered heterocyclyl, containing one, two, three or four heteroatoms chosen from nitrogen, sulfur or oxygen;
—($C_1$–$C_3$)-perfluoroalkylene,
—($C_1$–$C_3$)-alkylene-S(O)—($C_1$–$C_4$)-alkyl, —($C_1$–$C_3$)-alkylene-$S(O)_2$—($C_1$–$C_3$)-alkyl,
—($C_1$–$C_3$)-alkylene-$S(O)_2$—N($R^{4'}$)—$R^{5'}$, —($C_1$–$C_3$)-alkylene-O—($C_1$–$C_4$)-alkyl,
—($C_0$–$C_3$)-alkylene-($C_3$–$C_8$)-cycloalkyl, or —($C_0$–$C_3$)-alkylene-het, wherein het is unsubstituted or mono-, di- or trisubstituted independently of one another by R14,
$R^{4'}$ and $R^{5'}$ are independent of one another are identical or different and are hydrogen atom or —($C_1$–$C_4$)-alkyl,
$R^2$ is a direct bond or —($C_1$–$C_4$)-alkylene, or
$R^1$ and R3 together with the atoms to which they are bonded can form a 6- to 8-membered cyclic group, containing up to 1, 2, 3 or 4 heteroatoms chosen from nitrogen, sulfur or oxygen, wherein said cyclic group is unsubstituted or mono-, di- or trisubstituted independently of one another by R14, or
$R^1$—N—$R^2$—V can form a 4- to 8-membered cyclic group, containing 1, 2, 3 or 4 heteroatoms chosen from nitrogen, sulfur or oxygen, wherein said cyclic group is unsubstituted or mono-, di- or trisubstituted independently of one another by R14, R14 is halogen, —OH, =O, —($C_1$–$C_8$)-alkyl, —($C_1$–$C_4$)-alkoxy, —$NO_2$, —C(O)—OH, —CN, —$NH_2$, —C(O)—O—($C_1$–$C_4$)-alkyl, —($C_0$–$C_8$)-alkyl-$SO_2$—($C_1$–$C_4$)-alkyl, —($C_0$–$C_8$)-alkyl-$SO_2$—($C_1$–$C_3$)-perfluoroalkyl, —($C_0$–$C_8$)-alkyl-$SO_2$—N($R^{18}$)—$R^{21}$, —C(O)—NH—($C_1$–$C_8$)-alkyl, —C(O)—N—[($C_1$–$C_8$)-alkyl]$_2$, —$NR^{18}$—C(O)—NH—($C_1$–$C_8$)-alkyl, —C(O)—$NH_2$, —S—$R^{18}$, or —$NR^{18}$—C(O)—NH—[($C_1$–$C_8$)-alkyl]$_2$, wherein $R^{18}$ and $R^{21}$ are independently from each other hydrogen atom, —($C_1$–$C_3$)-perfluoroalkyl or $C_1$–$C_6$)-alkyl, V is 1) a 3- to 7-membered cyclic residue, containing 1, 2, 3 or 4 heteroatoms chosen from nitrogen, sulfur or oxygen, wherein said cyclic residue is unsubstituted or mono-, di- or trisubstituted independently of one another by R14,
2) a 6- to 14-membered aryl, wherein aryl is unsubstituted or mono-, di- or trisubstituted independently of one another by R14, or
3) a monocyclic or bicyclic 4- to 15-membered heterocyclyl, wherein said heterocyclyl is unsubstituted or mono-, di- or trisubstituted independently of one another by R14, G is a direct bond, —$(CH_2)_m$—$NR^{10}$—$SO_2$—$NR^{10}$—$(CH_2)_n$—, —$(CH_2)_m$—CH(OH)—$(CH_2)_n$—, —$(CH_2)_m$—, —$(CH_2)_m$—O—$(CH_2)_n$—, —$(CH_2)_m$—C(O)—$NR^{10}$—$(CH_2)_n$—, —$(CH_2)$—$SO_2$—$(CH_2)_n$—, —$(CH_2)_m$—$NR^{10}$—C(O)—$NR^{10}$—$(CH_2)_n$—, —$(CH_2)_m$—$NR^{10}$—C(O)—$(CH_2)_n$—, —$(CH_2)_m$—C(O)—$(CH_2)_n$—, —$(CH_2)$—S—$(CH_2)_n$—, —$(CH_2)_m$—$SO_2$—$NR^{10}$—$(CH_2)_n$—, —$(CH_2)_m$—$NR^{10}$—$SO_2$—$(CH_2)_n$—, —$(CH_2)_m$—$NR^{10}$—, —$(CH_2)_m$—O—C(O)—$NR^{10}$—$(CH_2)_n$— or $CH_2)_m$—$NR^{10}$—C(O)—O—$(CH_2)_n$—, n and m are independently of one another identical or different and are the integers zero, 1, 2, 3, 4, 5 or 6, M is 1) a hydrogen atom, 2) —($C_1$–$C_8$)-alkyl, wherein alkyl is unsubstituted or mono-, di- or trisubstituted independently of one another by R14,
3) —C(O)—N(R11)—R12,
4) —($CH_2$)$_m$—$NR^{10}$,
5) —($C_6$–$C_{14}$)-aryl, wherein aryl is unsubstituted or mono-, di- or trisubstituted independently of one another by R14,
6) —($C_4$–$C_{15}$)-heterocyclyl, wherein heterocyclyl is unsubstituted or mono-, di- or trisubstituted independently of one another by R14,
7) —($C_3$–$C_8$)-cycloalkyl, wherein said cycloalkyl is unsubstituted or mono-, di- or trisubstituted independently of one another by R14, or
8) a 3- to 7-membered cyclic residue, containing up to 1, 2, 3 or 4 heteroatoms chosen from nitrogen, sulfur or oxygen, wherein said cyclic residue is unsubstituted or mono-, di- or trisubstituted independently of one another by R14, wherein R14 is defined above, $R^3$ is 1) hydrogen atom,
2) halogen,
3) —($C_1$–$C_4$)-alkyl, wherein alkyl is unsubstituted or mono-, di- or trisubstituted independently of one another by R13,
4) —($C_1$–$C_3$)-perfluoroalkyl,
5) phenyl, wherein phenyl is unsubstituted or mono-, di- or trisubstituted independently of one another by R13,
6) —($C_0$–$C_4$)-alkylene-O—R19, wherein R19 is
   a) hydrogen atom,
   b) —($C_1$–$C_4$)-alkyl, wherein alkyl is unsubstituted or mono-, di- or trisubstituted independently of one another by R13,
   c) phenyl, wherein phenyl is unsubstituted or mono-, di- or trisubstituted independently of one another by R13,
   d) —$CF_3$ or
   e) —$CHF_2$,
7) —$NO_2$,
8) —CN,
9) —$SO_s$—$R^{11}$, wherein s is 1 or 2,
10) —$SO_t$—N($R^{11}$)—$R^{12}$, wherein t is 1 or 2,
11) —($C_0$–$C_4$)-alkylene-C(O)—$R^{11}$,
12) —($C_0$–$C_4$)-alkylene-C(O)—O—$R^{11}$,
13) —($C_0$–$C_4$)-alkylene-C(O)—N($R^{11}$)—$R^{12}$,
14) —($C_0$–$C_4$)-alkylene-N($R^{11}$)—$R^{12}$,
15) —$NR^{10}$—$SO_2$—$R^{10}$,
16) —S—$R^{10}$,
17) —($C_0$–$C_2$)alkylene-C(O)—O—($C_2$–$C_4$)-alkylene-O—C(O)—($C_1$–$C_4$)-alkyl,
18) —C(O)—O—C(R15, R16)—O—C(O)—R17,
19) $C_0$–$C_2$)alkylene-C(O)—O—($C_2$–$C_4$)-alkylene-O—C(O)—O—($C_1$–$C_6$)-alkyl,
20) —C(O)—O—C(R15, R16)—O—C(O)—O—R17,
21) —($C_0$–$C_4$)-alkylene-($C_6$–$C_{14}$)-aryl, wherein aryl is mono-, di- or trisubstituted independently of one another by R13,
22) —($C_0$–$C_4$)-alkylene-($C_4$–$C_{15}$)-heterocyclyl, wherein heterocyclyl is unsubstituted or mono-, di- or trisubstituted independently of one another by R13
23) —($C_0$–$C_4$)-alkylene-($C_3$–$C_8$)-cycloalkyl, wherein cycloalkyl is unsubstituted or mono-, di- or trisubstituted independently of one another by R13,
24) —($C_0$–$C_4$)-alkylene-het, wherein het is unsubstituted or mono-, di- or trisubstituted independently of one another by R13,
25) —($C_0$–$C_3$)-alkylene-O—$CH_2$—($C_1$–$C_3$)-perfluoroalkylene-$CH_2$—O—($C_0$–$C_3$)-alkyl,
26) —$SO_w$—N($R^{11}$)—$R^{13}$, wherein w is 1 or 2,
27) —($C_0$–$C_4$)-alkylene-C(O)—N($R^{11}$)—$R^{13}$,
28) —($C_0$–$C_4$)-alkylene-N($R^{11}$)—$R^{13}$, or
29) a residue from the following list

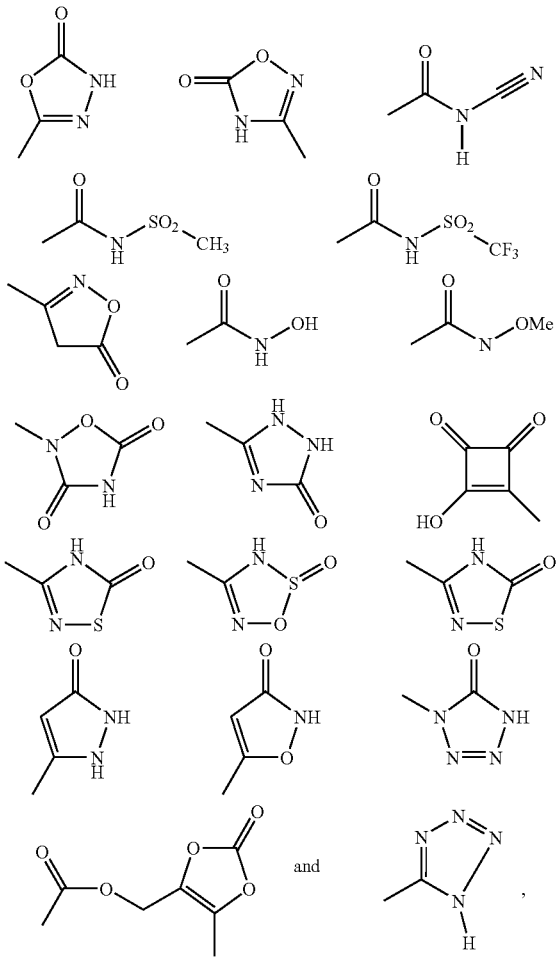

wherein Me is methyl, or if two —OR19 residues are attached to adjacent atoms they can form together with the atoms which they are attached to a 5- or 6-membered ring, which is unsubstituted or substituted one, two, three or four times by R13, provided that $R^3$ can be attached at any position on the ring of formulae I and II and can occur one, two or three times and is independently of one another identical or different, R11 and R12 are independently of one another identical or different and are
1) hydrogen atom,
2) —($C_1$–$C_6$)-alkyl, wherein alkyl is unsubstituted or mono-, di- or trisubstituted independently of one another by R13,
3) —($C_0$–$C_6$)-alkyl-($C_3$–$C_8$)-cycloalkyl,
4) —$SO_t$—$R^{10}$, wherein t is 1 or 2,
5) —($C_0$–$C_6$)-alkyl-($C_6$–$C_{14}$)-aryl, wherein alkyl and aryl independently from one another are unsubstituted or mono-, di- or trisubstituted by R13,
6) —($C_1$–$C_3$)-perfluoroalkyl,
7) —O—$R^{17}$, or 8) —($C_0$–$C_6$)-alkyl-($C_4$–$C_{15}$)-heterocyclyl, wherein alkyl and heterocyclyl independently from one another are unsubstituted or mono-, di- or trisubstituted by R13, or R11 and R12 together with the nitrogen atom to which they are bonded can form a 4- to 8-membered monocyclic heterocyclic ring which in addition to the nitrogen atom can contain one or two identical or different ring heteroatoms chosen from oxygen, sulfur and nitrogen; wherein said heterocyclic ring is unsubstituted or mono-, di- or trisubstituted independently of one another by R13, R13 is halogen, —$NO_2$, —CN, =O, —OH, —$CF_3$, —C(O)—O—$R^{10}$, —C(O)—N($R^{10}$)—$R^{20}$, —N($R^{10}$)—$R^{20}$,
—($C_3$–$C_8$)-cycloalkyl, —($C_0$–$C_3$)-alkylene-O—$R^{10}$, —Si—$(CH_3)_3$, —N($R^{10}$)—S(O)$_u$—$R^{10}$, wherein u is 1 or 2, —S—$R^{10}$, —$SO_r$—$R^{10}$, wherein r is 1 or 2, —S(O)$_v$—N($R^{10}$)—$R^{20}$, wherein v is 1 or 2, —C(O)—$R^{10}$, —($C_1$–$C_8$)-alkyl, —($C_1$–$C_8$)-alkoxy, phenyl, phenyloxy-, —O—$CF_3$, —($C_0$–$C_4$)-alkyl-C(O)—O—C(R15, R16)—O—C(O)—R17, —($C_1$–$C_4$)-alkoxyphenyl, —($C_0$–$C_4$)-alkyl-C(O)—O—C(R15, R16)—O—C(O)—O—R17, —($C_1$–$C_3$)-perfluoroalkyl, —O—R15, —NH—C(O)—NH—$R^{10}$, —NH—C(O)—O—$R^{10}$, or a residue from the following list

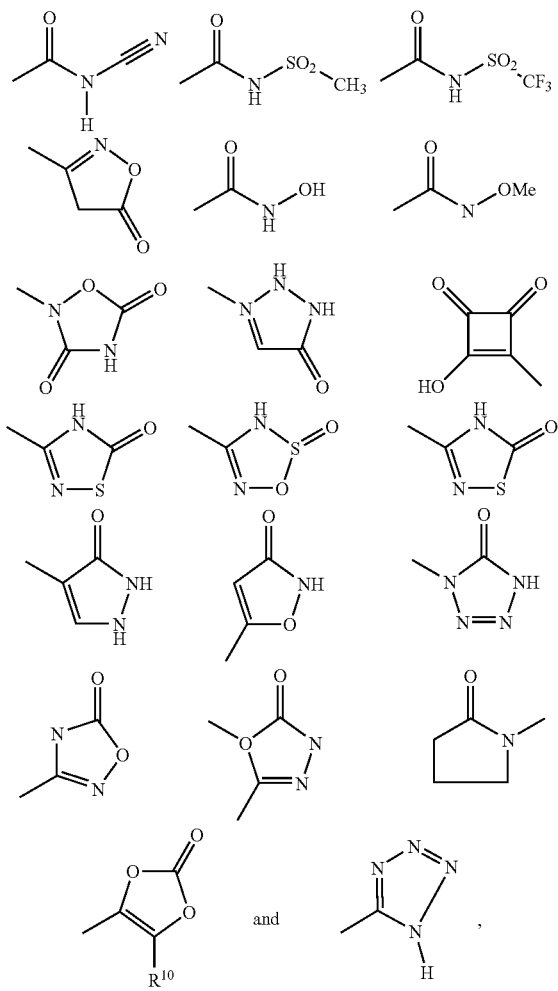

and $R^{10}$ and $R^{20}$ are independently of one another hydrogen, —($C_1$–$C_6$)-alkyl or —($C_1$–$C_3$)-perfluoroalkyl, R15 and R16 are independently of one another hydrogen, —($C_1$–$C_6$)-alkyl, or together with the carbon atom to which they are bonded they can form a 3- to 6 membered carbocyclic ring which is unsubstituted or substituted one to three times by $R^{10}$, and R17 is —($C_1$–$C_6$)-alkyl, —($C_1$–$C_6$)-alkyl-OH, —($C_1$–$C_6$)-alkyl-O—($C_1$–$C_6$)-alkyl, —($C_3$–$C_8$)-cycloalkyl, —($C_1$–$C_6$)-alkyl-O—($C_1$–$C_8$)-alkyl-($C_3$–$C_8$)-cycloalkyl, —($C_1$–$C_6$)-alkyl-($C_3$–$C_8$)-cycloalkyl, wherein said cycloalkyl ring is unsubstituted or substituted one, two or three times by —OH, —O—($C_1$–$C_4$)-alkyl or $R^{10}$, in all its stereoisomeric forms and mixtures thereof in any ratio, and its physiologically tolerable salts 3) Thus, the present invention relates to compounds of the formulae I and II, wherein $J^1$ is N or C, $J^2$ is N or C, $J^3$ is N or C, $J^4$ is N or C and $J^5$ is N or C, provided that
a) $J^1$ is N and $J^2$ is N and $J^3$ is N, or
b) $J^1$ is N and $J^2$ is N and $J^3$ is C, or
c) $J^1$ is N and $J^2$ is C and $J^3$ is N, or
d) $J^1$ is C and $J^2$ is N and $J^3$ is N, or
e) $J^4$ is N and $J^5$ is N, or
f) $J^4$ is N and $J^5$ is C, or
g) $J^4$ is C and $J^5$ is N, and $R^0$ is 1) a monocyclic or bicyclic 6- to 14-membered aryl out of the group phenyl, naphthyl, biphenylyl, anthryl or fluorenyl, wherein aryl is mono-, di- or trisubstituted independently of one another by R8, 2) a heterocyclyl out of the group benzimidazolyl, 1,3-benzodioxolyl, benzofuranyl, benzoxazolyl, benzothiazolyl, benzothiophenyl, cinnolinyl, chromanyl, indazolyl, indolyl, isochromanyl, isoindolyl, isoquinolinyl, phenylpyridyl, phthalazinyl, pteridinyl, purinyl, pyridyl, pyridoimidazolyl, pyridopyridinyl, pyridopyrimidinyl, pyrimidinyl, quinazolinyl, quinolyl, quinoxalinyl or 1,4,5,6-tetrahydro-pyridazinyl, wherein said heterocyclyl is unsubstituted or mono-, di- or trisubstituted independently of one another by R8, or 3) a heterocyclyl, wherein heterocyclyl is selected out of the group acridinyl, azabenzimidazolyl, azaspirodecanyl, azepinyl, azetidinyl, aziridinyl, benzimidazolyl, benzofuranyl, benzothiofuranyl, benzothiophenyl, benzoxazolyl, benzothiazolyl, benztriazolyl, benztetrazolyl, benzisoxazolyl, benzisothiazolyl, carbazolyl, 4aH-carbazolyl, carbolinyl, chromanyl, chromenyl, cinnolinyl, decahydrochinolinyl, 4,5-dihydrooxa-zolinyl, dioxazolyl, dioxazinyl, 1,3-dioxolanyl, 1,3-dioxolenyl, 6H-1,5,2-dithiazinyl, dihydrofuro[2,3-b]-tetrahydrofuranyl, furanyl, furazanyl, imidazolidinyl, imidazolinyl, imidazolyl, 1H-indazolyl, indolinyl, indolizinyl, indolyl, 3H-indolyl, isobenzofuranyl, isochromanyl, isoindazolyl, isoindolinyl, isoindolyl, isoquinolinyl, isothiazolyl, isothiazolidinyl, isothiazolinyl, isoxazolyl, isoxazolinyl, isoxazolidinyl, 2-isoxazolinyl, ketopiperazinyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, 1,2-oxa-thiepanyl, 1,2-oxathiolanyl, 1,4-oxazepanyl, 1,2-oxazinyl, 1,3-oxazinyl, 1,4-oxazinyl, oxazolidinyl, oxazolinyl, oxazolyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazolyl, pyridoimidazolyl, pyridothiazolyl, pyridyl, pyridyl, pyrimidinyl, pyrrolidinyl, pyrrolidinonyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, 1,4,5,6-tetrahydro-pyridazinyl, tetrahydropyridinyl, tetrahydrothiophenyl, tetrazinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, 1,2-thiazinyl, 1,3-thiazinyl, 1,4-thiazinyl, 1,3-thiazolyl, thiazolyl, thiazolidinyl, thiazolinyl, thienyl, thietanyl, thienothiazolyl, thienooxazolyl, thienoimidazolyl, thietanyl, thiomorpholinyl, thiophenolyl, thiophenyl, thiopyranyl, 1,2,3-triazinyl, 1,2,4-triazinyl, 1,3,5-triazinyl, 1,2,3-triazolyl, 1,2,4-triazolyl, 1,2,5-triazolyl, 1,3,4-triazolyl and xanthenyl, wherein said heterocyclyl is unsubstituted or mono-, di- or trisubstituted independently of one another by R8, and which is additionally substituted by a heterocyclyl selected out of the group acridinyl, azabenzimidazolyl, azaspirodecanyl, azepinyl, azetidinyl, aziridinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, carbazolyl, 4aH-carbazolyl, carbolinyl, chromanyl, chromenyl, cinnolinyl, decahydrochinolinyl, 4,5-dihydrooxa-zolinyl, dioxazolyl, dioxazinyl, 1,3-dioxolanyl, 1,3-dioxolenyl, 6H-1,5,2-dithiazinyl, dihydrofuro[2,3-b]-tetrahydrofuranyl, furanyl, furazanyl, imidazolidinyl, imidazolinyl, imidazolyl, 1H-indazolyl, indolinyl, indolizinyl, indolyl, 3H-indolyl, isobenzofuranyl, isochromanyl, isoindazolyl, isoindolinyl, isoindolyl, isoquinolinyl, isothiazolyl, isothiazolidinyl, isothiazolinyl, isoxazolyl, isoxazolinyl, isoxazolidinyl, 2-isoxazolinyl, ketopiperazinyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, 1,2-oxa-thiepanyl, 1,2-oxathiolanyl, 1,4-oxazepanyl, 1,2-oxazinyl, 1,3-oxazinyl, 1,4-oxazinyl, oxazolidinyl, oxazolinyl, oxazolyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazolyl, pyridoimidazolyl, pyridothiazolyl, pyridyl, pyrimidinyl, pyrrolidinyl, pyrrolidinonyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, 1,4,5,6-tetrahydro-pyridazinyl, tetrahydropyridinyl, tetrahydrothiophenyl, tetrazinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, 1,2-thiazinyl, 1,3-thiazinyl, 1,4-thiazinyl, 1,3-thiazolyl, thiazolyl, thiazolidinyl, thiazolinyl, thienyl, thietanyl, thienothiazolyl, thienooxazolyl, thienoimidazolyl, thietanyl, thiomorpholinyl, thiophenolyl, thiophenyl, thiopyranyl, 1,2,3-triazinyl, 1,2,4-triazinyl, 1,3,5-triazinyl, 1,2,3-triazolyl, 1,2,4-triazolyl, 1,2,5-triazolyl, 1,3,4-triazolyl and xanthenyl, wherein heterocyclyl is unsubstituted or mono-, di- or trisubstituted independently of one another by R8, R8 is 1) halogen,
2) —$NO_2$,
3) —CN,
4) —C(O)—$NH_2$,
5) —OH,
6) —$NH_2$,
7) —O—$CF_3$,
8) a monocyclic or bicyclic 6- to 14-membered aryl, wherein aryl is as defined above and wherein aryl is mono-, di- or trisubstituted independently of one another by halogen or —O—($C_1$–$C_8$)-alkyl,
9) —($C_1$–$C_8$)-alkyl, wherein alkyl is unsubstituted or mono-, di- or trisubstituted independently of one another by halogen, $NH_2$, —OH or a methoxy residue, or
10) —O—($C_1$–$C_8$)-alkyl, wherein alkyl is unsubstituted or mono-, di- or trisubstituted independently of one another by halogen, $NH_2$, —OH or a methoxy residue,
11) —$SO_2$—$CH_3$ or
12) —$SO_2$—$CF_3$, provided that R8 is at least one halogen, —C(O)—$NH_2$ or —O—($C_1$–$C_8$)-alkyl residue, if $R^0$ is a monocyclic or bicyclic 6- to 14-membered aryl, wherein aryl is as defined above, Q is a direct bond, —($C_0$–$C_2$)-alkylene-C(O)—$NR^{10}$—, —$NR^{10}$—C(O)—$NR^{10}$—, —$NR^{10}$—C(O)—, —$SO_2$—, —($C_1$–$C_6$)-alkylene, —$(CH_2)_m$—$NR^{10}$—C(O)—$NR^{10}$—$(CH_2)_n$—, —$(CH_2)_m$—$NR^{10}$—C(O)—$(CH_2)_n$—, —$(CH_2)_m$—S—$(CH_2)_n$—, —$(CH_2)_m$—C(O)—$(CH_2)_n$—, —$(CH_2)_m$—$SO_2$—$NR^{10}$—$(CH_2)_n$—, —$(CH_2)_m$—$NR^{10}$—$SO_2$—$(CH_2)_n$—, —$(CH_2)_m$—$NR^{10}$—$SO_2$—$NR^{10}$—$(CH_2)_n$—, —$(CH_2)_m$—CH(OH)—$(CH_2)_n$—, —$(CH_2)_m$—O—C(O)—$NR^{10}$—$(CH_2)_n$—, —($C_2$–$C_3$)-alkylene-O—($C_0$–$C_3$)-alkylene-, —($C_2$–$C_3$)-alkylene-S(O)—, —($C_2$–$C_3$)-alkylene-S(O)$_2$—, —$(CH_2)_m$—$NR^{10}$—C(O)—O—$(CH_2)_n$—, —($C_2$–$C_3$)-alkylene-S(O)$_2$—NH—($R^{10}$)—, —($C_2$–$C_3$)-alkylene-N($R^{10}$)— or —($C_0$–$C_3$)-alkylene-C(O)—O—$(CH_2)_m$—, wherein $R^{10}$ is as defined below, and wherein n and m are independently of one another identical or different and are the integers zero, 1, 2, 3, 4, 5 or 6, wherein the alkylene residues which are formed by —$(CH_2)_m$— or —$(CH_2)_n$— are unsubstituted or mono-, di- or trisubstituted independently of one another by halogen, —$NH_2$ or —OH; or $C_3$–$C_6$-cycloalkylen, wherein cycloalkylen is unsubstituted or mono-, di- or trisubstituted independently of one another by halogen, —$NH_2$ or —OH;

$R^1$ is a hydrogen atom, —($C_1$–$C_4$)-alkyl, wherein alkyl is unsubstituted or substituted one to three times by R13; —($C_1$–$C_3$)-alkylene-C(O)—NH—$R^0$, —($C_1$–$C_3$)-alkylene-C(O)—O—R15, an aryl out of the group phenyl, naphthyl, biphenylyl, anthryl or fluorenyl, wherein aryl is mono-, di- or trisubstituted independently of one another by R8, wherein R8 is as defined above;

a monocyclic or bicyclic 4- to 15-membered heterocyclyl, which is as defined above;

—($C_1$–$C_3$)-perfluoroalkylene, —($C_1$–$C_3$)-alkylene-S(O)—($C_1$–$C_4$)-alkyl, —($C_1$–$C_3$)-alkylene-S(O)$_2$—($C_1$–$C_3$)-alkyl, —($C_1$–$C_3$)-alkylene-S(O)$_2$—N($R^{4'}$)—$R^{5'}$, —($C_1$–$C_3$)-alkylene-O—($C_1$–$C_4$)-alkyl, —($C_0$–$C_3$)-alkylene-($C_3$–$C_8$)-cycloalkyl, or —($C_0$–$C_3$)-alkylene-het, wherein het is a residue selected out of the group azepine, azetidine, aziridine, azirine, 1,4-diazapane, 1,2-diazepine, 1,3-diazepine, 1,4-diazepine, diaziridine, diazirine, dioxazole, dioxazine, dioxole, 1,3-dioxolene, 1,3-dioxolane, furan, imidazole, imidazoline, imidazolidine, isothiazole, isothiazolidine, isothiazoline, isoxazole, isoxazoline, isoxazolidine, 2-isoxazoline, ketopiperazine, morpholine, 1,4- oxazepane, 1,2-oxa-thiepane, 1,2-oxathiolane, 1,2-oxazine, 1,3-oxazine, 1,4-oxazine, oxazole, oxaziridine, oxirane, piperazine, piperidine, pyran, pyrazine, pyrazole, pyrazoline, pyrazolidine, pyridazine, pyridine, pyrimidine, pyrrole, pyrrolidine, pyrrolidinone, pyrroline, tetrahydropyridine, tetrazine, tetrazole, thiadiazine thiadiazole, 1,2-thiazine, 1,3-thiazine, 1,4-thiazine, 1,3-thiazole, thiazole, thiazolidine, thiazoline, thienyl, thietan, thiomorpholine, thiopyran, 1,2,3-triazine, 1,2,4-triazine, 1,3,5-triazine, 1,2,3-triazole or 1,2,4-triazole, wherein het is unsubstituted or mono-, di- or trisubstituted independently of one another by R14, $R^{4'}$ and $R^{5'}$ are independent of one another are identical or different and are hydrogen atom or —$(C_1-C_4)$-alkyl, $R^2$ is a direct bond or —$(C_1-C_4)$-alkylene, or $R^1$ and R3 together with the atoms to which they are bonded can form a 6- to 8-membered cyclic residue selected out of the group azocane, azocane-2-one, 1,2-diazepine, 1,3-diazepine, 1,4-diazepine, [1,4]diazocane, [1,2]diazocan-3-one, [1,3]diazocan-2-one, dioxazine, [1,4]dioxocane, dioxole, ketopiperazine, morpholine, 1,2-oxazine, 1,3-oxazine, 1,4-oxazine, [oxocane, oxocan-2-one, piperazine, piperidine, pyran, pyrazine, pyridazine, pyrimidine or 5,6,7,8-tetrahydro-1H-azocin-2-one, wherein said cyclic group is unsubstituted or mono-, di- or trisubstituted independently of one another by R14, or $R^1$—N—$R^2$—V can form a 4- to 8-membered cyclic group selected out of the group azepine, azetidine, dioxazole, dioxazine, 1,2-diazepine, 1,3-diazepine, 1,4-diazepine, imidazole, imidazoline, imidazolidine, isothiazole, isothiazolidine, isothiazoline, isoxazole, isoxazoline, isoxazolidine, 2-isoxazoline, ketopiperazine, morpholine, oxazole, piperazine, piperidine, pyrazine, pyrazole, pyrazoline, pyrazolidine, pyridazine, pyridine, pyrimidine, pyrrole, pyrrolidine, pyrrolidinone, pyrroline, tetrahydropyridine, tetrazine, tetrazole, thiazole, thiadiazole, thiazolidine, thiazoline, thiomorpholine, 1,2,3-triazine, 1,2,4-triazine, 1,3,5-triazine, 1,2,3-triazole or 1,2,4-triazole, wherein said cyclic group is unsubstituted or mono-, di- or trisubstituted independently of one another by R14, R14 is fluorine, chlorine, bromine, iodine, —OH, =O, —$(C_1-C_8)$-alkyl, —$(C_1-C_4)$-alkoxy, —$NO_2$, —C(O)—OH, —CN, —$NH_2$, —C(O)—O—$(C_1-C_4)$-alkyl, —$(C_0-C_8)$-alkyl-$SO_2$-$(C_1-C_4)$-alkyl, —$(C_0-C_8)$-alkyl-$SO_2$—$(C_1-C_3)$-perfluoroalkyl, —$(C_0-C_8)$-alkyl-$SO_2$—$N(R^{18})$—$R^{21}$, —C(O)—NH—$(C_1-C_8)$-alkyl, —C(O)—N—$[(C_1-C_8)$-alkyl$]_2$, —$NR^{18}$—C(O)—NH—$(C_1-C_8)$-alkyl, —C(O)—$NH_2$, —S—$R^{18}$, or —$NR^{18}$—C(O)—NH-$[(C_1-C_8)$-alkyl$]_2$,
 wherein $R^{18}$ and $R^{21}$ are independently from each other hydrogen atom, —$(C_1-C_3)$-perfluoroalkyl or —$(C_1-C_6)$-alkyl, V is 1) a monocyclic or bicyclic 6- to 14-membered aryl out of the group phenyl, naphthyl, biphenylyl, anthryl or fluorenyl, wherein aryl is mono-, di- or trisubstituted independently of one another by R14, 2) a heterocyclyl out of the group acridinyl, azaindole (1H-pyrrolopyridine), azabenzimidazolyl, azaspirodecanyl, azepinyl, azetidinyl, aziridinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, carbazolyl, 4aH-carbazolyl, carbolinyl, chromanyl, chromenyl, cinnolinyl, decahydrochinolinyl, 1,4-diazepane, 4,5-dihydrooxazolinyl, dioxazolyl, dioxazinyl, 1,3-dioxolanyl, 1,3-dioxolenyl, 6H-1,5,2-dithiazinyl, dihydrofuro[2,3-b]-tetrahydrofuranyl, furanyl, furazanyl, imidazolidinyl, imidazolinyl, imidazolyl, 1H-indazolyl, indolinyl, indolizinyl, indolyl, 3H-indolyl, isobenzofuranyl, isochromanyl, isoindazolyl, isoindolinyl, isoindolyl, isoquinolinyl, isothiazolyl, isothiazolidinyl, isothiazolinyl, isoxazolyl, isoxazolinyl, isoxazolidinyl, 2-isoxazolinyl, ketopiperazinyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, 1,2-oxa-thiepanyl, 1,2-oxathiolanyl, 1,4-oxazepanyl, 1,2-oxazinyl, 1,3-oxazinyl, 1,4-oxazinyl, oxazolidinyl, oxazolinyl, oxazolyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazolyl, pyridoimidazolyl, pyridothiazolyl, pyridinyl, pyridyl, pyrimidinyl, pyrrolidinyl, pyrrolidinonyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisochinolinyl, tetrahydrochinolinyl, 1,4,5,6-tetrahydro-pyridazinyl, tetrahydropyridinyl, tetrahydrothiophenyl, tetrazinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, 1,2-thiazinyl, 1,3-thiazinyl, 1,4-thiazinyl, 1,3-thiazolyl, thiazolyl, thiazolidinyl, thiazolinyl, thienyl, thietanyl, thienothiazolyl, thienooxazolyl, thienoimidazolyl, thietanyl, thiomorpholinyl, thiophenyl, thiopyranyl, 1,2,3-triazinyl, 1,2,3-triazolyl, 1,2,3-triazolyl, 1,2,4-triazolyl, 1,2,5-triazolyl, 1,3,4-triazolyl and xanthenyl, wherein said heterocyclyl is unsubstituted or mono-, di- or trisubstituted independently of one another by R14, G is a direct bond, —$(CH_2)_m$—$NR^{10}$—$SO_2$—$NR^{10}$—$(CH_2)_n$—, —$(CH_2)_m$—CH(OH)—$(CH_2)_n$—, —$(CH_2)_m$—, $(CH_2)_m$—O—$(CH_2)_n$—, —$(CH_2)_m$—C(O)—$NR^{10}$—$(CH_2)_n$—, —$(CH_2)$—$SO_2$—$(CH_2)_n$—, —$(CH_2)_m$—$NR^{10}$—C(O)—$NR^{10}$—$(CH_2)_n$—, —$(CH_2)_m$—$NR^{10}$—C(O)—$(CH_2)_n$—, —$(CH_2)_m$—C(O)—$(CH_2)_n$—, —$(CH_2)$—S$(CH_2)_n$—, —$(CH_2)_m$—$SO_2$—$NR^{10}$—$(CH_2)_n$—, —$(CH_2)_m$—$NR^{10}$—$SO_2$—$(CH_2)_n$—, —$(CH_2)_m$—$NR^{10}$—, —$(CH_2)_m$—O—C(O)—$NR^{10}$—$(CH_2)_n$— or —$(CH_2)_m$—$NR^{10}$—C(O)—O—$(CH_2)_n$—, n and m are independently of one another identical or different and are the integers zero, 1, 2, 3, 4, 5 or 6, M is 1) a hydrogen atom, 2) —$(C_1-C_8)$-alkyl, wherein alkyl is unsubstituted or mono-, di- or trisubstituted independently of one another by R14,

3) —C(O)—N(R11)—R12,

4) —$(CH_2)_m$—$NR^{10}$,

5) —$(C_6-C_{14})$-aryl, wherein aryl is as defined above and wherein aryl is unsubstituted or mono-, di- or trisubstituted independently of one another by R14, 6) —$(C_4-C_{15})$-heterocyclyl, wherein heterocyclyl is as defined above and is unsubstituted or mono-, di- or trisubstituted independently of one another by R14, or 7) —$(C_3-C_8)$-cycloalkyl, wherein said cycloalkyl is unsubstituted or mono-, di- or trisubstituted independently of one another by R14, $R^3$ is 1) hydrogen atom, 2) halogen, 3) —($C_1$–$C_4$)-alkyl, wherein alkyl is unsubstituted or mono-, di- or trisubstituted independently of one another by R13,
4) —($C_1$–$C_3$)-perfluoroalkyl,
5) phenyl, wherein phenyl is unsubstituted or mono-, di- or trisubstituted independently of one another by R13,
6) —($C_0$–$C_4$)-alkylene-O—R19, wherein R19 is
   a) hydrogen atom,
   b) —($C_1$–$C_4$)-alkyl, wherein alkyl is unsubstituted or mono-, di- or trisubstituted independently of one another by R13,
   c) phenyl, wherein phenyl is unsubstituted or mono-, di- or trisubstituted independently of one another by R13,
   d) —$CF_3$ or
   e) —$CHF_2$,
7) —$NO_2$,
8) —CN,
9) —$SO_s$—$R^{11}$, wherein s is 1 or 2,
10) —$SO_t$—N($R^{11}$)—$R^{12}$, wherein t is 1 or 2,
11) —($C_0$–$C_4$)-alkylene-C(O)—$R^{11}$,
12) —($C_0$–$C_4$)-alkylene-C(O)—O—$R^{11}$,
13) —($C_0$–$C_4$)-alkylene-C(O)—N($R^{11}$)—$R^{12}$,
14) —($C_0$–$C_4$)-alkylene-N($R^{11}$)—$R^{12}$,
15) —$NR^{10}$—$SO_2$—$R^{10}$,
16) —S—$R^{10}$,
17) —($C_0$–$C_2$)alkylene-C(O)—O—($C_2$–$C_4$)-alkylene-O—C(O)—($C_1$–$C_4$)-alkyl,
18) —C(O)—O—C(R15, R16)—O—C(O)—R17,
19) —($C_0$–$C_2$)alkylene-C(O)—O—($C_2$–$C_4$)-alkylene-O—C(O)—O—($C_1$–$C_6$)-alkyl,
20) —C(O)—O—C(R15, R16)—O—C(O)—O—R17,
21) —($C_0$–$C_4$)-alkylene-($C_6$–$C_{14}$)-aryl, wherein aryl is mono-, di- or trisubstituted independently of one another by R13,
22) —($C_0$–$C_4$)-alkylene-($C_4$–$C_{15}$)-heterocyclyl, wherein heterocyclyl is unsubstituted or mono-, di- or trisubstituted independently of one another by R13,
23) —($C_0$–$C_4$)-alkylene-($C_3$–$C_8$)-cycloalkyl, wherein cycloalkyl is unsubstituted or mono-, di- or trisubstituted independently of one another by R13,
24) —($C_0$–$C_4$)-alkylene-het, wherein het is unsubstituted or mono-, di- or trisubstituted independently of one another by R13,
25) —($C_0$–$C_3$)-alkylene-O—$CH_2$—($C_1$–$C_3$)-perfluoroalkylene-$CH_2$—O—($C_0$–$C_3$)-alkyl,
26) —$SO_w$—N($R^{11}$)—$R^{13}$, wherein w is 1 or 2,
27) —($C_0$–$C_4$)-alkylene-C(O)—N($R^{11}$)—$R^{13}$,
28) —($C_0$–$C_4$)-alkylene-N($R^{11}$)—$R^{13}$, or
29) a residue from the following list

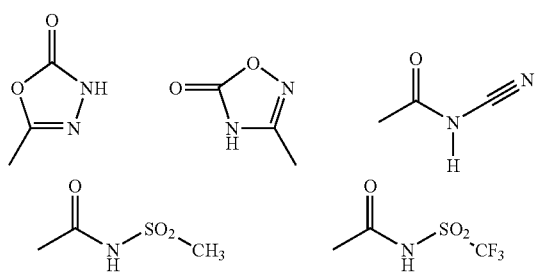

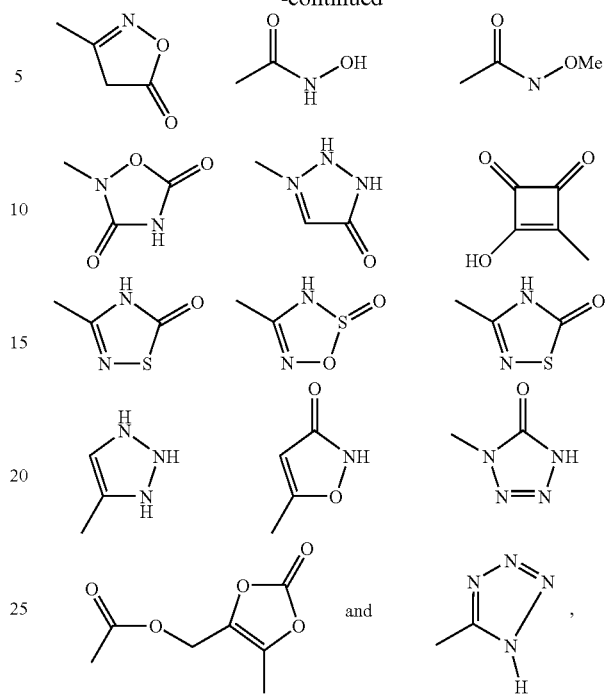

wherein Me is methyl, or if two —OR19 residues are attached to adjacent atoms they can form together with the atoms which they are attached to a 1,3-dioxole ring or a 2,3-dihydro-[1,4]dioxine ring, which is substituted one, two, three or four times by R13, provided that $R^3$ can be attached at any position on the ring of formulae I and II and can occur one, two or three times and is independently of one another identical or different, R11 and R12 are independently of one another identical or different and are
1) hydrogen atom,
2) —($C_1$–$C_6$)-alkyl, wherein alkyl is unsubstituted or mono-, di- or trisubstituted independently of one another by R13,
3) —($C_0$–$C_6$)-alkyl-($C_3$–$C_8$)-cycloalkyl,
4) —$SO_t$—$R^{10}$, wherein t is 1 or 2,
5) —($C_0$–$C_6$)-alkyl-($C_6$–$C_{14}$)-aryl, wherein alkyl and aryl independently from one another are unsubstituted or mono-, di- or trisubstituted by R13,
6) —($C_1$–$C_3$)-perfluoroalkyl,
7) —O—$R^{17}$, or
8) —($C_0$–$C_6$)-alkyl-($C_4$–$C_{15}$)-heterocyclyl, wherein alkyl and heterocyclyl are as defined above and are independently from one another unsubstituted or mono- di- or trisubstituted by R13, or R11 and R12 together with the nitrogen atom to which they are bonded form a heterocyclic ring out of the group azaspirodecan, azepine, azetidine, dioxazole, dioxazine, 1,4-diazepane, 1,2-diazepine, 1,3-diazepine, 1,4-diazepine, imidazole, imidazoline, imidazolidine, isothiazole, isothiazolidine, isothiazoline, isoxazole, isoxazoline, isoxazolidine, 2-isoxazoline, ketopiperazine, morpholine, [1,4]oxazepane, oxazole, piperazine, piperidine, pyrazine, pyrazole, pyrazoline, pyrazolidine, pyridazine, pyridine, pyrimidine, pyrrole, pyrrolidine, pyrrolidinone, pyrroline, tetrahydropyridine, tetrazine, tetrazole, thiazole, thiadiazole, thiazolidine, thiazoline, thiomorpholine, thiophene, 1,2,3-triazine, 1,2,4-triazine, 1,3,5-triazine, 1,2,3-triazole or 1,2,4-triazole, wherein said heterocyclic ring is unsubstituted or mono-, di- or trisubstituted independently of one another by R13, R13 is halogen, —NO$_2$, —CN, =O, —OH, —CF$_3$, —C(O)—O—R$^{10}$, —C(O)—N(R$^{10}$)—R$^{20}$, —N(R$^{10}$)—R$^{20}$, —(C$_3$–C$_8$)-cycloalkyl, —(C$_0$–C$_3$)-alkylene-O—R$^{10}$, —Si—(CH$_3$)$_3$, —N(R$^{10}$)—S(O)$_u$—R$^{10}$, wherein u is 1 or 2, —S—R$^{10}$, —SO$_r$—R$^{10}$, wherein r is 1 or 2, —S(O)$_v$—N(R$^{10}$)—R$^{20}$, wherein v is 1 or 2, —C(O)—R$^{10}$, —(C$_1$–C$_8$)-alkyl, —(C$_1$–C$_8$)-alkoxy, phenyl, phenyloxy-, —O—CF$_3$, —(C$_0$–C$_4$)-alkyl-C(O)—O—C(R15, R16)-O—C(O)—R17, —(C$_1$–C$_4$)-alkoxy-phenyl, —(C$_0$–C$_4$)-alkyl-C(O)—O—C(R15, R16)—O—C(O)—O—R17, —(C$_1$–C$_3$)-perfluoroalkyl, —O—R15, —NH—C(O)—NH—R$^{10}$, —NH—C(O)—O—R$^{10}$, or a residue from the following list

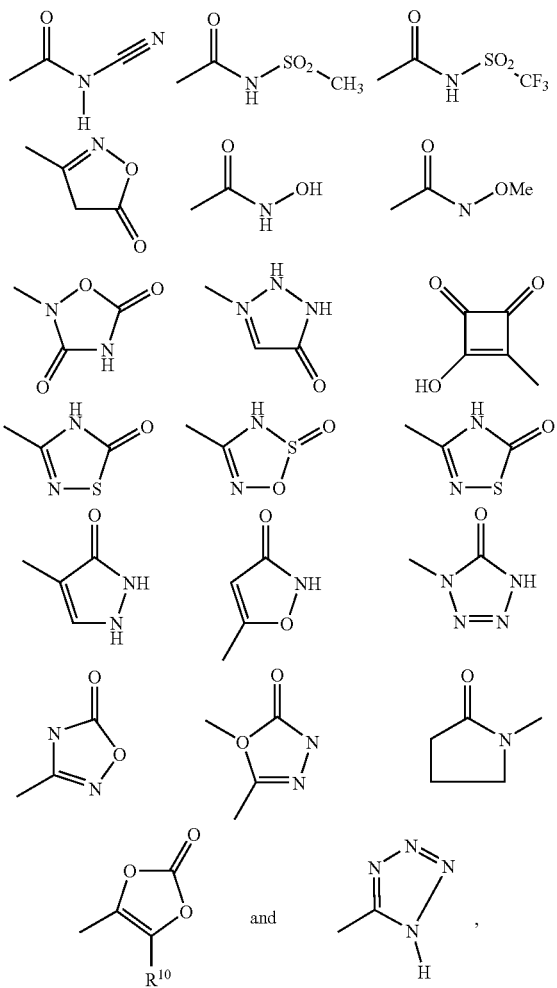

and

R$^{10}$ and R$^{20}$ are independently of one another hydrogen, —(C$_1$–C$_6$)-alkyl, —(C$_0$–C$_4$)-alkyl-OH, —(C$_0$–C$_4$)-alkyl-O—(C$_1$–C$_4$)-akyl or —(C$_1$–C$_3$)-perfluoroalkyl, R15 and R16 are independently of one another hydrogen, —(C$_1$–C$_6$)-alkyl, cyclopropyl, cyclobutyl, cyclopentyl or cyclohexyl, wherein each ring is unsubstituted or substituted one to three times by R$^{10}$, and R17 is —(C$_1$–C$_6$)-alkyl, —(C$_1$–C$_6$)-alkyl-OH, —(C$_1$–C$_6$)-alkyl-O—(C$_1$–C$_6$)-alkyl, —(C$_3$–C$_8$)-cycloalkyl, —(C$_1$–C$_6$)-alkyl-O—(C$_1$–C$_8$)-alkyl-(C$_3$–C$_8$)-cycloalkyl, —(C$_1$–C$_6$)-alkyl-(C$_3$–C$_8$)-cycloalkyl, wherein said cycloalkyl ring is unsubstituted or substituted one, two or three times by —OH, —O—(C$_1$–C$_4$)-alkyl or R$^{10}$, in all its stereoisomeric forms and mixtures thereof in any ratio, and its physiologically tolerable salts 4) The present invention also relates to the compounds of the formulae I and II, wherein J$^1$ is N or C, J$^2$ is N or C, J$^3$ is N or C, J$^4$ is N or C and J$^5$ is N or C,
provided that
  a) J$^1$ is N and J$^2$ is C and J$^3$ is N, or
  b) J$^4$ is N and J$^5$ is N, or
  c) J$^4$ is N and J$^5$ is C, and R$^0$ is 1) a monocyclic or bicyclic 6- to 14-membered aryl out of the group phenyl, naphthyl, biphenyl, anthryl or fluorenyl, wherein aryl is mono-, di- or trisubstituted independently of one another by R8,
  2) a heterocyclyl out of the group benzimidazolyl, 1,3-benzodioxolyl, benzofuranyl, benzoxazolyl, benzothiazolyl, benzothiophenyl, cinnolinyl, chromanyl, indazolyl, indolyl, isochromanyl, isoindolyl, isoquinolinyl, phenylpyridyl, phthalazinyl, pteridinyl, purinyl, pyridyl, pyridoimidazolyl, pyridopyridinyl, pyridopyrimidinyl, pyrimidinyl, quinazolinyl, quinolyl, quinoxalinyl or 1,4,5,6-tetrahydro-pyridazinyl, wherein said heterocyclyl is unsubstituted or mono-, di- or trisubstituted independently of one another by R8, or
  3) a heterocyclyl out of the group azabenzimidazolyl, benzimidazolyl, 1,3-benzodioxolyl, benzofuranyl, benzothiazolyl, benzothiophenyl, benzoxazolyl, chromanyl, cinnolinyl, 2-furyl, 3-furyl; imidazolyl, indolyl, indazolyl, isochromanyl, isoindolyl, isoquinolinyl, isothiazolyl, isoxazolyl, oxazolyl, phthalazinyl, pteridinyl, purinyl, pyrazinyl, pyrazolyl, pyridazinyl, pyridoimidazolyl, pyridopyridinyl, pyridopyrimidinyl, 2-pyridyl, 3-pyridyl, 4-pyridyl, pyrimidinyl, pyrrolyl; 2-pyrrolyl, 3-pyrrolyl, quinolinyl, quinazolinyl, quinoxalinyl, tetrazolyl, thiazolyl, 2-thienyl or 3-thienyl, which is additionally substituted by a heterocyclyl selected out of the group acridinyl, azabenzimidazolyl, azaspirodecanyl, azepinyl, azetidinyl, aziridinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, carbazolyl, 4aH-carbazolyl, carbolinyl, chromanyl, chromenyl, cinnolinyl, decahydrochinolinyl, 4,5-dihydrooxa-zolinyl, dioxazolyl, dioxazinyl, 1,3-dioxolanyl, 1,3-dioxolenyl, 6H-1,5,2-dithiazinyl, dihydrofuro[2,3-b]-tetrahydrofuranyl, furanyl, furazanyl, imidazolidinyl, imidazolinyl, imidazolyl, 1H-indazolyl, indolinyl, indolizinyl, indolyl, 3H-indolyl, isobenzofuranyl, isochromanyl, isoindazolyl, isoindolinyl, isoindolyl, isoquinolinyl (benzimidazolyl), isothiazolyl, isothiazolidinyl, isothiazolinyl, isoxazolyl, isoxazolinyl, isoxazolidinyl, 2-isoxazolinyl, ketopiperazinyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, 1,2-oxa-thiepanyl, 1,2-oxathiolanyl, 1,4-oxazepanyl, 1,2-oxazinyl, 1,3-oxazinyl, 1,4-oxazinyl, oxazolidinyl, oxazolinyl, oxazolyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazolyl, pyridoimidazolyl, pyridothiazolyl, pyridyl, pyridyl, pyrimidinyl, pyrrolidinyl, pyrrolidinonyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisochinolinyl, tetrahydrochinolinyl, 1,4,5,6-tetrahydro-pyridazinyl, tetrahydropyridinyl, tetrahydrothiophenyl, tetrazinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, 1,2-thiazinyl, 1,3-thiazinyl, 1,4-thiazinyl, 1,3-thiazolyl, thiazolyl, thiazolidinyl, thiazolinyl, thienyl, thietanyl, thienothiazolyl, thienooxazolyl, thienoimidazolyl, thietanyl, thiomorpholinyl, thiophenyl, thiopyranyl, 1,2,3-triazinyl, 1,2,3-triazolyl, 1,2,3-triazolyl, 1,2,4-triazolyl, 1,2,5-triazolyl, 1,3,4-triazolyl and xanthenyl, wherein heterocyclyl is unsubstituted or mono-, di- or trisubstituted independently of one another by R8, R8 is 1. fluorine, chlorine or bromine,
2. $-NO_2$,
3. $-CN$,
4. $-C(O)-NH_2$,
5. $-OH$,
6. $-NH_2$,
7. $-OCF_3$
8. a monocyclic or bicyclic 6- to 14-membered aryl, wherein aryl is as defined above and is mono-, di- or trisubstituted independently of one another by halogen or $-O-(C_1-C_8)$-alkyl,
9. $-(C_1-C_8)$-alkyl, wherein alkyl is unsubstituted or mono-, di- or trisubstituted independently of one another by halogen, $NH_2$, $-OH$ or a methoxy residue, or
10. $-O-(C_1-C_8)$-alkyl, wherein alkyl is unsubstituted or mono-, di- or trisubstituted independently of one another by halogen, $NH_2$, $-OH$ or a methoxy residue,
11. $-SO_2CH_3$ or
12. $-SO_2CF_3$, provided that R8 is at least one halogen, $-C(O)-NH_2$ or $-O-(C_1-C_8)$-alkyl residue, if R0 is a aryl or a heterocyclyl, which are as defined above, Q is a direct bond, $-(C_0-C_2)$-alkylene-$C(O)-NR^{10}-$, $-NR^{10}-C(O)-NR^{10}-$, $-NR^{10}-C(O)-$, $-SO_2-$, $-(C_1-C_6)$-alkylene or $-(C_0-C_3)$-alkylene-$C(O)-O-(C_0-C_2)$-alkylene, $R^1$ is a hydrogen atom, $-(C_1-C_4)$-alkyl, wherein alkyl is unsubstituted or substituted one to three times by R13; $-(C_1-C_3)$-alkylene-$C(O)-NH-R^0$, $-(C_1-C_3)$-alkylene-$C(O)-O-R15-(C_1-C_3)$-perfluoroalkylene, $-(C_1-C_3)$-alkylene-$S(O)-(C_1-C_4)$-alkyl, $-(C_1-C_3)$-alkylene-$S(O)_2-(C_1-C_3)$-alkyl, $-(C_1-C_3)$-alkylene-$S(O)_2-N(R^{4'})-R^{5'}$, $-(C_1-C_3)$-alkylene-$O-(C_1-C_4)$-alkyl, $-(C_0-C_3)$-alkylene-$(C_3-C_8)$-cycloalkyl, or $-(C_0-C_3)$-alkylene-het, wherein het is a residue selected out of the group azepine, azetidine, aziridine, azirine, 1,4-diazepane, 1,2-diazepine, 1,3-diazepine, 1,4-diazepine, diaziridine, diazirine, dioxazole, dioxazine, dioxazine, dioxole, 1,3-dioxolene, 1,3-dioxolane, furan, imidazole, imidazoline, imidazolidine, isothiazole, isothiazolidine, isothiazoline, isoxazole, isoxazoline, isoxazolidine, 2-isoxazoline, ketopiperazine, morpholine, 1,2-oxa-thiepane, 1,2-oxathiolane, 1,4-oxazepane, 1,2-oxazine, 1,3-oxazine, 1,4-oxazine, oxazole, oxaziridine, oxirane, piperazine, piperidine, pyran, pyrazine, pyrazole, pyrazoline, pyrazolidine, pyridazine, pyridine, pyrimidine, pyrrole, pyrrolidine, pyrrolidinone, pyrroline, tetrahydropyridine, tetrazine, tetrazole, thiadiazine thiadiazole, 1,2-thiazine, 1,3-thiazine, 1,4-thiazine, 1,3-thiazole, thiazole, thiazolidine, thiazoline, thienyl, thietan, thiomorpholine, thiopyran, 1,2,3-triazine, 1,2,4-triazine, 1,3,5-triazine, 1,2,3-triazole or 1,2,4-triazole, wherein het is unsubstituted or mono-, di- or trisubstituted independently of one another by R14, $R^{4'}$ and $R^{5'}$ are independent of one another are identical or different and are hydrogen atom or $-(C_1-C_4)$-alkyl, $R^2$ is a direct bond or $-(C_1-C_4)$-alkylene, or $R^1-N-R^2-V$ form a 4- to 8-membered cyclic group selected out of the group azepine, azetidine, 1,4-diazepane, dioxazole, dioxazine, 1,2-diazepine, 1,3-diazepine, 1,4-diazepine, imidazole, imidazoline, imidazolidine, isothiazole, isothiazolidine, isothiazoline, isoxazole, isoxazoline, isoxazolidine, 2-isoxazoline, ketopiperazine, morpholine, 1,4-oxazepane, oxazole, piperazine, piperidine, pyrazine, pyrazole, pyrazoline, pyrazolidine, pyridazine, pyridine, pyrimidine, pyrrole, pyrrolidine, pyrrolidinone, pyrroline, tetrahydropyridine, tetrazine, tetrazole, thiazole, thiadiazole, thiazolidine, thiazoline, thiomorpholine, 1,2,3-triazine, 1,2,4-triazine, 1,3,5-triazine, 1,2,3-triazole or 1,2,4-triazole, wherein said cyclic group is unsubstituted or mono-, di- or trisubstituted independently of one another by R14, R14 is fluorine, chlorine, bromine, iodine, $-OH$, $=O$, $-(C_1-C_8)$-alkyl, $-(C_1-C_4)$-alkoxy, $-NO_2$, $-C(O)-OH$, $-CN$, $-NH_2$, $-C(O)-O-(C_1-C_4)$-alkyl, $-(C_0-C_8)$-alkyl-$SO_2(C_1-C_4)$-alkyl, $-(C_0-C_8)$-alkyl-$SO_2-(C_1-C_3)$-perfluoroalkyl, $-(C_0-C_8)$-alkyl-$SO_2-N(R^{18})-R^{21}$, $-C(O)-NH-(C_1-C_8)$-alkyl, $-C(O)-N-[(C_1-C_8)$-alkyl$]_2$, $-NR^{18}-C(O)-NH-(C_1-C_8)$-alkyl, $-C(O)-NH_2$, $-S-R^{18}$, or $-NR^{18}-C(O)-NH-[(C_1-C_8)$-alkyl$]_2$, wherein $R^{18}$ and $R^{21}$ are independently from each other hydrogen atom, $-(C_1-C_3)$-perfluoroalkyl or $C_1-C_6$)-alkyl, V is 1) a het residue out of the group azaindole (1H-pyrrolopyridine), azepine, azetidine, aziridine, azirine, 1,4-diazepane, 1,2-diazepine, 1,3-diazepine, 1,4-diazepine, diaziridine, diazirine, dioxazole, dioxazine, dioxole, 1,3-dioxolene, 1,3-dioxolane, furan, imidazole, imidazoline, imidazolidine, isothiazole, isothiazolidine, isothiazoline, isoxazole, isoxazoline, isoxazolidine, 2-isoxazoline, ketopiperazine, morpholine, 1,2-oxa-thiepane, 1,2-oxathiolane, 1,4-oxazepane, 1,2-oxazine, 1,3-oxazine, 1,4-oxazine, oxazole, oxaziridine, oxirane, piperazine, piperidine, pyran, pyrazine, pyrazole, pyrazoline, pyrazolidine, pyridazine, pyridine, pyrimidine, pyrrole, pyrrolidine, pyrrolidinone, pyrroline, tetrahydropyridine, tetrazine, tetrazole, thiadiazine, thiadiazole, 1,2-thiazine, 1,3-thiazine, 1,4-thiazine, 1,3-thiazole, thiazole, thiazolidine, thiazoline, thienyl, thietan, thiomorpholine, thiopyran, 1,2,3-triazine, 1,2,4-triazine, 1,3,5-triazine, 1,2,3-triazole or 1,2,4-triazole, which is as defined above and wherein het is unsubstituted or mono-, di- or trisubstituted independently of one another by R14, or 2) phenyl, wherein phenyl is unsubstituted or mono-, di- or trisubstituted independently of one another by R14, G is a direct bond, $-(CH_2)_m-NR^{10}-SO_2-NR^{10}-(CH_2)_n-$, $-(CH_2)_m-CH(O)-(CH_2)_n-$, $-(CH_2)_m-$, $-(CH_2)_m-O-(CH_2)_n-$, $-(CH_2)_mC(O)-NR^{10}-(CH_2)_n-$, $-(CH_2)-SO_2-(CH_2)_n-$, $-(CH_2)_m-NR^{10}-C(O)-NR^{10}-(CH_2)_n-$, $-(CH_2)_m-NR^{10}-C(O)-(CH_2)_n-$, $-(CH_2)_m-C(O)-(CH_2)_n-$, $-(CH_2)-S-(CH_2)_n-$, $-(CH_2)_m-SO_2-NR^{10}-(CH_2)_n-$, $-(CH_2)_m-NR^{10}-SO_2-(CH_2)_n-$, $-(CH_2)_m-NR^{10}-$, $-(CH_2)_m-O-C(O)-NR^{10}-(CH_2)_n-$, or $-(CH_2)_m-NR^{10}-C(O)-O-(CH_2)_n-$, n and m are independently of one another identical or different and are the integers zero, 1, 2, 3, 4, 5 or 6, M is 1) a hydrogen atom,
2) $-(C_1-C_8)$-alkyl, wherein alkyl is unsubstituted or mono-, di- or trisubstituted independently of one another by R14,
3) $-C(O)-N(R11)-R12$,
4) $-(CH_2)_m-NR^{10}$,
5) phenyl or naphthyl, wherein phenyl or naphthyl are unsubstituted or mono-, di- or trisubstituted independently of one another by R14,
6) heterocyclyl, wherein heterocyclyl is a residue out of the group which can be derived from azepane, azepine, 1,4-diazepane, 1,2-diazepine, 1,3-diazepine, 1,4-diazepine, imidazole, isothiazole, isoxazole, isoxazolidine, 2-isoxazoline, ketomorpholine, ketopiperazine, morpholine, oxazole, [1,4]-oxazepane, piperazine, piperazinone, piperidine, piperidinone, pyrazine, pyridazine, pyridazinone, pyridine, pyridone, pyrimidine, pyrrolidine, pyrrolidinone, tetrahydropyran, 1,4,5,6-tetrahydro-pyridazinyl, tetrazine, tetrazole, thiadiazole, thiazole, thiophene, thiomorpholine, 1,2,3-triazine, 1,2,4-triazine, 1,3,5-triazine, 1,2,3-triazole or 1,2,4-triazole, wherein said heterocyclyl is unsubstituted or mono-, di- or trisubstituted independently of one another by R14, or
7) $-(C_3-C_8)$-cycloalkyl, wherein said cycloalkyl is unsubstituted or mono-, di- or trisubstituted independently of one another by R14, $R^3$ is
1) hydrogen atom,
2) halogen,
3) $-(C_1-C_4)$-alkyl, wherein alkyl is unsubstituted or mono-, di- or trisubstituted independently of one another by R13,
4) $-(C_1-C_3)$-perfluoroalkyl,
5) phenyl, wherein phenyl is unsubstituted or mono-, di- or trisubstituted independently of one another by R13,
6) $-(C_0-C_4)$-alkylene-O-R19, wherein R19 is
  a) hydrogen atom,
  b) $-(C_1-C_4)$-alkyl, wherein alkyl is unsubstituted or mono-, di- or trisubstituted independently of one another by R13,
  c) phenyl, wherein phenyl is unsubstituted or mono-, di- or trisubstituted independently of one another by R13,
  d) $-CF_3$ or
  e) $CHF_2$,
7) $-CN$,
8) $-(C_0-C_4)$-alkylene-$(C_4-C_{15})$-heterocyclyl, wherein heterocyclyl is as defined above and is unsubstituted or mono-, di- or trisubstituted independently of one another by R13,
9) $-SO_s-R^{11}$, wherein s is 1 or 2,
10) $-SO_t-N(R^{11})-R^{12}$, wherein t is 1 or 2,
11) $-(C_0-C_4)$-alkylene-C(O)-$R^{11}$,
12) $-(C_0-C_4)$-alkylene-C(O)-O-$R^{11}$,
13) $-(C_0-C_4)$-alkylene-C(O)-N($R^{11}$)-$R^{12}$,
14) $-(C_0-C_4)$-alkylene-N($R^{11}$)-$R^{12}$,
15) $-NR^{10}-SO_2-R^{10}$,
16) $-(C_0-C_4)$-alkylene-het, wherein het is as defined above and is unsubstituted or mono-, di- or trisubstituted independently of one another by R13,
17) $-(C_0-C_2)$alkylene-C(O)-O-$(C_2-C_4)$-alkylene-O-C(O)-$(C_1-C_4)$-alkyl,
18) $-C(O)-O-C(R15, R16)-O-C(O)-R17$,
19) $-(C_0-C_2)$alkylene-C(O)-O-$(C_2-C_4)$-alkylene-O-C(O)-O-$(C_1-C_6)$-alkyl,
20) $-C(O)-O-C(R15, R16)-O-C(O)-O-R17$,
21) $-(C_0-C_4)$-alkylene-$(C_6-C_{14})$-aryl, wherein aryl is as defined above and is mono-, di- or trisubstituted independently of one another by R13,
22) $-(C_0-C_4)$-alkylene-$(C_3-C_8)$-cycloalkyl, wherein cycloalkyl is unsubstituted or mono-, di- or trisubstituted independently of one another by R13,
23) $-(C_0-C_3)$-alkylene-O-$CH_2$-$CF_2$-$CH_2$-O-$(C_0-C_3)$-alkyl,
24) $-(C_0-C_3)$-alkylene-O-$CH_2$-$CF_2$-$CF_2$-$CH_2$-O-$(C_0-C_3)$-alkyl,
25) $-(C_0-C_3)$-alkylene-O-$CH_2$-$(C_1-C_3)$-perfluoroalkylene-$CH_2$-OH,
26) $-SO_w-N(R^{11})-R^{13}$, wherein w is 1 or 2,
27) $-(C_0-C_4)$-alkylene-C(O)-N($R^{11}$)-$R^{13}$,
28) $-(C_0-C_4)$-alkylene-N($R^{11}$)-$R^{13}$, or
29) a residue from the following list

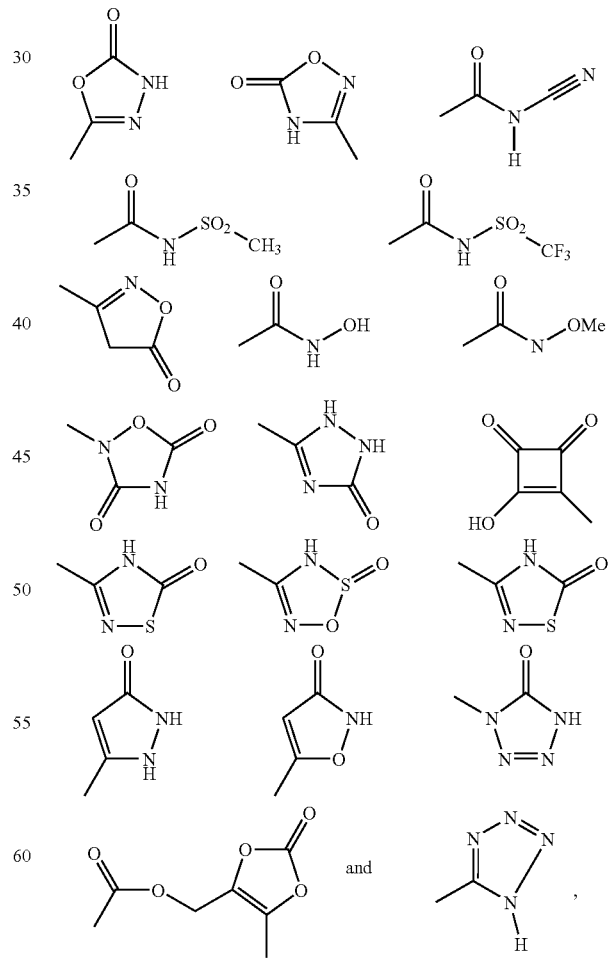

wherein Me is methyl, if two —OR19 residues are attached to adjacent atoms they can form together with the atoms which they are attached to a 1,3-dioxole ring or a 2,3-dihydro-[1,4]dioxine ring, which is substituted one, two, three or four times by R13, provided that R³ can be attached at any position on the ring of formulae I and II and can occur one, two or three times and is independently of one another identical or different, R11 and R12 are independently of one another identical or different and are
1) hydrogen atom,
2) —($C_1$–$C_6$)-alkyl, wherein alkyl is unsubstituted or mono-, di- or trisubstituted independently of one another by R13,
3) —($C_0$–$C_6$)-alkyl-($C_6$–$C_{14}$)-aryl, wherein aryl is as defined above and wherein alkyl and aryl are independently from one another unsubstituted or mono-, di- or trisubstituted by R13,
4) —O—$R^{17}$, or
5) —($C_0$–$C_6$)-alkyl-($C_4$–$C_{15}$)-heterocyclyl, wherein alkyl and heterocyclyl is as defined above and independently from one another are unsubstituted or mono-, di- or trisubstituted by R13, or R11 and R12 together with the nitrogen atom to which they are bonded can form a ring selected out of the group azepine, azetidine, 1,4-diazepane, dioxazole, dioxazine, 1,2-diazepine, 1,3-diazepine, 1,4-diazepine, imidazole, imidazoline, imidazolidine, isothiazole, isothiazolidine, isothiazoline, isoxazole, isoxazoline, isoxazolidine, 2-isoxazoline, ketopiperazine, morpholine, [1,4]oxazepane, oxazole, piperazine, piperidine, pyrazine, pyrazole, pyrazoline, pyrazolidine, pyridazine, pyridine, pyrimidine, pyrrole, pyrrolidine, pyrrolidinone, pyrroline, tetrahydropyridine, tetrazine, tetrazole, thiazole, thiadiazole, thiazolidine, thiazoline, thiomorpholine, 1,2,3-triazine, 1,2,4-triazine, 1,3,5-triazine, 1,2,3-triazole or 1,2,4-triazole, which is unsubstituted or mono-, di- or trisubstituted independently of one another by R13, R13 is fluorine, chlorine, bromine, iodine, —$NO_2$, —CN, =O, —OH, —$CF_3$, —C(O)—O—$R^{10}$, —C(O)—N($R^{10}$)—$R^{20}$, —N($R^{10}$)—$R^{20}$, —($C_0$–$C_3$)-alkylene-O—$R^{10}$, —Si—($CH_3$)$_3$, —N($R^{10}$)—S(O)$_2$—$R^{10}$, —S—$R^{10}$, —$SO_2$—$R^{10}$, —S(O)$_2$—N($R^{10}$)—$R^{20}$, —C(O)—$R^{10}$, —($C_1$–$C_8$)-alkyl,
—($C_1$–$C_8$)-alkoxy, phenyl, phenyloxy-, —O—$CF_3$, —($C_1$–$C_3$)-perfluoroalkyl, —($C_0$–$C_4$)-alkyl-C(O)—O—C(R15, R16)—O—C(O)—R17, —($C_1$–$C_4$)-alkoxy-phenyl, —($C_0$–$C_4$)-alkyl-C(O)—O—C(R15, R16)—O—C(O)—O—R17, —O—R15, —NH—C(O)—NH—$R^{10}$, —NH—C(O)—O—$R^{10}$, or a residue from the following list

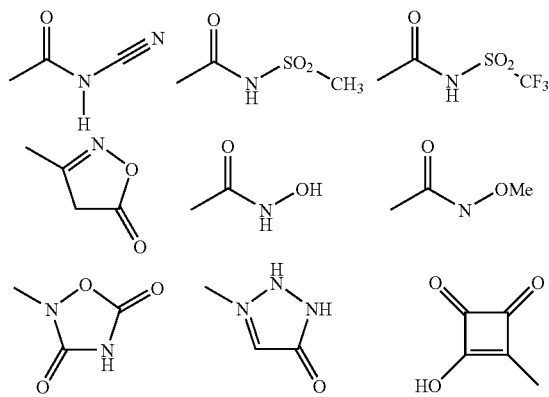

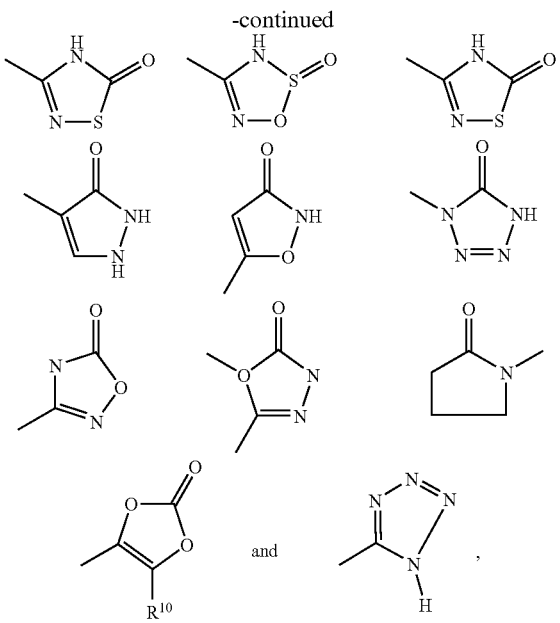

$R^{10}$ and $R^{20}$ are independently of one another hydrogen, —($C_1$–$C_6$)-alkyl, —($C_0$–$C_4$)-alkyl-OH —($C_0$–$C_4$)-alkyl-O—($C_1$–$C_4$)-akyl or —($C_1$–$C_3$)-perfluoroalkyl, R15 and R16 are independently of one another hydrogen, —($C_1$–$C_6$)-alkyl, or together form a ring out of the droup cyclopropyl, cyclobutyl, cyclopentyl or cyclohexyl, wherein each ring is unsubstituted or substituted one to three times by $R^{10}$, and R17 is —($C_1$–$C_6$)-alkyl, —($C_1$–$C_6$)-alkyl-OH, —($C_1$–$C_6$)-alkyl-O—($C_1$–$C_6$)-alkyl, —($C_3$–$C_8$)-cycloalkyl, —($C_1$–$C_6$)-alkyl-O—($C_1$–$C_8$)-alkyl-($C_3$–$C_8$)-cycloalkyl, —($C_1$–$C_6$)-alkyl-($C_3$–$C_8$)-cycloalkyl, wherein said cycloalkyl ring is unsubstituted or substituted one, two or three times by —OH, —O—($C_1$–$C_4$)-alkyl or $R^{10}$, in all its stereoisomeric forms and mixtures thereof in any ratio, and its physiologically tolerable salts.

5) The present invention also relates to the compounds of the formulae I and II, wherein J¹ is N or C, J² is N or C, J³ is N or C, J⁴ is N or C and J⁵ is N or C, provided that a) J¹ is N and J² is C and J³ is N, or
b) J⁴ is N and J⁵ is N, or
c) J⁴ is N and J⁵ is C, and R0 is 1) phenyl, wherein phenyl is unsubstituted or mono-, di- or trisubstituted independently of one another by R8,
2) a heterocyclyl out of the group benzimidazolyl, 1,3-benzodioxolyl, benzofuranyl, benzoxazolyl, benzothiazolyl, benzothiophenyl, cinnolinyl, chromanyl, indazolyl, indolyl, isochromanyl, isoindolyl, isoquinolinyl, phenylpyridyl, phthalazinyl, pteridinyl, purinyl, pyridyl, pyridoimidazolyl, pyridopyridinyl, pyridopyrimidinyl, pyrimidinyl, quinazolinyl, quinolyl, quinoxalinyl or 1,4,5,6-tetrahydro-pyridazinyl, wherein said heterocyclyl is unsubstituted or mono-, di- or trisubstituted independently of one another by R8, or
3) a heterocyclyl out of the group pyridyl, 2-pyridyl, 3-pyridyl, 4-pyridyl, pyrrolyl, 2-pyrrolyl, 3-pyrrolyl, furyl, 2-furyl, 3-furyl; thienyl, 2-thienyl, 3-thienyl, imidazolyl, pyrazolyl, oxazolyl, isoxazolyl, thiazolyl, thiadiazolyl, isothiazolyl, triazolyl, tetrazolyl, pyridazinyl and pyrazinyl, wherein said heterocyclyl is unsubstituted or mono-, di- or trisubstituted independently of one another by R8,
and in addition is substituted by a residue selected out of the group pyridyl, 2-pyridyl, 3-pyridyl, 4-pyridyl, pyrrolyl, 2-pyrrolyl, 3-pyrrolyl, furyl, 2-furyl, 3-furyl; thienyl, 2-thienyl, 3-thienyl, imidazolyl, pyrazolyl, oxazolyl, isoxazolyl, thiazolyl, thiadiazolyl, isothiazolyl, triazolyl, tetrazolyl, pyridazinyl and pyrazinyl, wherein said residue is unsubstituted or mono-, di- or trisubstituted independently of one another by R8

R8 is 1. F, Cl, Br or J,
   2. —C(O)—$NH_2$,
   3. —($C_1$–$C_4$)-alkyl, wherein alkyl is unsubstituted or mono-, di- or trisubstituted independently of one another by halogen, —OH or a methoxy residue, or
   4. —O—($C_1$–$C_4$)-alkyl, wherein alkyl is unsubstituted or mono-, di- or trisubstituted independently of one another by halogen or a methoxy residue,
provided that R8 is at least one halogen, —C(O)—$NH_2$ or —O—($C_1$–$C_8$)-alkyl residue, if R0 is a aryl or a heterocyclyl, which are as defined above, Q is a direct bond, —C(O)—; —$SO_2$— or —($C_1$–$C_6$)-alkylene, —($C_0$–$C_2$)-alkylene-C(O)—$NR^{10}$— or —($C_0$–$C_3$)-alkylene-C(O)—O—($C_0$–$C_2$)-alkylene, $R^1$ is hydrogen atom, —($C_1$–$C_2$)-alkyl, —($C_1$–$C_3$)-alkylene-C(O)—NH—R0, —($C_1$–$C_3$)-perfluoroalkylene, —($C_1$–$C_3$)-alkylene-C(O)—O—$R^{15}$, —($C_1$–$C_3$)-alkylene-S(O)$_2$—($C_1$–$C_3$)-alkyl or —($C_1$–$C_3$)-alkylene-S(O)$_2$—N($R^{4'}$)—$R^{5'}$, wherein $R^{4'}$ and $R^{5'}$ are independent of one another are identical or different and are hydrogen atom or —($C_1$–$C_4$)-alkyl, $R^2$ is a direct bond or —($C_1$–$C_2$)-alkylene, $R^1$—N—$R^2$—V can form a 4- to 7-membered cyclic group out of the group azetidine, azetidinone, piperidine, piperazine, pyridine, pyrimidine, pyrrolidine, pyrrolidinone, 1,2,3-triazine, 1,2,4-triazine, 1,3,5-triazine, 1,2,3-triazole, 1,2,4-triazole, tetrazine, tetrazole, 1,4-diazepane, 1,2-diazepine, 1,3-diazepine, 1,4-diazepine, azepine, ketopiperazine, 1,4-oxazepane, oxazole, isoxazole, isoxazolidine, 2-isoxazoline, morpholine, thiazole, isothiazole, thiadiazole or thiomorpholine, wherein said cyclic group is unsubstituted or mono-, di- or trisubstituted independently of one another by R14, R14 is
   fluorine, chlorine, —OH, =O, —($C_1$–$C_8$)-alkyl, —C(O)—OH, —CN, —$NH_2$, —C(O)—O—($C_1$–$C_4$)-alkyl —C(O)—NH—($C_1$–$C_8$)-alkyl, —C(O)—N—[($C_1$–$C_8$)-alkyl]$_2$, —C(O)—$NH_2$ or —N($R^{18}$)—$R^{21}$, wherein $R^{18}$ and $R^{21}$ are independently from each other hydrogen atom, —($C_1$–$C_3$)-perfluoroalkyl or —($C_1$–$C_4$)-alkyl, V is 1. a cyclic residue out of the group containing compounds which are derived from azaindole (1H-pyrrolopyridine), aziridine, azirine, azetidine, azetidinone, 1,4-diazepane, pyrrole, pyrrolidine, pyridonyl, imidazole, pyrazole, 1,2,3-triazole, 1,2,4-triazole, tetrazole, pyridine, pyrimidine, pyrazine, 1,2,3-triazine, 1,2,4-triazine, 1,3,5-triazine, tetrazine, tetrazole, azepine, diazirine, 1,2-diazepine, 1,3-diazepine, 1,4-diazepine, pyridazine, piperidine, piperazine, pyrrolidinone, ketopiperazine, furan, pyran, dioxole, 1,4-oxazepane, oxazole, isoxazole, 2-isoxazoline, isoxazolidine, morpholine, oxirane, oxaziridine, 1,3-dioxolene, 1,3-dioxolane, 1,2-oxazine, 1,3-oxazine, 1,4-oxazine, oxaziridine, thiophene, thiopyran, thietan, thiazole, isothiazole, isothiazoline, isothiazolidine, 1,2-oxathiolan, thiodiazole, thiopyran, 1,2-thiazine, 1,3-thiazole, 1,3-thiazine, 1,4-thiazine, thiadiazine or thiomorpholine,
   wherein said cyclic residue is unsubstituted or mono-, di- or trisubstituted independently of one another by R14, or
2. phenyl, wherein phenyl is unsubstituted or mono-, di- or trisubstituted independently of one another by R14, or G is a direct bond, —($CH_2$)$_m$—, or —($CH_2$)$_m$—$NR^{10}$—,
m is the integers zero, 1, 2, 3 or 4,
M is 1. a hydrogen atom,
   2. heterocyclyl, wherein heterocyclyl is a residue out of the group which can be derived from azepane, azepine, 1,4-diazepane, 1,2-diazepine, 1,3-diazepine, 1,4-diazepine, imidazole, isothiazole, isoxazole, isoxazolidine, 2-isoxazoline, ketomorpholine, ketopiperazine, morpholine, oxazole, [1,4]-oxazepane, piperazine, piperazinone, piperidine, piperidinone, pyrazine, pyridazine, pyridazinone, pyridine, pyridone, pyrimidine, pyrrolidine, pyrrolidinone, tetrahydropyran, 1,4,5,6-tetrahydro-pyridazinyl, tetrazine, tetrazole, thiadiazole, thiazole, thiomorpholine, thiophene, 1,2,3-triazine, 1,2,4-triazine, 1,3,5-triazine, 1,2,3-triazole or 1,2,4-triazole, wherein said heterocyclyl is unsubstituted or mono-, di- or trisubstituted independently of one another by R14,
   3. —($C_1$–$C_6$)-alkyl, wherein alkyl is unsubstituted or mono-, di- or trisubstituted independently of one another by R14, or
   4. ($C_3$–$C_6$)-cycloalkyl,
   5. —C(O)—N($R^{11}$)—$R^{12}$, $R^3$ is
1) hydrogen atom,
2) halogen,
3) —($C_1$–$C_4$)-alkyl, wherein alkyl is unsubstituted or mono-, di- or trisubstituted independently of one another by R13,
4) —($C_1$–$C_3$)-perfluoroalkyl,
5) phenyl, wherein phenyl is unsubstituted or mono-, di- or trisubstituted independently of one another by R13,
6) —($C_0$–$C_4$)-alkylene-O—R19, wherein R19 is
   a) hydrogen atom,
   b) —($C_1$–$C_4$)-alkyl, wherein alkyl is unsubstituted or mono-, di- or trisubstituted independently of one another by R13,
   c) phenyl, wherein phenyl is unsubstituted or mono-, di- or trisubstituted independently of one another by R13,
   d) —$CF_3$ or
   e) $CHF_2$,
7) —CN,
8) —$NR^{10}$—$SO_2$—$R^{10}$,
9) —$SO_S$—$R^{11}$, wherein s is 1 or 2,
10) —$SO_t$—N($R^{11}$)—$R^{12}$, wherein t is 1 or 2,
11) —($C_0$–$C_4$)-alkylene-C(O)—$R^{11}$,
12) —($C_0$–$C_4$)-alkylene-C(O)—O—$R^{11}$,
13) —($C_0$–$C_4$)-alkylene-C(O)—N($R^{11}$)—$R^{12}$,
14) —($C_0$–$C_4$)-alkylene-N($R^{11}$)—$R^{12}$,
15) —($C_0$–$C_2$)alkylene-C(O)—O—($C_2$–$C_4$)-alkylene-O—C(O)—($C_1$–$C_4$)-alkyl,
16) —C(O)—O—C(R15, R16)—O—C(O)—R17,
17) —($C_0$–$C_2$)alkylene-C(O)—O—($C_2$–$C_4$)-alkylene-O—C(O)—O—($C_1$–$C_6$)-alkyl
18) —C(O)—O—C(R15, R16)—O—C(O)—O—R17,
19) —($C_0$–$C_4$)-alkylene-($C_3$–$C_6$)-cycloalkyl, wherein cycloalkyl is unsubstituted or mono-, di- or trisubstituted independently of one another by R13, 20) —($C_0$–$C_3$)-alkylene-O—$CH_2$—$CF_2$—$CH_2$—O—($C_0$–$C_3$)-alkyl,
21) —($C_0$–$C_3$)-alkylene-O—$CH_2$—$CF_2$—$CF_2$—$CH_2$—O—($C_0$–$C_3$)-alkyl,
22) —($C_0$–$C_3$)-alkylene-O—$CH_2$—($C_1$–$C_3$)-perfluoroalkylene-$CH_2$—OH,
23) —$SO_w$—$N(R^{11})$—$R^{13}$, wherein w is 1 or 2,
24) —($C_0$–$C_4$)-alkylene-C(O)—$N(R^{11})$—$R^{13}$,
25) —($C_0$–$C_4$)-alkylene-$N(R^{11})$—$R^{13}$, or
26) a residue from the following list

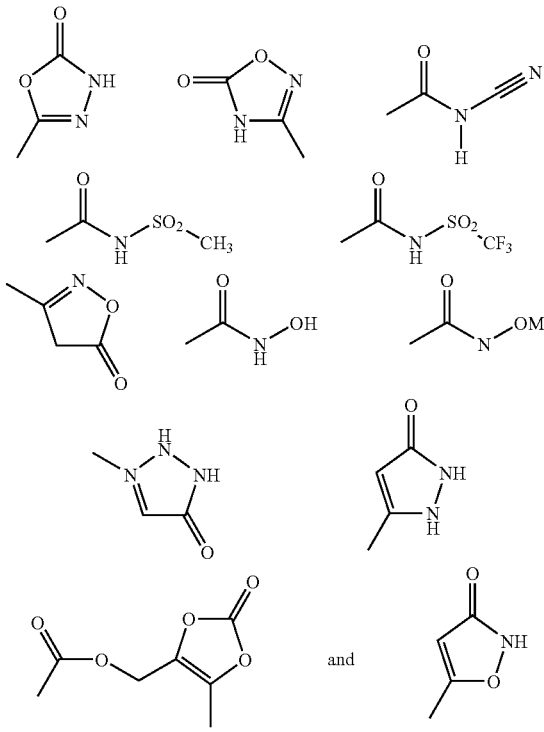

wherein Me is methyl,
if two —OR19 residues are attached to adjacent atoms they can form together with the atoms which they are attached to a 1,3-dioxole ring or a 2,3-dihydro-[1,4]dioxine ring, which is substituted one, two, three or four times by R13,
provided that $R^3$ can be attached at any position on the ring of formulae I and II,
$R^{11}$ and $R^{12}$ together with the nitrogen atom to which they are bonded can form a ring selected out of the group azepine, azetidine, 1,4-diazepane, dioxazole, dioxazine, 1,2-diazepine, 1,3-diazepine, 1,4-diazepine, imidazole, imidazoline, imidazolidine, isothiazole, isothiazolidine, isothiazoline, isoxazole, isoxazoline, isoxazolidine, 2-isoxazoline, ketopiperazine, morpholine, [1,4]-oxazepane, oxazole, piperazine, piperidine, pyrazine, pyrazole, pyrazoline, pyrazolidine, pyridazine, pyridine, pyrimidine, pyrrole, pyrrolidine, pyrrolidinone, pyrroline, tetrahydropyridine, tetrazine, tetrazole, thiazole, thiadiazole, thiazolidine, thiazoline, thiomorpholine, thiophene, 1,2,3-triazine, 1,2,4-triazine, 1,3,5-triazine, 1,2,3-triazole or 1,2,4-triazole, wherein said ring is unsubstituted or mono-, di- or trisubstituted independently of one another by R13,
R13 is fluorine, chlorine, —$NO_2$, —CN, =O, —OH, —$CF_3$, —C(O)—O—$R^{10}$, —C(O)—$N(R^{10})$—$R^{20}$, —$N(R^{10})$—$R^{20}$, —($C_0$–$C_3$)-alkylene-O—$R^{10}$, —Si—$(CH_3)_3$, —$N(R^{10})$—$S(O)_2$—$R^{10}$, —S—$R^{10}$, —$SO_2$—$R^{10}$, —$S(O)_2$—$N(R^{10})$—$R^{20}$, —C(O)—$R^{10}$, —($C_1$–$C_8$)-alkyl, —($C_1$–$C_8$)-alkoxy, phenyl, phenyloxy-, —O—$CF_3$, —($C_1$–$C_3$)-perfluoroalkyl, —NH—C(O)—NH—$R^{10}$, —($C_0$–$C_4$)-alkyl-C(O)—O—C(R15, R16)—O—C(O)—R17, —($C_1$–$C_4$)-alkoxy-phenyl, —($C_0$–$C_4$)-alkyl-C(O)—O—C(R15, R16)—O—C(O)—O—R17, —O—R15, —NH—C(O)—O—$R^{10}$, or a residue from the following list

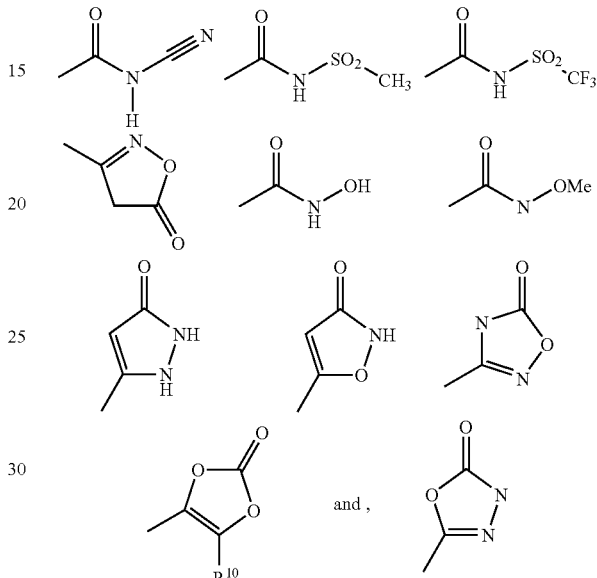

wherein Me is methyl,
$R^{10}$ and $R^{20}$ are independently of one another hydrogen, —($C_1$–$C_6$)-alkyl, —($C_0$–$C_4$)-alkyl-OH, —($C_0$–$C_4$)-alkyl-O—($C_1$–$C_4$)-akyl or —($C_1$–$C_3$)-perfluoroalkyl,
R15 and R16 are independently of one another hydrogen, —($C_1$–$C_6$)-alkyl, or together form a ring out of the droup cyclopropyl, cyclobutyl, cyclopentyl or cyclohexyl, wherein each ring is unsubstituted or substituted one to three times by $R^{10}$, and
R17 is —($C_1$–$C_6$)-alkyl, —($C_1$–$C_6$)-alkyl-OH, —($C_1$–$C_6$)-alkyl-O—($C_1$–$C_6$)-alkyl, —($C_3$–$C_8$)-cycloalkyl —($C_1$–$C_6$)-alkyl-O—($C_1$–$C_8$)-alkyl-($C_3$–$C_8$)-cycloalkyl, —($C_1$–$C_6$)-alkyl-($C_3$–$C_8$)-cycloalkyl, wherein said cycloalkyl ring is unsubstituted or substituted one, two or three times by —OH, —O—($C_1$–$C_4$)-alkyl or $R^{10}$, in all its stereoisomeric forms and mixtures thereof in any ratio, and its physiologically tolerable salts.
6) The present invention also relates to the compounds of the formulae I and II, wherein $J^1$ is N or C, $J^2$ is N or C, $J^3$ is N or C, $J^4$ is N or C and $J^5$ is N or C,
provided that a) $J^1$ is N and $J^2$ is C and $J^3$ is N, or
b) $J^4$ is N and $J^5$ is N, or
c) $J^4$ is N and $J^5$ is C, and
R0 is 1) phenyl, wherein phenyl is unsubstituted or mono-, di- or trisubstituted independently of one another by R8,
2) a heterocyclyl selected out of the group indolyl, isoindolyl, benzofuranyl, benzothiophenyl, 1,3-benzodioxolyl, indazolyl, benzimidazolyl, benzoxazolyl, benzothiazolyl, quinolinyl, isoquinolinyl, chromanyl, isochromanyl, cinnolinyl, quinazolinyl, quinoxalinyl, phthalazinyl, pyridoimidazolyl, pyridopyridinyl, pyridopyrimidinyl, pyridyl, purinyl and pteridinyl,
wherein said heterocyclyl is unsubstituted or mono-, di- or trisubstituted independently of one another by R8,
3) a heterocyclyl out of the group pyridyl, 2-pyridyl, 3-pyridyl, 4-pyridyl, pyrrolyl, 2-pyrrolyl, 3-pyrrolyl, furyl, 2-furyl, 3-furyl; thienyl, 2-thienyl, 3-thienyl, imidazolyl, pyrazolyl, oxazolyl, isoxazolyl, thiazolyl, thiadiazolyl, isothiazolyl, triazolyl, tetrazolyl, pyridazinyl and pyrazinyl, wherein said heterocyclyl is unsubstituted or mono-, di- or trisubstituted independently of one another by R8,
and in addition is substituted by a residue selected out of the group pyridyl, 2-pyridyl, 3-pyridyl, 4-pyridyl, pyrrolyl, 2-pyrrolyl, 3-pyrrolyl, furyl, 2-furyl, 3-furyl; thienyl, 2-thienyl, 3-thienyl, imidazolyl, pyrazolyl, oxazolyl, isoxazolyl, thiazolyl, thiadiazolyl, isothiazolyl, triazolyl, tetrazolyl, pyridazinyl and pyrazinyl, wherein said residue is unsubstituted or mono-, di- or trisubstituted independently of one another by R8

R8 is 1. is F, Cl, Br, J,
2. —C(O)—$NH_2$,
3. —($C_1$–$C_4$)-alkyl, wherein alkyl is unsubstituted or mono-, di- or trisubstituted independently of one another by halogen, —OH or a methoxy residue, or
4. —O—($C_1$–$C_4$)-alkyl, wherein alkyl is unsubstituted or mono-, di- or trisubstituted independently of one another by halogen or a methoxy residue, provided that R8 is at least one halogen, —C(O)—$NH_2$ or —O—($C_1$–$C_8$)-alkyl residue, if R0 is a aryl or a heterocyclyl, which are as defined above, Q is a direct bond, —C(O)—; —$SO_2$—, —C(O)—O-methylene, —($C_1$–$C_6$)-alkylene or —($C_0$–$C_2$)-alkylene-C(O)—$NR^{10}$, $R^1$ is hydrogen atom or —($C_1$–$C_2$)-alkyl, $R^2$ is a direct bond or —($C_1$–$C_2$)-alkylene, or $R^1$—N—$R^2$—V can form a 4- to 7-membered cyclic group out of the group piperidine, piperazine, pyridine, pyrimidine, pyrrolidine, pyrrolidinone, 1,2,3-triazine, 1,2,4-triazine, 1,3,5-triazine, 1,2,3-triazole, 1,2,4-triazole, tetrazine, tetrazole, 1,2-diazepine, 1,3-diazepine, 1,4-diazepine, azepine, ketopiperazine, oxazole, isoxazole, isoxazolidine, 2-isoxazoline, morpholine, thiazole, isothiazole, thiadiazole or thiomorpholine, wherein said cyclic group is unsubstituted or mono-, di- or trisubstituted independently of one another by R14, R14 is fluoro, chlorine, —($C_1$–$C_4$)-alkyl or —$NH_2$, V is 1. a cyclic residue out of the group containing compounds, which are derived from azaindolyl(1H-pyrrolopyridyl), azetidine, azepine, aziridine, azirine, 1,4-diazepane, 1,2-diazepine, 1,3-diazepine, 1,4-diazepine, diazirine, 1,3-dioxolane, dioxazole, furan, imidazole, isoquinoline, isothiazole, isothiazolidine, isothiazoline, isoxazole, 2-isoxazoline, isoxazolidine, ketopiperazine, morpholine, 1,2-oxazine, 1,3-oxazine, 1,4-oxazine, oxazole, 1,2-oxathiolan, piperidine, pyran, pyrazine, pyrazole, pyridazine, piperazine, pyridine, pyridone, pyrimidine, pyrrole, pyrrolidine, pyrrolidinone, quinazoline, quinoline, tetrazine, tetrazole, thiadiazine, 1,2-thiazine, 1,3-thiazine, 1,4-thiazine, 1,3-thiazine, thietan, thiomorpholine, thiophene, thiopyran, 1,2,3-triazine, 1,2,4-triazine, 1,3,5-triazine, 1,2,3-triazole or 1,2,4-triazole,
wherein said cyclic residue is unsubstituted or mono-, di- or trisubstituted independently of one another by R14, or 2. phenyl, wherein phenyl is unsubstituted or mono-, di- or trisubstituted independently of one another by R14, G is a direct bond, —$(CH_2)_m$—, or —$(CH_2)_m$—$NR^{10}$—, m is the integers zero, 1, 2, 3 or 4, M is 1. a hydrogen atom,
2. heterocyclyl, wherein heterocyclyl is a residue out of the group which can be derived from 1,4-diazepane, ketomorpholine, thiophene, pyridazone, piperidine, piperazine, pyridine, pyrimidine, pyrrolidine, pyrrolidinone, pyridonyl, imidazole, pyridazine, pyrazine, 1,2,3-triazine, 1,2,4-triazine, 1,3,5-triazine, 1,2,3-triazole, 1,2,4-triazole, tetrazine, tetrazole, 1,2-diazepine, 1,3-diazepine, 1,4-diazepine, azepine, ketopiperazine, oxazole, isoxazole, isoxazolidine, 2-isoxazoline, morpholine, thiazole, isothiazole, tetrahydropyran, 1,4,5,6-tetrahydro-pyridazinyl, thiadiazole or thiomorpholine, wherein said heterocyclyl is unsubstituted or mono-, di- or trisubstituted independently of one another by R14,
3. —($C_1$–$C_6$)-alkyl, wherein alkyl is unsubstituted or mono-, di- or trisubstituted independently of one another by R14, or
4. ($C_3$–$C_6$)-cycloalkyl, $R^3$ is 1) hydrogen atom,
2) halogen,
3) —($C_1$–$C_4$)-alkyl, wherein alkyl is unsubstituted or mono-, di- or trisubstituted independently of one another by R13,
4) —($C_1$–$C_3$)-perfluoroalkyl,
5) phenyl, wherein phenyl is unsubstituted or mono-, di- or trisubstituted independently of one another by R13,
6) —($C_0$–$C_4$)-alkylene-O—R19, wherein R19 is
   a) hydrogen atom,
   b) —($C_1$–$C_4$)-alkyl, wherein alkyl is unsubstituted or mono-, di- or trisubstituted independently of one another by R13,
   c) phenyl, wherein phenyl is unsubstituted or mono-, di- or trisubstituted independently of one another by R13,
   d) —$CF_3$ or
   e) —$CHF_2$,
7) —CN,
8) —$NR^{10}$—$SO_2$—$R^{10}$,
9) —$SO_S$—$R^{11}$, wherein s is 1 or 2,
10) —$SO_t$—$N(R^{11})$—$R^{12}$, wherein t is 1 or 2,
11) —($C_0$–$C_4$)-alkylene-C(O)—$R^{11}$,
12) —($C_0$–$C_4$)-alkylene-C(O)—O—$R^{11}$,
13) —($C_0$–$C_4$)-alkylene-C(O)—$N(R^{11})$—$R^{12}$,
14) —($C_0$–$C_4$)-alkylene-$N(R^{11})$—$R^{12}$,
15) —($C_0$–$C_2$)alkylene-C(O)—O—($C_2$–$C_4$)-alkylene-O—C(O)—($C_1$–$C_4$)-alkyl,
16) —C(O)—O—C(R15, R16)—O—C(O)—R17,
17) —($C_0$–$C_2$)alkylene-C(O)—O—($C_2$–$C_4$)-alkylene-O—C(O)—O—($C_1$–$C_6$)-alkyl
18) —C(O)—O—C(R15, R16)—O—C(O)—O—R17,
19) —($C_0$–$C_3$)-alkylene-($C_3$–$C_6$)-cycloalkyl, wherein cycloalkyl is unsubstituted or mono-, di- or trisubstituted independently of one another by R13,
20) —($C_0$–$C_4$)-alkylene-($C_4$–$C_{15}$)-heterocyclyl, wherein heterocyclyl is a residue out of the group which can be derived from pyridin, furan, thiazole or thiophen and is unsubstituted or mono-, di- or trisubstituted independently of one another by R13,
21) —($C_0$–$C_3$)-alkylene-O—$CH_2$—$CF_2$—$CH_2$—O—($C_0$–$C_3$)-alkyl,
22) —($C_0$–$C_3$)-alkylene-O—$CH_2$—$CF_2$—$CF_2$—$CH_2$—O—($C_0$–$C_3$)-alkyl 23) —(C$_0$–C$_3$)-alkylene-O—CH$_2$—(C$_1$–C$_3$)-perfluoro-alkylene-CH$_2$—OH,
24) —SO$_w$—N(R$^{11}$)—R$^{13}$, wherein w is 1 or 2,
25) —(C$_0$–C$_4$)-alkylene-C(O)—N(R$^{11}$)—R$^{13}$,
26) —(C$_0$–C$_4$)-alkylene-N(R$^{11}$)—R$^{13}$, or
27) a residue from the following list

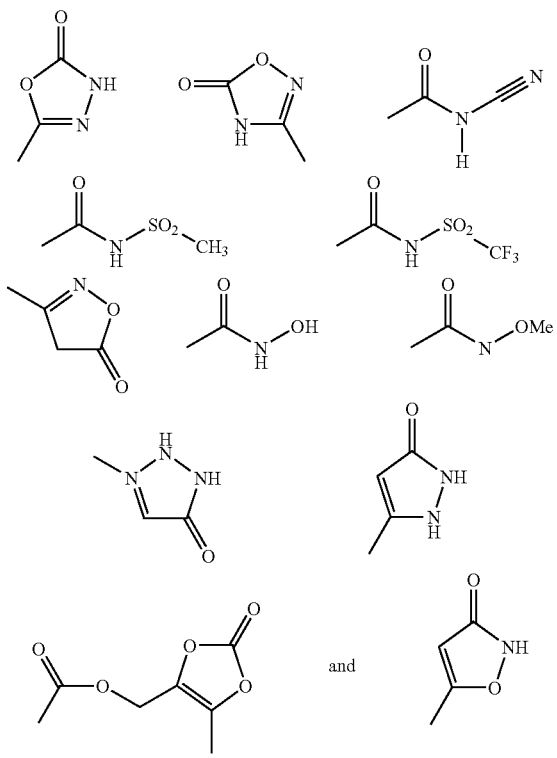

wherein Me is methyl,
provided that R$^3$ can be attached at any position on the ring of formulae I and II
R11 and R12 are independently of one another identical or different and are
1) hydrogen atom,
2) —(C$_1$–C$_4$)-alkyl, wherein alkyl is unsubstituted or mono-, di- or trisubstituted independently of one another by R13,
3) —(C$_0$–C$_6$)-alkyl-(C$_3$–C$_6$)-cycloalkyl,
4) —O—R$^{17}$, or
5) —(C$_0$–C$_6$)-alkyl-(C$_4$–C$_{15}$)-heterocyclyl, wherein alkyl and heterocyclyl independently from one another are unsubstituted or mono-, di- or trisubstituted by R13 and wherein heterocyclyl is selected out of the group azetidine, cyclopropyl, cyclobutyl, 4,5-dihydro-oxazol, imidazolidine, morpholine, (1,4)-oxazepane, oxazolidine, piperidine, piperazine, pyrrolidine, tetrahydrothiophene, thiazolidine or thiomorpholine, or
R11 and R12 together with the nitrogen atom to which they are bonded form a heterocyclic ring, which is selected out of the group azetidine, cyclopropyl, cyclobutyl, 4,5-dihydro-oxazole, imidazolidine, morpholine, (1,4)-oxazepane, oxazolidine, piperidine, piperazine, pyrrolidine, tetrahydrothiophene, thiazolidine or thiomorpholine, wherein said ring is unsubstituted or mono-, di- or trisubstituted independently of one another by R13,
R13 is fluorine, —CN, =O, —OH, —CF$_3$, —C(O)—O—R$^{10}$, —C(O)—N(R$^{10}$)—R$^{20}$, —N(R$^{10}$)—(C$_3$–C$_6$)-cy-cloalkyl, —(C$_0$–C$_3$)-alkylene-O—R$^{10}$, —Si—(CH$_3$)$_3$, —S—R$^{10}$, —SO$_2$—R$^{10}$, —S(O)$_2$—N(R$^{10}$)—R$^{20}$, —(C$_1$–C$_3$)-perfluoroalkyl, or a residue from the following list

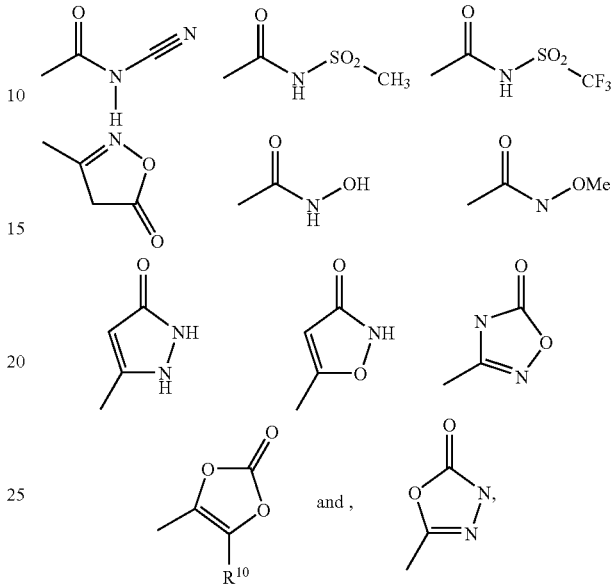

wherein Me is methyl,
R$^{10}$ and R$^{20}$ are independently of one another hydrogen, —(C$_1$–C$_4$)-alkyl or —(C$_1$–C$_3$)-perfluoroalkyl,
R$^{15}$ and R$^{16}$ are independently of one another hydrogen, —(C$_1$–C$_4$)-alkyl, or together form a ring out of the droup cyclopropyl, cyclobutyl, cyclopentyl or cyclohexyl, wherein each ring is unsubstituted or substituted one to three times by R$^{10}$, and
R$^{17}$ is —(C$_1$–C$_6$)-alkyl, —(C$_1$–C$_6$)-alkyl-OH, —(C$_1$–C$_6$)-alkyl-O—(C$_1$–(C$_1$–C$_6$)-alkyl-O—(C$_1$–C$_8$)-alkyl-(C$_3$–C$_8$)-cycloalkyl, —(C$_1$–C$_6$)-alkyl-(C$_3$–C$_8$)-cy-cloalkyl, wherein said cycloalkyl ring is unsubstituted or substituted one, two or three times by —OH, —O—(C$_1$–C$_4$)-alkyl or R$^{10}$,
in all its stereoisomeric forms and mixtures thereof in any ratio, and its physiologically tolerable salts.

7) The present invention also relates to the compounds of the formulae I and II, wherein J$^1$ is N or C, J$^2$ is N or C, J$^3$ is N or C, J$^4$ is N or C and J$^5$ is N or C,
provided that a) J$^1$ is N and J$^2$ is C and J$^3$ is N, or
b) J$^4$ is N and J$^5$ is N, or
c) J$^4$ is N and J$^5$ is C, and
R0 is 1) phenyl, wherein phenyl is unsubstituted or mono- or disubstituted independently of one another by R8,
2) heterocyclyl selected out of the goup benzothiazolyl, benzothiophenyl or pyridyl, wherein heterocyclyl is unsubstituted or mono- or disubstituted independently of one another by R8, or
3) a heterocyclyl out of the group thienyl, thiadiazolyl, isoxazolyl and thiazolyl, wherein said heterocyclyl is substituted by a residue selected out of the group thienyl, 2-thienyl and 3-thienyl, wherein said residue is unsubstituted or mono- or disubstituted independently of one another by R8,
R8 is F, Cl, Br, —OCH$_3$, —C(O)—NH$_2$ or —O—CF$_3$, Q is a direct bond, —C(O)—; —SO$_2$—, —CH$_2$—C(O)—NH—, methylene or ethylene,
R$^1$ is hydrogen atom,
R$^2$ is a direct bond or methylene,
R$^1$—N—R$^2$—V can form a 4- to 8-membered cyclic group out of the group azetidine, pyrrolidine, piperidine and piperazine,
R14 is fluorine, chlorine, methyl, ethyl or —NH$_2$,
V is 1. a residue out of the group containing compounds which is derived from azaindolyl(1H-pyrrolopyridyl), azetidine, 1,4-diazepane, isoxazole, isoquinoline, piperazine, piperidine, pyrazine, pyridazine, pyrimidine, pyrrolidine, quinazoline, quinoline or tetrahydropyrane, wherein said cyclic residue is unsubstituted or mono- or disubstituted independently of one another by R14, or
2. phenyl, wherein phenyl is unsubstituted or mono- or disubstituted independently of one another by R14,
G is a direct bond, —(CH$_2$)$_m$—, or —(CH$_2$)$_m$—NR$^{10}$—,
m is the integers zero, 1 or 2,
M is a hydrogen atom, (C$_2$–C$_4$)-alkyl, azepanyl, cyclopropyl, cyclobutyl, cyclopentyl, cyclohexyl, imidazolyl, ketomorpholinyl, morpholinyl, [1,4]Oxazepanyl, piperidinyl, piperidonyl, pyrazinyl, pyrazolyl, pyridazinyl, pyridyl, pyrimidyl, pyrrolidinyl, 1,4,5,6-tetrahydro-pyridazinyl, or tetrahydropyranyl, wherein the residues are unsubstituted or mono- or disubstituted independently of one another by R14
R$^3$ is
1) hydrogen atom,
2) fluorine, chlorine, bromine, iodine,
3) —(C$_1$–C$_4$)-alkyl, wherein alkyl is unsubstituted or mono-, di- or trisubstituted independently of one another by R13,
4) —(C$_1$–C$_3$)-perfluoroalkyl,
5) phenyl, wherein phenyl is unsubstituted or mono-, di- or trisubstituted independently of one another by R13,
6) —(C$_0$–C$_2$)-alkylene-O—R19, wherein R19 is
  a) hydrogen atom,
  b) —(C$_1$–C$_4$)-alkyl, wherein alkyl is unsubstituted or mono-, di- or trisubstituted independently of one another by R13,
  c) phenyl, wherein phenyl is unsubstituted or mono-, di- or trisubstituted independently of one another by R13,
  d) —CF$_3$ or
  e) —CHF$_2$
7) —CN,
8) —NR$^{10}$—SO$_2$—R$^{10}$,
9) —SO$_S$—R$^{11}$, wherein s is 1 or 2,
10) —SO$_t$—N(R$^{11}$)—R$^{12}$, wherein t is 1 or 2,
11) —(C$_0$–C$_4$)-alkylene-C(O)—R$^{11}$,
12) —(C$_0$–C$_4$)-alkylene-C(O)—O—R$^{11}$,
13) —(C$_0$–C$_4$)-alkylene-C(O)—N(R$^{11}$)—R$^{12}$,
14) —(C$_0$–C$_4$)-alkylene-N(R$^{11}$)—R$^{12}$,
15) —(C$_0$–C$_2$)alkylene-C(O)—O—(C$_2$–C$_4$)-alkylene-O—C(O)—(C$_1$–C$_4$)-alkyl,
16) —C(O)—O—C(R15, R16)—O—C(O)—R17,
17) C$_0$–C$_2$)alkylene-C(O)—O—(C$_2$–C$_4$)-alkylene-O—C(O)—O—(C$_1$–C$_6$)-alkyl,
18) —C(O)—O—C(R15, R16)—O—C(O)—O—R17,
19) —(C$_0$–C$_3$)-alkylene-(C$_3$–C$_6$)-cycloalkyl, wherein cycloalkyl is unsubstituted or mono-, di- or trisubstituted independently of one another by R13,
20) —(C$_0$–C$_6$)-alkyl-heterocyclyl, wherein alkyl and heterocyclyl independently from one another are unsubstituted or mono-, di- or trisubstituted by R13 and wherein heterocyclyl is selected out of the group pyrroly, pyridyl, furanyl or thien, or
21) a residue from the following list

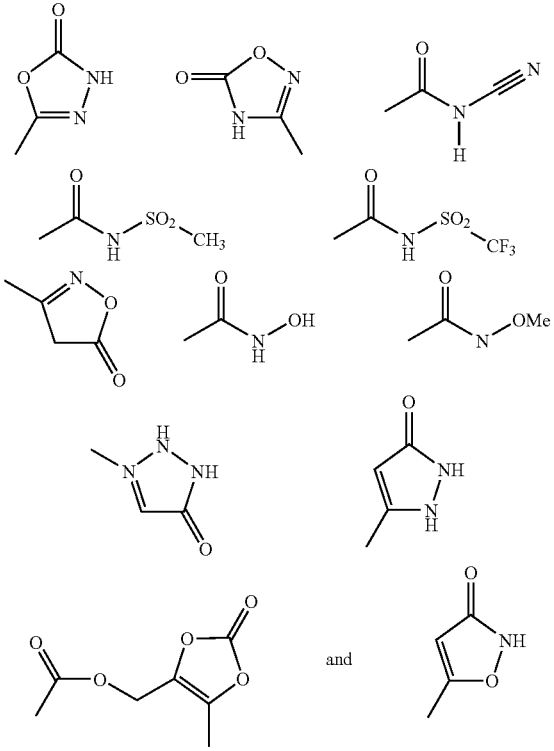

wherein Me is methyl,
provided that R$^3$ can be attached at any position on the ring of formulae I and II,
R11 and R12 are independently of one another identical or different and are
1) hydrogen atom,
2) —(C$_1$–C$_4$)-alkyl, wherein alkyl is unsubstituted or mono-, di- or trisubstituted independently of one another by R13,
3) —(C$_0$–C$_6$)-alkyl-(C$_3$–C$_6$)-cycloalkyl,
4) —O—R$^{17}$, or
5) —(C$_0$–C$_6$)-alkyl-heterocyclyl, wherein alkyl and heterocyclyl independently from one another are unsubstituted or mono-, di- or trisubstituted by R13 and wherein heterocyclyl is selected out of the group azetidine, 4,5-dihydrooxazol, imidazolidine, morpholine, (1,4)-oxazepane, pyrrolidine or tetrahydrothiophen, or
R11 and R12 together with the nitrogen atom to which they are bonded can form a ring, which is selected out of the group azetidine, imidazolidine, morpholine, (1,4)-oxazepane, oxazolidine, piperazine, piperidine, pyrrolidine, tetrahydrothiazol, thiazolidine or thiomorpholine, wherein said ring is unsubstituted or mono- or disubstituted independently of one another by R13,
R13 is fluorine, chlorine, —CN, =O, —OH, —CF$_3$, —C(O)—O—R$^{10}$, —C(O)—N(R$^{10}$)—R$^{20}$, —N(R$^{10}$)—R$^{20}$, —(C$_3$–C$_6$)-cycloalkyl, —(C$_0$–C$_3$)-alkylene-O—R$^{10}$, —Si—(CH$_3$)$_3$, —S—R$^{10}$, —SO$_2$—R$^{10}$, —(C$_1$–C$_4$)-alkyl, —(C$_1$–C$_3$)-perfluoroalkyl, —S(O)$_2$—N(R$^{10}$)—R$^{20}$, or a residue from the following list

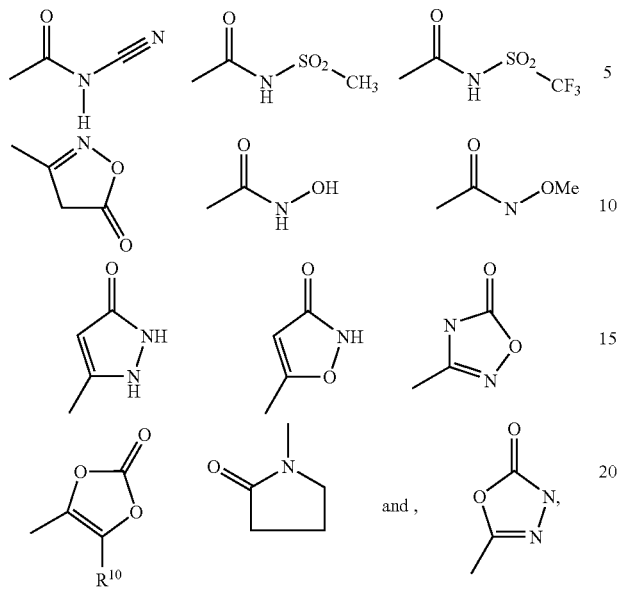

wherein Me is methyl, $R^{10}$ and $R^{20}$ are independently of one another hydrogen, —$(C_1$–$C_4)$-alkyl or —$(C_1$–$C_3)$-perfluoroalkyl, $R^{15}$ and $R^{16}$ are independently of one another hydrogen, —$(C_1$–$C_4)$-alkyl, or together form a ring out of the droup cyclopropyl, cyclobutyl, cyclopentyl or cyclohexyl, wherein each ring is unsubstituted or substituted one to three times by $R^{10}$, and R17 is —$(C_1$–$C_6)$-alkyl, —$(C_1$–$C_6)$-alkyl-OH, —$(C_1$–$C_6)$-alkyl-O—$(C_1$–$C_6)$-alkyl, —$(C_3$–$C_8)$-cycloalkyl, —$(C_1$–$C_6)$-alkyl-O—$(C_1$–$C_8)$-alkyl-$(C_3$–$C_8)$-cycloalkyl, —$(C_1$–$C_6)$-alkyl-$(C_3$–$C_8)$-cycloalkyl, wherein said cycloalkyl ring is unsubstituted or substituted one, two or three times by —OH, —O—$(C_1$–$C_4)$-alkyl or $R^{10}$, in all its stereoisomeric forms and mixtures thereof in any ratio, and its physiologically tolerable salts.

The present invention also relates to the compounds of the formula Ia,

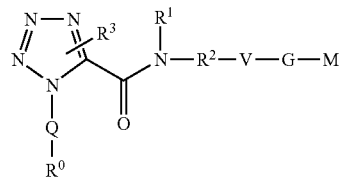

(Ia)

wherein $R^0$; $R^1$; $R^2$; $R^3$; Q; V, G and M have the meanings indicated in formulae I and II.

The present invention also relates to the compounds of the formula Ib,

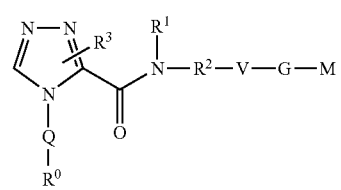

(Ib)

wherein $R^0$; $R^1$; $R^2$; $R^3$; Q; V, G and M have the meanings indicated in formulae I and II.

The present invention also relates to the compounds of the formula Ic,

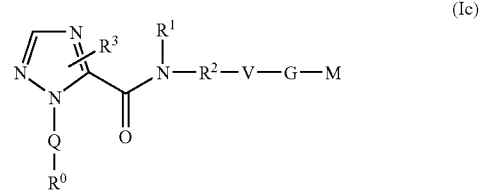

(Ic)

wherein $R^0$; $R^1$; $R^2$; $R^3$; Q; V, G and M have the meanings indicated in formulae I and II.

The present invention also relates to the compounds of the formula Id,

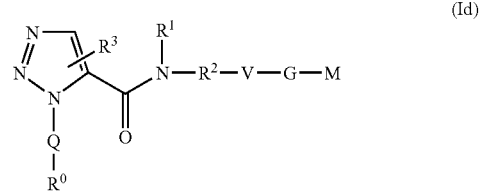

(Id)

wherein $R^0$; $R^1$; $R^2$; $R^3$; Q; V, G and M have the meanings indicated in formulae I and II.

The present invention also relates to the compounds of the formula IIa,

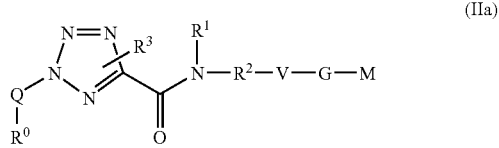

(IIa)

wherein $R^0$; $R^1$; $R^2$; $R^3$; Q; V, G and M have the meanings indicated in formulae I and II.

The present invention also relates to the compounds of the formula IIb,

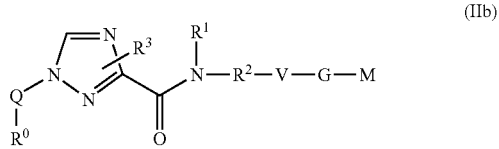

(IIb)

wherein $R^0$; $R^1$; $R^2$; $R^3$; Q; V, G and M have the meanings indicated in formulae I and II.

The present invention also relates to the compounds of the formula IIc,

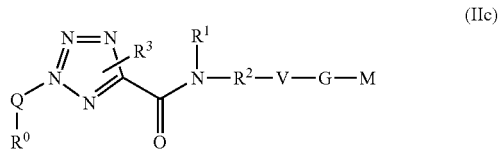

(IIc)

wherein $R^0$; $R^1$; $R^2$; $R^3$; Q; V, G and M have the meanings indicated in formulae I and II.

DETAILED DESCRIPTION OF THE INVENTION

The present invention also relates to the compounds of formula I, which are
1-[5-(5-Chloro-thiophen-2-yl)-isoxazol-3-ylmethyl]-5-pyrrol-1-yl-1H-[1,2,4]triazole-3-carboxylic acid (1-isopropyl-piperidin-4-yl)-amide;
1-[5-(5-Chloro-thiophen-2-yl)-isoxazol-3-ylmethyl]-5-pyridin-2-yl-1H-[1,2,4]triazole-3-carboxylic acid (1-isopropyl-piperidin-4-yl)-amide;
2-[5-(5-Chloro-thiophen-2-yl)-isoxazol-3-ylmethyl]-5-pyridin-2-yl-2H-[1,2,4]triazole-3-carboxylic acid (1-isopropyl-piperidin-4-yl)-amide;
1-[5-(5-Chloro-thiophen-2-yl)-isoxazol-3-ylmethyl]-5-phenyl-1H-[1,2,4]triazole-3-carboxylic acid (1-isopropyl-piperidin-4-yl)-amide; or
2-[5-(5-Chloro-thiophen-2-yl)-isoxazol-3-ylmethyl]-2H-tetrazole-5-carboxylic acid (1-isopropyl-piperdin-4-yl)-amide.

Definition of Terms

As used above, and throughout the description of the invention, the following terms, unless otherwise indicated, shall be understood to have the following meanings.

The term alkyl is to be understood in the broadest sense to mean hydrocarbon residues which can be linear, i.e. straight-chain, or branched and which can be acyclic or cyclic residues or comprise any combination of acyclic and cyclic subunits. Further, the term alkyl as used herein expressly includes saturated groups as well as unsaturated groups which latter groups contain one or more, for example one, two or three, double bonds and/or triple bonds, provided that the double bonds are not located within a cyclic alkyl group in such a manner that an aromatic system results. All these statements also apply if an alkyl group occurs as a substituent on another residue, for example in an alkyloxy residue, an alkyloxycarbonyl residue or an arylalkyl residue. Examples of "—$(C_1$–$C_8)$-alkyl" or "—$(C_1$–$C_8)$-alkylene" are alkyl residues containing 1, 2, 3, 4, 5, 6, 7 or 8 carbon atoms are methyl, methylene, ethyl, ethylene, propyl, propylene, butyl, butylene, pentyl, pentylene, hexyl, heptyl or octyl, the n-isomers of all these residues, isopropyl, isobutyl, 1-methylbutyl, isopentyl, neopentyl, 2,2-dimethylbutyl, 2-methylpentyl, 3-methylpentyl, isohexyl, sec-butyl, tBu, tert-pentyl, sec-butyl, tert-butyl or tert-pentyl. The term "—$(C_0$–$C_6)$-alkyl" or "—$(C_0$–$C_8)$-alkylene" is a hydrocarbon residues containing 1, 2, 3, 4, 5, 6, 7 or 8 carbon atoms. The term "—$C_0$-alkyl" or "—$C_0$-alkylene" is a covalent bond.

Unsaturated alkyl residues are, for example, alkenyl residues such as vinyl, 1-propenyl, 2-propenyl(=allyl), 2-butenyl, 3-butenyl, 2-methyl-2-butenyl, 3-methyl-2-butenyl, 5-hexenyl or 1,3-pentadienyl, or alkynyl residues such as ethynyl, 1-propynyl, 2-propynyl(=propargyl) or 2-butynyl. Alkyl residues can also be unsaturated when they are substituted. Examples of —$(C_3$–$C_8)$-cycloalkyl cyclic alkyl residues are cycloalkyl residues containing 3, 4, 5, 6, 7 or 8 ring carbon atoms like cyclopropyl, cyclobutyl, cyclopentyl, cyclohexyl, cyloheptyl or cyclooctyl, which can also be substituted and/or unsaturated. Unsaturated cyclic alkyl groups and cycloalkyl groups like, for example, cyclopentenyl or cyclohexenyl can be bonded via any carbon atom.

Of course, a cyclic alkyl group has to contain at least three carbon atoms, and an unsaturated alkyl group has to contain at least two carbon atoms. Thus, a group like $(C_1$–$C_8)$-alkyl is to be understood as comprising, among others, saturated acyclic $(C_1$–$C_8)$-alkyl, $(C_3$–$C_6)$-cycloalkyl, and unsaturated $(C_2$–$C_8)$-alkyl like $(C_2$–$C_8)$-alkenyl or $(C_2$–$C_8)$-alkynyl. Similarly, a group like $(C_1$–$C_4)$-alkyl is to be understood as comprising, among others, saturated acyclic $(C_1$–$C_4)$-alkyl, and unsaturated $(C_2$–$C_4)$-alkyl like $(C_2$–$C_4)$-alkenyl or $(C_2$–$C_4)$-alkynyl.

The terms "a monocyclic or bicyclic 6- to 14-membered aryl" or "—$(C_6$–$C_{14})$-aryl" are understood as meaning aromatic hydrocarbon radicals containing from 6 to 14 carbon atoms in the ring. Examples of —$(C_6$–$C_{14})$-aryl radicals are phenyl, naphthyl, for example 1-naphthyl and 2-naphthyl, biphenylyl, for example 2-biphenylyl, 3-biphenylyl and 4-biphenylyl, anthryl or fluorenyl. Biphenylyl radicals, naphthyl radicals and, in particular, phenyl radicals are preferred aryl radicals.

The terms "mono- or bicyclic 4- to 15-membered heterocyclyl" or "—$(C_4$–$C_{15})$-heterocyclyl" refer to heterocycles in which one or more of the 4 to 15 ring carbon atoms are replaced by heteroatoms such as nitrogen, oxygen or sulfur.

Examples are acridinyl, azaindole (1H-pyrrolopyridinyl), azabenzimidazolyl, azaspirodecanyl, azepinyl, azetidinyl, aziridinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, carbazolyl, 4aH-carbazolyl, carbolinyl, chromanyl, chromenyl, cinnolinyl, decahydrochinolinyl, 4,5-dihydrooxazolinyl, dioxazolyl, dioxazinyl, 1,3-dioxolanyl, 1,3-dioxolenyl, 6H-1,5,2-dithiazinyl, dihydrofuro[2,3-b]-tetrahydrofuranyl, furanyl, furazanyl, imidazolidinyl, imidazolinyl, imidazolyl, 1H-indazolyl, indolinyl, indolizinyl, indolyl, 3H-indolyl, isobenzofuranyl, isochromanyl, isoindazolyl, isoindolinyl, isoindolyl, isoquinolinyl (benzimidazolyl), isothiazolyl, isothiazolidinyl, isothiazolinyl, isoxazolyl, isoxazolinyl, isoxazolidinyl, 2-isoxazolinyl, ketopiperazinyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, 1,2-oxa-thiepanyl, 1,2-oxathiolanyl, 1,4-oxazepanyl, 1,2-oxazinyl, 1,3-oxazinyl, 1,4-oxazinyl, oxazolidinyl, oxazolinyl, oxazolyl, oxetanyl, oxocanyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazolyl, pyridoimidazolyl, pyridothiazolyl, pyridinyl, pyridyl, pyrimidinyl, pyrrolidinyl, pyrrolidinonyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrahydrofuranyl, tetrahydropyranyl, tetrahydropyridinyl, tetrahydrothiophenyl, tetrazinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, 1,2-thiazinyl, 1,3-thiazinyl, 1,4-thiazinyl, 1,3-thiazolyl, thiazolyl, thiazolidinyl, thiazolinyl, thienyl, thietanyl, thienothiazolyl, thienooxazolyl, thienoimidazolyl, thietanyl, thiomorpholinyl, thiophenolyl, thiophenyl, thiopyranyl, 1,2,3-triazinyl, 1,2,4-triazinyl, 1,3,5-triazinyl, 1,2,3-triazolyl, 1,2,3-triazolyl, 1,2,4-triazolyl, 1,2,5-triazolyl, 1,3,4-triazolyl and xanthenyl.

Preferred are heterocyclyls, such as benzimidazolyl, 1,3-benzodioxolyl, benzofuranyl, benzothiazolyl, benzothiophenyl, benzoxazolyl, chromanyl, cinnolinyl, 2-furyl, 3-furyl; imidazolyl, indolyl, indazolyl, isochromanyl, isoindolyl, isoquinolinyl, isothiazolyl, isoxazolyl, oxazolyl, phthalazinyl, pteridinyl, purinyl, pyrazinyl, pyrazolyl, pyridazinyl, pyridoimidazolyl, pyridopyridinyl, pyridopyrimidinyl, 2-pyridyl, 3-pyridyl, 4-pyridyl, pyrimidinyl, pyrrolyl; 2-pyrrolyl, 3-pyrrolyl, quinolinyl, quinazolinyl, quinoxalinyl, tetrazolyl, thiazolyl, 2-thienyl and 3-thienyl.

Also preferred are:

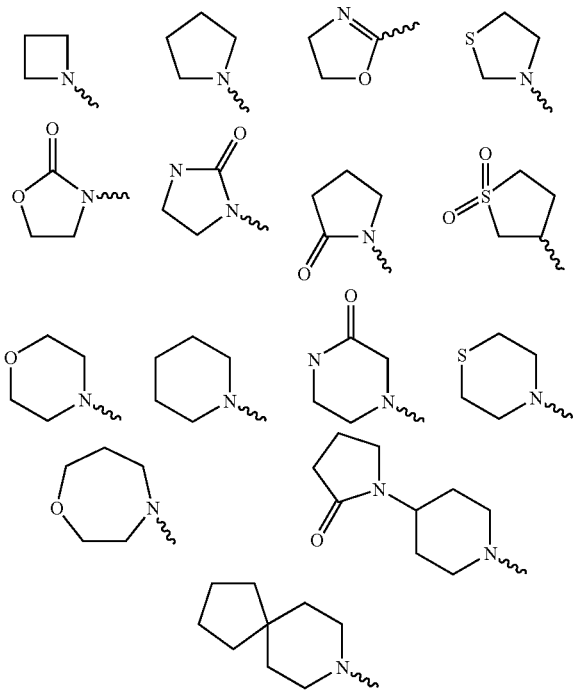

The terms "het" or "a 3- to 7-membered cyclic residue, containing up to 1, 2, 3 or 4 heteroatoms" refer to structures of heterocycles which can be derived from compounds such as azepine, azetidine, aziridine, azirine, 1,4 diazepane, 1,2-diazepine, 1,3-diazepine, 1,4-diazepine, diaziridine, diazirine, dioxazole, dioxazine, dioxole, 1,3-dioxolene, 1,3-dioxolane, furan, imidazole, imidazoline, imidazolidine, isothiazole, isothiazolidine, isothiazoline, isoxazole, isoxazoline, isoxazolidine, 2-isoxazoline, ketomorpholine, ketopiperazine, morpholine, 1,2-oxa-thiepane, 1,2-oxathiolane, 1,4-oxazepane, 1,2-oxazine, 1,3-oxazine, 1,4-oxazine, oxazole, oxaziridine, oxetan, oxirane, piperazine, piperidine, pyran, pyrazine, pyrazole, pyrazoline, pyrazolidine, pyridazine, pyridine, pyrimidine, pyrrole, pyrrolidine, pyrrolidinone, pyrroline, tetrahydrofuran, tetrahydropyran, tetrahydropyridine, tetrazine, tetrazole, thiadiazine thiadiazole, 1,2-thiazine, 1,3-thiazine, 1,4-thiazine, 1,3-thiazole, thiazole, thiazolidine, thiazoline, thienyl, thietan, thiomorpholine, thiopyran, 1,2,3-triazine, 1,2,4-triazine, 1,3,5-triazine, 1,2,3-triazole or 1,2,4-triazole.

The term "$R^1$—N—$R^2$—V can form a 4- to 8-membered cyclic group" or "$R^{11}$ and $R^{12}$ together with the nitrogen atom to which they are bonded can form a 4- to 8-membered monocyclic heterocyclic ring which in addition to the nitrogen atom can contain one or two identical or different ring heteroatoms chosen from oxygen, sulfur and nitrogen" refer to structures of heterocycles which can be derived from compounds such as azepane, azepine, azetidine, dioxazole, dioxazine, 1,4-diazepane, 1,2-diazepine, 1,3-diazepine, 1,4-diazepine, imidazole, imidazoline, imidazolidine, isothiazole, isothiazolidine, isothiazoline, isoxazole, isoxazoline, isoxazolidine, 2-isoxazoline, ketopiperazine, morpholine, [1,4]oxazepane, oxazole, piperazine, piperidine, pyrazine, pyrazole, pyrazoline, pyrazolidine, pyridazine, pyridine, pyrimidine, pyrrole, pyrrolidine, pyrrolidinone, pyrroline, tetrahydropyridine, tetrazine, tetrazole, thiazole, thiadiazole, thiazolidine, thiazoline, thiomorpholine, 1,2,3-triazine, 1,2,4-triazine, 1,3,5-triazine, 1,2,3-triazole or 1,2,4-triazole.

The term "$R^{15}$ and $R^{16}$ together with the carbon atom to which they are bonded can form a 3- to 6 membered carbocyclic ring" refer to structures, which can be derived from compounds such as cyclopropyl, cyclobutyl, cyclopentyl or cyclohexyl.

The term "$R^1$ and $R^3$ together with the atoms to which they are bonded can form a 6- to 8-membered cyclic group, containing up to 1, 2, 3 or 4 heteroatoms chosen from nitrogen, sulfur or oxygen" refers to structures of heterocycles which can be derived from compounds such as azocane, azocane-2-one, cyloheptyl cyclohexyl, cyclooctane, cyclooctene, 1,4-diazepane, 1,2-diazepine, 1,3-diazepine, 1,4-diazepine, [1,4]diazocane, [1,2]diazocan-3-one, [1,3]diazocan-2-one, dioxazine, [1,4]dioxocane, dioxole, ketopiperazine, morpholine, 1,4-oxazepane, 1,2-diazepine, 1,3-diazepine, 1,4-diazepine, [1,4]diazocane, [1,2]diazocan-3-one, [1,3]diazocan-2-one, dioxazine, [1,4]dioxocane, dioxole, ketopiperazine, morpholine, 1,2-oxa-thiepane, 1,2-oxazine, 1,3-oxazine, 1,4-oxazine, [1,4]oxazocane, [1,3]oxazocan-2-one, oxocane, oxocan-2-one, phenyl, piperazine, piperidine, pyran, pyrazine, pyridazine, pyrimidine, 5,6,7,8-tetrahydro-1H-azocin-2-one or thiomorpholine.

The fact that many of the before-listed names of heterocycles are the chemical names of unsaturated or aromatic ring systems does not imply that the, the 4–15 membered mono- or polycyclic group could only be derived from the respective unsaturated ring system. The names here only serve to describe the ring system with respect to ring size and the number of the heteroatoms and their relative positions. As explained above, the 4–15 membered mono- or polycyclic group can be saturated or partially unsaturated or aromatic, and can thus be derived not only from the before-listed heterocycles themselves but also from all their partially or completely hydrogenated analogues and also from their more highly unsaturated analogues if applicable. As examples of completely or partially hydrogenated analogues of the before-listed heterocycles from which this group may be derived the following may be mentioned: pyrroline, pyrrolidine, tetrahydrofuran, tetrahydrothiophene, dihydropyridine, tetrahydropyridine, piperidine, 1,3-dioxolane, 2-imidazoline, imidazolidine, 4,5-dihydro-1,3-oxazol, 1,3-oxazolidine, 4,5-dihydro-1,3-thiazole, 1,3-thiazolidine, perhydro-1,4-dioxane, piperazine, perhydro-1,4-oxazine (=morpholine), perhydro-1,4-thiazine (=thiomorpholine), perhydroazepine, indoline, isoindoline, 1,2,3,4-tetrahydroquinoline, 1,2,3,4-tetrahydroisoquinoline, etc.

The term "—$(C_1$–$C_3)$-perfluoroalkyl" is a partial or totally fluorinated alkyl-residue, which can be derived from residues such as —$CF_3$, —$CHF_2$, —$CH_2F$, —$CHF$—$CF_3$, —$CHF$—$CHF_2$, —$CHF$—$CH_2F$, —$CH_2$—$CF_3$, —$CH_2$—$CHF_2$, —$CH_2$—$CH_2F$, —$CF_2$—$CF_3$, —$CF_2$—$CHF_2$, —$CF_2$—$CH_2F$, —$CH_2$—$CHF$—$CF_3$, —$CH_2$—$CHF$—$CHF_2$, —$CH_2$—$CHF$—$CH_2F$, —$CH_2$—$CH_2$—$CF_3$, —$CH_2$—$CH_2$—$CHF_2$, —$CH_2$—$CH_2$—$CH_2F$, —$CH_2$—$CF_2$—$CF_3$, —$CH_2$—$CF_2$—$CHF_2$, —$CH_2$—$CF_2$—$CH_2F$, —$CHF$—$CHF$—$CF_3$, —$CHF$—$CHF$—$CHF_2$, —$CHF$—$CHF$—$CH_2F$, —$CHF$—$CH_2$—$CF_3$, —$CHF$—$CH_2$—$CHF_2$, —$CHF$—$CH_2$—$CH_2F$, —$CHF$—$CF_2$—$CF_3$, —$CHF$—$CF_2$—$CHF_2$, —$CHF$—$CF_2$—$CH_2F$, —$CF_2$—$CHF$—$CF_3$, —$CF_2$—$CHF$—$CHF_2$, —$CF_2$—$CHF$—$CH_2F$, —$CF_2$—

—$CH_2$—$CF_3$, —$CF_2$—$CH_2$—$CHF_2$, —$CF_2$—$CH_2$—$CH_2F$, —$CF_2$—$CF_2$—$CF_3$, —$CF_2$—$CF_2$—$CHF_2$ or —$CF_2$—$CF_2$—$CH_2F$.

The term "—$(C_1$–$C_3)$-perfluoroalkylene" is a partial or totally fluorinated alkylene-residue, which can be derived from residues such as —$CF_2$—, —$CHF$—, —$CHF$—$CHF_2$—, —$CHF$—$CHF$—, —$CH_2$—$CF_2$—, —$CH_2$—$CHF$—, —$CF_2$—$CF_2$—, —$CF_2$—$CHF$—, —$CH_2$—$CHF$—$CF_2$—, —$CH_2$—$CHF$—$CHF$—, —$CH_2$—$CH_2$—$CF_2$—, —$CH_2$—$CH_2$—$CHF$, —$CH_2$—$CF_2$—$CF_2$—, —$CH_2$—$CF_2$—$CHF$—, —$CHF$—$CHF$—$CH_2$—$CF_2$—, —$CHF$—$CH_2$—$CHF$—, —$CHF$—$CF_2$—$CF_2$—, —$CHF$—$CF_2$—$CHF$—, —$CF_2$—$CHF$—$CF_2$—, —$CF_2$—$CHF$—$CHF$—, —$CF_2$—$CH_2$—$CF_2$—, —$CF_2$—$CH_2$—$CHF$—, —$CF_2$—$CF_2$—$CF_2$—, or —$CF_2$—$CF_2$—$CHF$.

The term "oxo-residue" or "=O" refers to residues such as carbonyl (—C(O)—) or nitroso (—N=O). Halogen is fluorine, chlorine, bromine or iodine, preferably fluorine, chlorine or iodune, particularly preferably chlorine or iodine.

Optically active carbon atoms present in the compounds of the formulae I, II, Ia, Ib, Ic, Id, IIa, IIb or IIc can independently of each other have R configuration or S configuration. The compounds of the formulae I, II, Ia, Ib, Ic, Id, IIa, IIb or IIc can be present in the form of pure enantiomers or pure diastereomers or in the form of mixtures of enantiomers and/or diastereomers, for example in the form of racemates. The present invention relates to pure enantiomers and mixtures of enantiomers as well as to pure diastereomers and mixtures of diastereomers. The invention comprises mixtures of two or of more than two stereoisomers of the formulae I, II, Ia, Ib, Ic, Id, IIa, IIb or IIc, and it comprises all ratios of the stereoisomers in the mixtures. In case the compounds of the formulae I, II, Ia, Ib, Ic, Id, IIa, IIb or IIc can be present as E isomers or Z isomers (or cis isomers or trans isomers) the invention relates both to pure E isomers and pure Z isomers and to E/Z mixtures in all ratios. The invention also comprises all tautomeric forms of the compounds of the formulae I, II, Ia, Ib, Ic, Id, IIa, IIb or IIc.

Diastereomers, including E/Z isomers, can be separated into the individual isomers, for example, by chromatography. Racemates can be separated into the two enantiomers by customary methods, for example by chromatography on chiral phases or by resolution, for example by crystallization of diastereomeric salts obtained with optically active acids or bases. Stereochemically uniform compounds of the formulae I, II, Ia, Ib, Ic, Id, IIa, IIb or IIc can also be obtained by employing stereochemically uniform starting materials or by using stereoselective reactions.

Physiologically tolerable salts of the compounds of formulae I, II, Ia, Ib, Ic, Id, IIa, IIb or IIc are nontoxic salts that are physiologically acceptable, in particular pharmaceutically utilizable salts. Such salts of compounds of the formulae I, II, Ia, Ib, Ic, Id, Ia, IIb or IIc containing acidic groups, for example a carboxyl group COOH, are for example alkali metal salts or alkaline earth metal salts such as sodium salts, potassium salts, magnesium salts and calcium salts, and also salts with physiologically tolerable quaternary ammonium ions such as tetramethylammonium or tetraethylammonium, and acid addition salts with ammonia and physiologically tolerable organic amines, such as methylamine, dimethylamine, trimethylamine, ethylamine, triethylamine, ethanolamine or tris-(2-hydroxyethyl)amine. Basic groups contained in the compounds of the formulae I, II, Ia, Ib, Ic, Id, IIa, IIb or IIc, for example amino groups or guanidino groups, form acid addition salts, for example with inorganic acids such as hydrochloric acid, hydrobromic acid, sulfuric acid, nitric acid or phosphoric acid, or with organic carboxylic acids and sulfonic acids such as formic acid, acetic acid, oxalic acid, citric acid, lactic acid, malic acid, succinic acid, malonic acid, benzoic acid, maleic acid, fumaric acid, tartaric acid, methanesulfonic acid or p-toluenesulfonic acid. Compounds of the formulae I, II, Ia, Ib, Ic, Id, IIa, IIb or IIc, which simultaneously contain a basic group and an acidic group, for example a guanidino group and a carboxyl group, can also be present as zwitterions (betaines), which are likewise included in the present invention.

Salts of compounds of the formulae I, II, Ia, Ib, Ic, Id, Ia, IIb or IIc can be obtained by customary methods known to those skilled in the art, for example by combining a compound of the formulae I, II, Ia, Ib, Ic, Id, IIa, IIb or IIc with an inorganic or organic acid or base in a solvent or dispersant, or from other salts by cation exchange or anion exchange. The present invention also includes all salts of the compounds of the formulae I, II, Ia, Ib, Ic, Id, IIa, IIb or IIc which, because of low physiologically tolerability, are not directly suitable for use in pharmaceuticals but are suitable, for example, as intermediates for carrying out further chemical modifications of the compounds of the formulae I, II, Ia, Ib, Ic, Id, IIa, IIb or IIc or as starting materials for the preparation of physiologically tolerable salts.

The present invention furthermore includes all solvates of compounds of the formulae I, II, Ia, Ib, Ic, Id, IIa, IIb or IIc, for example hydrates or adducts with alcohols.

The invention also includes derivatives and modifications of the compounds of the formulae I, II, Ia, Ib, Ic, Id, IIa, IIb or IIc, for example prodrugs, protected forms and other physiologically tolerable derivatives, as well as active metabolites of the compounds of the formulae I, II, Ia, Ib, Ic, Id, Ia, IIb or IIc. The invention relates in particular to prodrugs and protected forms of the compounds of the formulae I, II, Ia, Ib, Ic, Id, IIa, IIb or IIc, which can be converted into compounds of the formulae I, II, Ia, Ib, Ic, Id, IIa, IIb or IIc under physiological conditions. Suitable prodrugs for the compounds of the formulae I, II, Ia, Ib, Ic, Id, IIa, IIb or IIc, i.e. chemically modified derivatives of the compounds of the formulae I, II, Ia, Ib, Ic, Id, IIa, IIb or IIc having properties which are improved in a desired manner, for example with respect to solubility, bioavailability or duration of action, are known to those skilled in the art. More detailed information relating to prodrugs is found in standard literature like, for example, Design of Prodrugs, H. Bundgaard (ed.), Elsevier, 1985; Fleisher et al., Advanced Drug Delivery Reviews 19 (1996) 115–130; or H. Bundgaard, Drugs of the Future 16 (1991) 443 which are all incorporated herein by reference. Suitable prodrugs for the compounds of the formulae I, II, Ia, Ib, Ic, Id, IIa, IIb or IIc are especially acyl prodrugs and carbamate prodrugs of acylatable nitrogen-containing groups such as amino groups and the guanidino group and also ester prodrugs and amide prodrugs of carboxylic acid groups which may be present in compounds of the formulae I, II, Ia, Ib, Ic, Id, IIa, IIb or IIc. In the acyl prodrugs and carbamate prodrugs one or more, for example one or two, hydrogen atoms on nitrogen atoms in such groups are replaced with an acyl group or a carbamate, preferably a —$(C_1$–$C_6)$-alkyloxycarbonyl group. Suitable acyl groups and carbamate groups for acyl prodrugs and carbamate prodrugs are, for example, the groups $R^{p1}$—CO— and $R^{p2}$O—CO—, in which $R^{p1}$ is hydrogen, $(C_1$–$C_{18})$-alkyl, $(C_3$–$C_8)$-cycloalkyl, $(C_3$–$C_8)$-cycloalkyl-$(C_1$–$C_4)$-alkyl-, $(C_6$–$C_{14})$-aryl, Het-, $(C_6$–$C_{14})$-aryl- ($C_1$–$C_4$)-alkyl- or Het-($C_1$–$C_4$)-alkyl- and in which $R^{p2}$ has the mea indicated for $R^{p1}$ with the exception of hydrogen.

Especially preferred compounds of the formulae I, II, Ia, Ib, Ic, Id, IIa, IIb or IIc are those wherein two or more residues are defined as indicated before for preferred compounds of the formulae I, II, Ia, Ib, Ic, Id, IIa, IIb or IIc, or residues can have one or some of the specific denotations of the residues given in their general definitions or in the definitions of preferred compounds before. All possible combinations of definitions given for preferred definitions and of specific denotations of residues explicitly are a subject of the present invention.

Also with respect to all preferred compounds of the formulae I, II, Ia, Ib, Ic, Id, IIa, IIb or IIc all their stereoisomeric forms and mixtures thereof in any ratio and their physiologically acceptable salts explicitly are a subject of the present invention, as well as are their prodrugs. Similarly, also in all preferred compounds of the formulae I, II, Ia, Ib, Ic, Id, IIa, IIb or IIc, all residues that are present more than one time in the molecule are independent of each other and can be identical or different.

The compounds of the formulae I, II, Ia, Ib, Ic, Id, IIa, IIb or IId can be prepared by utilising procedures and techniques, which per se are well known and appreciated by one of ordinary skill in the art. Starting materials or building blocks for use in the general synthetic procedures that can be applied in the preparation of the compounds of the formulae I, II, Ia, Ib, Ic, Id, IIa, IIb or IId are readily available to one of ordinary skill in the art. In many cases they are commercially available or have been described in the literature. Otherwise they can be prepared from readily available precursor compounds analogously to procedures described in the literature, or by procedures or analogously to procedures described in this application.

In general, compounds of the formula I or II can be prepared, for example in the course of a convergent synthesis, by linking two or more fragments which can be derived retrosynthetically from the formulae I, II, Ia, Ib, Ic, Id, IIa, IIb or IId. More specifically, suitably substituted starting triazole or tetrazole derivatives are employed as building blocks in the preparation of the compounds of formulae I, II, Ia, Ib, Ic, Id, IIa, IIb or IId. If not commercially available, such triazole or tetrazole derivatives can be prepared according to the well-known standard procedures for the formation of the triazole or tetrazole ring system. By choosing suitable precursor molecules, these triazole or tetrazole syntheses allow the introduction of a variety of substituents into the various positions of the triazole or tetrazole system, which can be chemically modified in order to finally arrive at the molecule of the formulae I, II, Ia, Ib, Ic, Id, IIa, IIb or IId having the desired substituent pattern. As one of the comprehensive reviews in which numerous details and literature references on the chemistry of triazoles and tetrazoles and on synthetic procedures for their preparation can be found for example in H. Dehne in Houben-Weyl, "Methoden der Organischen Chemie" (Methods of Organic Chemistry), Georg Thieme Verlag, Stuttgart, Germany 1994, Vol. E8d Hetarene III, 305; E. Nachbaur and G. Faleschini in Houben-Weyl, "Methoden der Organischen Chemie" (Methods of Organic Chemistry), Georg Thieme Verlag, Stuttgart, Germany 1994, Vol. E8d Hetarene III, 479; H. R. Meyer and H. Heimgartner in Houben-Weyl, "Methoden der Organischen Chemie" (Methods of Organic Chemistry), Georg Thieme Verlag, Stuttgart, Germany 1994, Vol. E8d Hetarene III, 664.

If starting triazole or tetrazole derivatives are not commercially available and have to be synthesized this can be done, for example, according to the well-known triazole or tetrazole syntheses mentioned above. In the following procedures of particular interest for the embodiment of this invention are listed and referenced briefly, however, they are standard procedures comprehensively discussed in the literature, and are well known to one skilled in the art. Although not always shown explicitly, in certain cases positional isomers will occur during the synthesis of the below mentioned reactions. Nevertheless such mixtures of positional isomers, can be separated by modern separation techniques like, for example, preparative HPLC.

1) a) J. Duncia et al., J. Org. Chem. (1991) 56, 2395.
   b) E. W. Thomas et al., Synthesis (1993) 767.

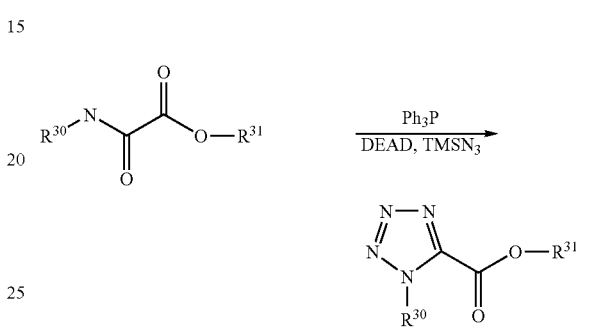

2) K. Tamura et al., J. Org. Chem. (1993) 58, 32.

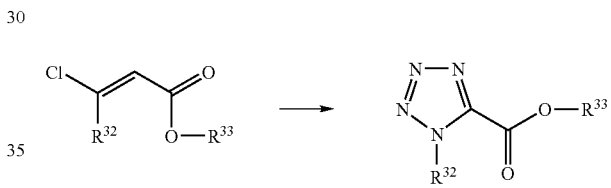

3) F. A. Amer et al., Tetrahedron Lett. (1997) 38, 1257

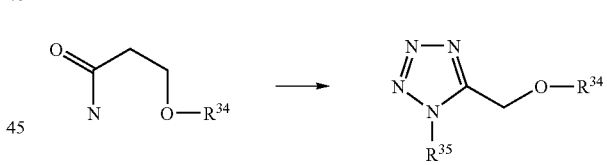

4) V. Novack et al., U.S. Pat. No. 5,525,733.

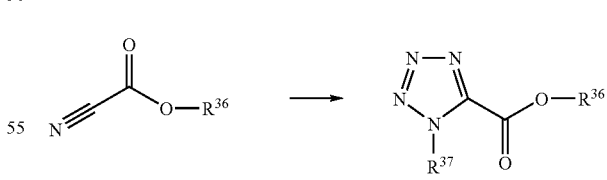

5) J. Cesar et al., Synth. Commun. (2000) 30, 4147.

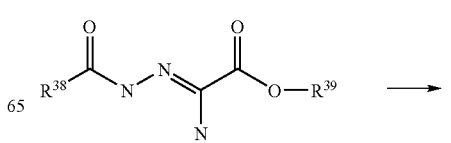

-continued
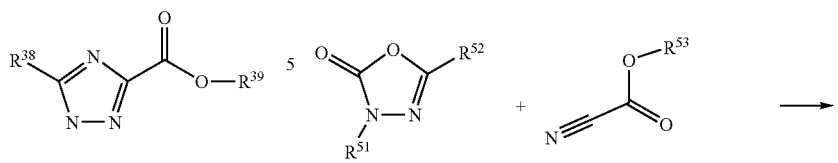
6) B. Altural, Org. Prep. Proced. Int. (1991) 23, 147.
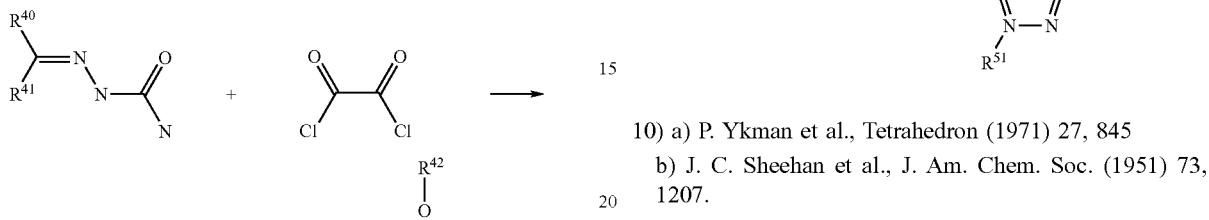
7) R. Hiusgen et al., Liebigs Ann. Chem. (1963) 653, 105.
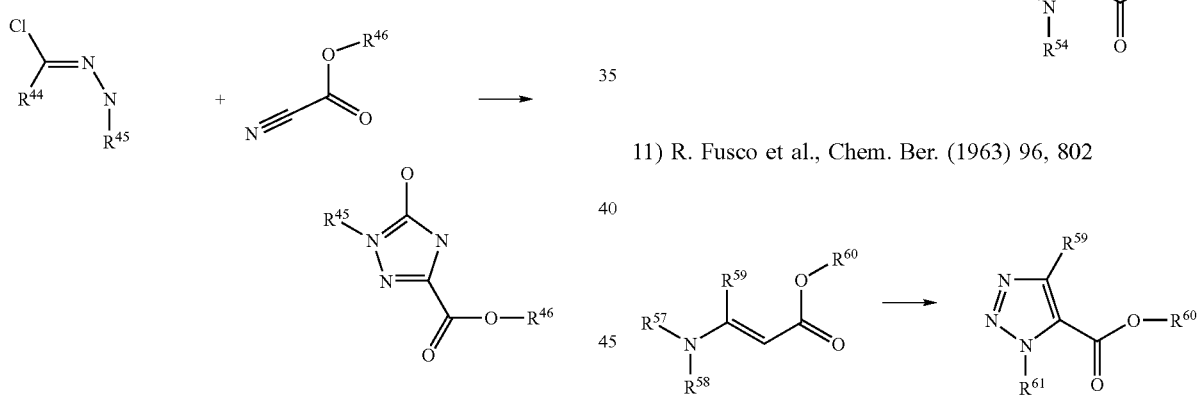
8) L. Bruché et al., Synthesis (1986) 9, 772.
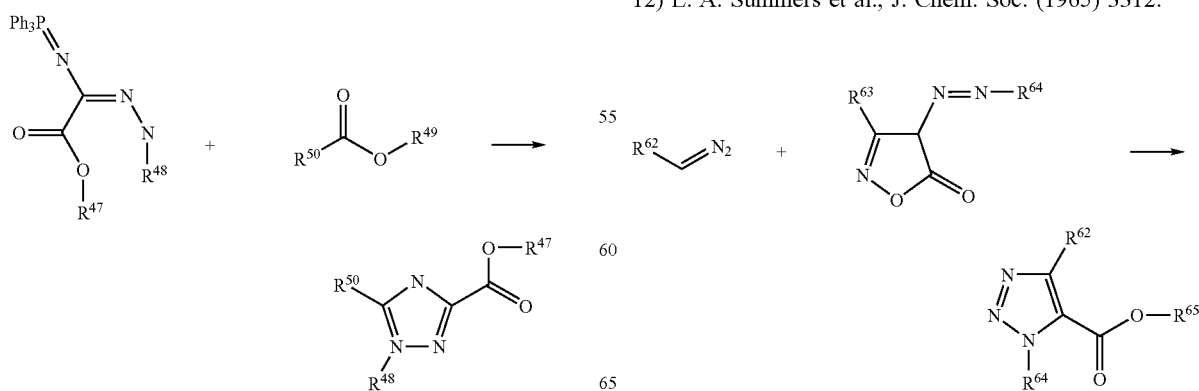
9) Sauer et al., Tetrahedron Lett. (1968) 325
10) a) P. Ykman et al., Tetrahedron (1971) 27, 845
b) J. C. Sheehan et al., J. Am. Chem. Soc. (1951) 73, 1207.
11) R. Fusco et al., Chem. Ber. (1963) 96, 802
12) L. A. Summers et al., J. Chem. Soc. (1965) 3312.

13) C. Pedersen, Acta Chem. Scand. (1958) 12, 1236.

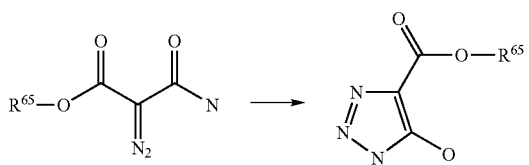

14) P. Murray-Rust et al., J. Chem. Soc. Perkin Trans 1 (1984) 713.

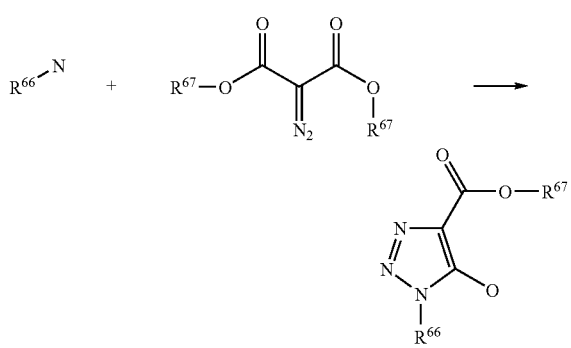

15) S. Danoun et al., Bull. Soc. Chim. Fr. (1995) 132, 943.

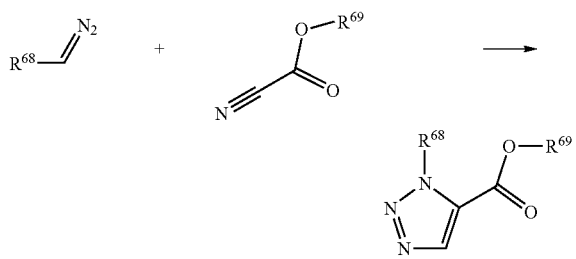

Further, in order to obtain the desired substituents at the triazole or tetrazole ring system in the formulae I, II, Ia, Ib, Ic, Id, IIa, IIb or IId, the functional groups introduced into the ring system during the triazole or tetrazole synthesis can be chemically modified. Especially the groups present in the triazole or tetrazole ring system can be modified by a variety of reactions and thus the desired residue $R^{1a}$ be obtained. For example alkyl- or hydroxymethyl groups as well as formyl groups attached to the triazole or tetrazole core can be transformed to a variety of functional groups, for example, to the corresponding carboxylic acid or carboxylic ester by many oxidative reactions well known to those skilled in the art. Moreover a nitrile group attached to the triazole or tetrazole ring can, for example, easily be converted into the desired acid under acidic or basic conditions. In addition, carboxylic acid groups and acetic acid groups can be converted into their homologues by usual reactions for chain elongation of carboxylic acids. Halogen atoms can be introduced, for example according to procedures like the following described in the literature. For the fluorination of triazole or tetrazoles N-fluoro-2,4,6-trimethylpyridinium triflate is one reagent of choice (T. Umemoto, S. Fukami, G. Tomizawa, K. Harasawa, K. Kawada, K. Tomita, J. Am. Chem. Soc. (1990) 112, 8563 see also K. Manko et al., J. Fluorine Chem. (1988) 39, 435; R. Storer et al. Nucleosides Nucleotides (1999) 18; 203) however, other suitable fluorinating reagents may also be employed where appropriate. The chlorination, bromination, or iodination of triazole or tetrazoles can be accomplished by the reaction with elemental halogens or by the use of NCS, NBS or NIS and many other reagents well known to those skilled in the art.

By selective halogen/metal exchange or metalation by selective hydrogen/metal exchange and subsequent reaction with a wide range of electrophiles various substituents can be introduced at the heterocyclic nucleus. (M. R. Grimmett, Heterocycles (1994) 37, 2087; V. D. Gardner et al., J. Heterocycl. Chem. (1984), 21, 121; D. Butler et al., J. Org. Chem. (1971) 36, 2542). Halogens or hydroxy groups (via their triflates or nonaflates)—or primary amines (via their diazonium salts) present in the triazole or tetrazole structure—can be converted directly, or after interconversion to the corresponding stannane, or boronic acid, into a variety of other functional groups like for example —CN, —CF$_3$, —C$_2$F$_5$, ethers, acids, amides, amines, alkyl- or aryl-groups mediated by means of transition metals, namely palladium or nickel catalysts or copper salts and reagents for example referred to below (F. Diederich, P. Stang, Metal-catalyzed Cross-coupling Reactions, Wiley-VCH, 1998; or M. Beller, C. Bolm, Transition Metals for Organic Synthesis, Wiley-VCH, 1998; J. Tsuji, Palladium Reagents and Catalysts, Wiley, 1996; J. Hartwig, Angew. Chem. (1998) 110, 2154; B. Yang, S. Buchwald, J. Organomet. Chem. (1999) 576, 125; T. Sakamoto, K. Ohsawa, J. Chem. Soc. Perkin Trans I (1999) 2323; D. Nichols, S. Frescas, D. Marona-Lewicka, X. Huang, B. Roth, G. Gudelsky, J. Nash, J. Med. Chem. (1994) 37, 4347; P. Lam, C. Clark, S. Saubern, J. Adams, M. Winters, D. Chan, A. Combs, Tetrahedron Lett. (1998) 39, 2941; D. Chan, K. Monaco, R. Wang, M. Winters, Tetrahedron Lett. (1998) 39, 2933; V. Farina, V. Krishnamurthy, W. Scott, The Stille Reaction, Wiley, 1994; F. Qing et al. J. Chem. Soc. Perkin Trans. I (1997) 3053; S. Buchwald et al. J. Am. Chem Soc. (2001) 123, 7727; S. Kang et al. Synlett (2002) 3, 427; S. Buchwald et al. Organic Lett. (2002) 4, 581; T. Fuchikami et al. Tetrahedron Lett. (1991) 32, 91; Q. Chen et al. Tetrahedron Lett. (1991) 32, 7689). For example, nitro groups can be reduced to amino groups by means of various reducing agents, such as sulfides, dithionites, complex hydrides or by catalytic hydrogenation. A reduction of a nitro group may also be carried out at a later stage of the synthesis of a compound of the formulae I, II, Ia, Ib, Ic, Id, IIa, IIb or IId, and a reduction of a nitro group to an amino group may also occur simultaneously with a reaction performed on another functional group, for example when reacting a group like a cyano group with hydrogen sulfide or when hydrogenating a group. In order to introduce the residues $R^{1a}$, amino groups can then be modified according to standard procedures for alkylation, for example by reaction with (substituted) alkyl halogenides or by reductive amination of carbonyl compounds, according to standard procedures for acylation, for example by reaction with activated carboxylic acid derivatives such as acid chlorides, anhydrides, activated esters or others or by reaction with carboxylic acids in the presence of an activating agent, or according to standard procedures for sulfonylation, for example by reaction with sulfonyl chlorides.

Ester groups present in the triazole or tetrazole nucleus can be hydrolyzed to the corresponding carboxylic acids, which after activation can then be reacted with amines or alcohols under standard conditions to give amides or alcohols, respectively. Ester groups present in the triazole or tetrazole nucleus can be converted to other esters by transesterification. Carboxylic acids attached to a suitable triazole or tetrazole nucleus can also be alkylated to give esters. Ether groups present at the triazole or tetrazole nucleus, for example benzyloxy groups or other easily cleavable ether groups, can be cleaved to give hydroxy groups which then can be reacted with a variety of agents, for example etherification agents or activating agents allowing replacement of the hydroxy group by other groups. Sulfur-containing groups can be reacted analogously.

During the course of the synthesis in order to modify the groups $R^{71}$ or $R^{8'}$ attached to the triazole or tetrazole ring system by application of parallel synthesis methodology, a variety of reactions can be extremely useful, including, for example, palladium, nickel or copper catalysis. Such reactions are described for example in F. Diederich, P. Stang, Metal-catalyzed Cross-coupling Reactions, Wiley-VCH (1998); or M. Beller, C. Bolm, Transition Metals for Organic Synthesis, Wiley-VCH (1998); J. Tsuji, Palladium Reagents and Catalysts, Wiley (1996); J. Hartwig, Angew. Chem. (1998), 110, 2154; B. Yang, S. Buchwald, J. Organomet. Chem. (1999), 576, 125; P. Lam, C. Clark, S. Saubern, J. Adams, M. Winters, D. Chan, A. Combs, Tetrahedron Lett. (1998), 39, 2941; D. Chan, K. Monaco, R. Wang, M. Winters, Tetrahedron Lett. (1998), 39, 2933; J. Wolfe, H. Tomori, J. Sadight, J. Yin, S. Buchwald, J. Org. Chem. (2000), 65, 1158; V. Farina, V. Krishnamurthy, W. Scott, The Stille Reaction, Wiley, (1994); S. Buchwald et al., J. Am. Chem. Soc. (2001), 123, 7727; S. Kang et al., Synlett (2002), 3, 427; S. Buchwald et al., Org. Lett. (2002), 4, 581.

The previously-mentioned reactions for the conversion of functional groups are furthermore, in general, extensively described in textbooks of organic chemistry like M. Smith, J. March, March's Advanced Organic Chemistry, Wiley-VCH, 2001 and in treatises like Houben-Weyl, "Methoden der Organischen Chemie" (Methods of Organic Chemistry), Georg Thieme Verlag, Stuttgart, Germany, or "Organic Reactions", John Wiley & Sons, New York, or R. C. Larock, "Comprehensive Organic Transformations", Wiley-VCH, $2^{nd}$ ed (1999), B. Trost, I. Fleming (eds.) Comprehensive Organic Synthesis, Pergamon, 1991; A. Katritzky, C. Rees, E. Scriven Comprehensive Heterocyclic Chemistry II, Elsevier Science, 1996) in which details on the reactions and primary source literature can be found. Due to the fact that in the present case the functional groups are attached to a triazole or tetrazole ring it may in certain cases become necessary to specifically adapt reaction conditions or to choose specific reagents from a variety of reagents that can in principle be employed in a conversion reaction, or otherwise to take specific measures for achieving a desired conversion, for example to use protection group techniques. However, finding out suitable reaction variants and reaction conditions in such cases does not cause any problems for one skilled in the art.

The structural elements present in the residues attached at the nitrogen atom of the triazole or tetrazole ring in the compounds of the formulae I, II, Ia, Ib, Ic, Id, IIa, IIb or IId and in the $COR^{8'}$ group present at the triazole or tetrazole ring can be introduced into the starting triazole or tetrazole derivative obtainable as outlined above by consecutive reaction steps using synthesis methodologies like those outlined below using procedures which per se are well known to one skilled in the art.

The residues $R^{8'}$ that can be introduced in formula 3, for example, by condensing a corresponding carboxylic acid of the formula 3 with a compound of the formula $HR^{8'}$, i.e., with an amine of the formula $HN(R^{1'})R^{2'}$—V-G-M to give a compound of the formula 4. The compound of the formula 4 thus obtained can already contain the desired final groups, i.e. the groups $R^{8'}$ and $R^{71}$ can be the groups —$N(R^1)$—$R^2$—V-G-M and $R^0$-Q- as defined in the formula I or II, or optionally in the compound of the formula 4 thus obtained subsequently the residue or the residues $R^{8'}$ and the residue $R^{71}$ are converted into the residues —$N(R^1)R^2$—V-G-M and $R^0$-Q-, respectively, to give the desired compound of the formula I or II.

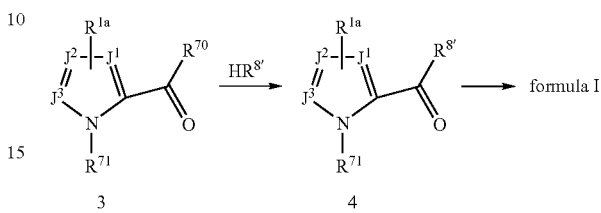

Thus, the residues $R^{8'}$ and the residues $R^{1'}$ and $R^{2'}$—V-G-M contained therein can have the denotations of $R^1$ and $R^2$—V-G-M, respectively, given above or in addition in the residues $R^{1'}$ and $R^{2'}$—V-G-M functional groups can also be present in the form of groups that can subsequently be transformed into the final groups $R^1$ and $R^2$—V-G-M, i.e. functional groups can be present in the form of precursor groups or of derivatives, for example in protected form. In the course of the preparation of the compounds of the formula I or II it can generally be advantageous or necessary to introduce functional groups which reduce or prevent undesired reactions or side reactions in the respective synthesis step, in the form of precursor groups which are later converted into the desired functional groups, or to temporarily block functional groups by a protective group strategy suited to the synthesis problem. Such strategies are well known to those skilled in the art (see, for example, Greene and Wuts, Protective Groups in Organic Synthesis, Wiley, 1991, or P. Kocienski, Protecting Groups, Thieme 1994). As examples of precursor groups cyano groups and nitro groups may be mentioned. The cyano group can in a later step be transformed into carboxylic acid derivatives or by reduction into aminomethyl groups, or the nitro groups may be transformed by reduction like catalytic hydrogenation into amino groups. Protective groups can also have the meaning of a solid phase, and cleavage from the solid phase stands for the removal of the protective group. The use of such techniques is known to those skilled in the art (Burgess K (Ed.) Solid Phase Organic Synthesis, New York, Wiley, 2000). For example, a phenolic hydroxy group can be attached to a trityl-polystyrene resin, which serves as a protecting group, and the molecule is cleaved from this resin by treatment with TFA at a later stage of the synthesis.

The residue $R^{71}$ in the compounds of the formulae 3 and 4 can denote the group -Q-$R^0$ as defined above which finally is to be present in the desired target molecule of the formula I or II, or it can denote a group which can subsequently be transformed into the group -Q-$R^0$, for example a precursor group or a derivative of the group -Q-$R^0$ in which functional groups are present in protected form, or $R^{71}$ can denote a hydrogen atom or a protective group for the nitrogen atom of the triazole or tetrazole ring. Similarly, the residues $R^{1a}$ in the formulae 3 and 4 have the corresponding definitions $R^3$ in formula I or II as defined above, however, for the synthesis of the compounds of the formula I or II these residues, too, can in principle be present at the stage of the condensation of a compound of the formula 3 with a compound of the formula HR$^{8'}$ giving a compound of the formula 4 in the form of precursor groups or in protected form.

The residues R$^{70}$ in the compounds of the formula 3 which can be identical or different, can be, for example, hydroxy or ($C_1$–$C_4$)-alkoxy, i.e., the groups COR$^{70}$ present in the compounds of the formula 3 can be, for example, the free carboxylic acids or esters thereof like alkyl esters as can be the groups COR$^{8'}$ in the compounds of the formula I or II. The groups COR$^{70}$ can also be any other activated derivative of a carboxylic acid which allows amide formation, ester formation or thioester formation with a compound of the formula HR$^{8'}$. The group COR$^{70}$ can be, for example, an acid chloride, an activated ester like a substituted phenyl ester or an N-hydroxysuccinimide or a hydroxybenzotriazole ester, an azolide like an imidazolide, an azide or a mixed anhydride, for example a mixed anhydride with a carbonic acid ester or with a sulfonic acid, which derivatives can all be prepared from the carboxylic acid by standard procedures and can be reacted with an amine, an alcohol or a mercaptan of the formula HR$^{8'}$ under standard conditions. A carboxylic acid group COOH representing COR$^{70}$ in a compound of the formula 3 can be obtained, for example, from an ester group introduced into the triazole or tetrazole system during a triazole or tetrazole synthesis by standard hydrolysis procedures. It can also be obtained, for example, by hydrolysis of a nitrile group introduced into the triazole or tetrazole system during a triazole or tetrazole synthesis.

Compounds of the formula I or II in which a group COR$^{8'}$ is an ester group can also be prepared from compounds of the formula 3 in which COR$^{70}$ is a carboxylic acid group by common esterification reactions like, for example, reacting the acid with an alcohol under acid catalysis, or alkylation of a salt of the carboxylic acid with an electrophile like an alkyl halogenide, or by transesterification from another ester. Compounds of the formula I or II in which a group COR$^{8'}$ is an amide group can be prepared from amines and compounds of the formula 3 in which COR$^{70}$ is a carboxylic acid group or an ester thereof by common amination reactions. Especially for the preparation of amides the compounds of the formula 3 in which COR$^{70}$ is a carboxylic acid group can be condensed under standard conditions with compounds of the formula HR$^{8'}$ which are amines by means of common coupling reagents used in peptide synthesis. Such coupling reagents are, for example, carbodiimides like dicyclohexylcarbodiimide (DCC) or diisopropylcarbodiimide, carbonyldiazoles like carbonyldiimidazole (CDI) and similar reagents, propylphosphonic anhydride, O-((cyano-(ethoxycarbonyl)-methylene)amino)-N,N,N',N'-tetramethyluronium tetrafluoroborate (TOTU), diethylphosphoryl cyanide (DEPC) or bis-(2-oxo-3-oxazolidinyl)-phosphoryl chloride (BOP-Cl) and many others.

If the residue -Q-R$^0$ present in a triazole or tetrazole of the formula I or II or the residue R$^{71}$ present in a triazole or tetrazole of the formula 3, or a residue in which functional groups within the residue -Q-R$^0$ or R$^{71}$ are present in protected form or in the form of a precursor group, have not already been introduced during a preceding step, for example during a synthesis of the triazole or tetrazole nucleus, these residues can, for example, be introduced into the 1-position of the triazole or tetrazole system by conventional literature procedures well known to one skilled in the art for N-alkylation, reductive amination, N-arylation, N-acylation or N-sulfonylation of ring nitrogen atoms of heterocycles. The starting triazole or tetrazole derivative that is to be employed in such a reaction carries a hydrogen atom at the nitrogen atom. N-Alkylation of a ring nitrogen atom can, for example, be performed under standard conditions, preferably in the presence of a base like $K_2CO_3$, $Cs_2CO_3$, NaH or KO$^t$Bu, using an alkylating compound of the formula LG-Q-R$^0$ or of the formula R$^{71}$-LG, wherein the atom in the group Q or in the group R$^{71}$ bonded to the group LG in this case is an aliphatic carbon atom of an alkyl moiety and LG is a leaving group, for example halogen like chlorine, bromine or iodine, or a sulfonyloxy group like tosyloxy, mesyloxy or trifluormethylsulfonyloxy. LG may, for example, also be a hydroxy group which, in order to achieve the alkylation reaction, is activated in a well-known Mitsunobu reaction by a conventional activating agent. The regioselectivity of the N-alkylation can be controlled by the choice of the base, solvent and reaction conditions. Nevertheless mixtures of positional isomers, can be separated by modern separation techniques like, for example, flash chromatography, crystallisation or preparative HPLC.

For the preparation of compounds in which A is a direct linkage and an aromatic group is directly bonded to nitrogen atom of the triazole or tetrazole system, conventional arylation procedures can be used. For example aryl fluorides like alkyl fluorobenzoates or 4-fluorophenyl nitriles can be employed as arylating agents. Such processes are described, for example, by K. Cooper et al., J. Med. Chem. (1992), 35, 3115; M. Artico et al., Eur. J. Med. Chem. Chim. Ther. (1992) 27, 219; X.-J. Wang et al., Tetrahedron Letters (2000) 41, 5321; M. L. Cerrada et al., Synth. Commun. (1993) 23, 1947. Alternatively a wide variety of substituted aryl iodides, aryl bromides or aryl triflates can serve as arylating agents at the heterocyclic nitrogen in a copper salt or palladium mediated reaction according for example to P. Cozzi et al. Farmaco (1987) 42, 205; P. Unangst, D. Connor, R. Stabler, R. Weikert, J. Heterocycl. Chem. (1987) 24, 811; G. Tokmakov, I. Grandberg, Tetrahedron (1995) 51, 2091; D. Old, M. Harris, S. Buchwald, Org. Lett. (2000) 2, 1403, G. Mann, J. Hartwig, M. Driver, C. Fernandez-Rivas, J. Am. Chem. Soc. (1998) 120, 827; J. Hartwig, M. Kawatsura, S. Hauk, K. Shaughnessy, L. J. Org. Chem. (1999) 64, 5575; S. Buchwald et al., J. Am. Chem. Soc. (2001) 123, 7727. Moreover such arylations can also be accomplished by reaction of a wide range of substituted aryl boronic acids as demonstrated for example by P. Lam et al., Tetrahedron Lett. (1998) 39, 2941; V. Collot et al., Tetrahedron Lett. (2000) 41, 9053; P. Lam et al., Tetrahedron Lett. (2001) 42, 3415;

Preferred methods include, but are not limited to those described in the Examples.

The compounds of the present invention are serine protease inhibitors, which inhibit the activity of the blood coagulation enzyme factors Xa and/or factor VIIa. In particular, they are highly active inhibitors of factor Xa. They are specific serine protease inhibitors inasmuch as they do not substantially inhibit the activity of other proteases whose inhibition is not desired. The activity of the compounds of the formulae I, II, Ia, Ib, Ic, Id, IIa, IIb or IId can be determined, for example, in the assays described below or in other assays known to those skilled in the art. With respect to factor Xa inhibition, a preferred embodiment of the invention comprises compounds, which have a Ki$\leq$1 mM for factor Xa inhibition as determined in the assay described below, with or without concomitant factor VIIa inhibition, and which preferably do not substantially inhibit the activity of other proteases involved in coagulation and fibrinolysis whose inhibition is not desired (using the same concentration of the inhibitor). The compounds of the invention inhibit factor Xa catalytic activity either directly, within the prothrombinase complex or as a soluble subunit, or indirectly, by inhibiting the assembly of factor Xa into the prothrombinase complex.

The present invention also relates to the compounds of the formulae I, II, Ia, Ib, Ic, Id, IIa, IIb or IId and/or their physiologically tolerable salts and/or their prodrugs for use as pharmaceuticals (or medicaments), to the use of the compounds of the formula formulae I, II, Ia, Ib, Ic, Id, IIa, IIb or IId and/or their physiologically tolerable salts and/or their prodrugs for the production of pharmaceuticals for inhibition of factor Xa and/or factor VIIa or for influencing blood coagulation, inflammatory response or fibrinolysis or for the therapy or prophylaxis of the diseases mentioned above or below, for example for the production of pharmaceuticals for the therapy and prophylaxis of cardiovascular disorders, thromboembolic diseases or restenoses.

The invention also relates to the use of the compounds of the formulae I, II, Ia, Ib, Ic, Id, IIa, IIb or IId and/or their physiologically tolerable salts and/or their prodrugs for the inhibition of factor Xa and/or factor VIIa or for influencing blood coagulation or fibrinolysis or for the therapy or prophylaxis of the diseases mentioned above or below, for example for use in the therapy and prophylaxis of cardiovascular disorders, thromboembolic diseases or restenoses, and to methods of treatment aiming at such purposes including methods for said therapies and prophylaxis.

The present invention also relates to pharmaceutical preparations (or pharmaceutical compositions) which contain an effective amount of at least one compound of the formulae I, II, Ia, Ib, Ic, Id, IIa, IIb or IId and/or its physiologically tolerable salts and/or its prodrugs in addition to a customary pharmaceutically acceptable carrier, i.e. one or more pharmaceutically acceptable carrier substances or excipients and/or auxiliary substances or additives.

The invention also relates to the treatment of disease states such as abnormal thrombus formation, acute myocardial infarction, unstable angina, thromboembolism, acute vessel closure associated with thrombolytic therapy or percutaneous transluminal coronary angioplasty, transient ischemic attacks, stroke, pathologic thrombus formation occurring in the veins of the lower extremities following abdominal, knee and hip surgery, a risk of pulmonary thromboembolism, or disseminated systemic intravascular coagulatopathy occurring in vascular systems during septic shock, certain viral infections or cancer.

The compounds of the formulae I, II, Ia, Ib, Ic, Id, IIa, IIb or IIc and their physiologically tolerable salts and their prodrugs can be administered to animals, preferably to mammals, and in particular to humans as pharmaceuticals for therapy or prophylaxis. They can be administered on their own, or in mixtures with one another or in the form of pharmaceutical preparations, which permit enteral or parenteral administration.

The pharmaceuticals can be administered orally, for example in the form of pills, tablets, lacquered tablets, coated tablets, granules, hard and soft gelatin capsules, solutions, syrups, emulsions, suspensions or aerosol mixtures. Administration, however, can also be carried out rectally, for example in the form of suppositories, or parenterally, for example intravenously, intramuscularly or subcutaneously, in the form of injection solutions or infusion solutions, microcapsules, implants or rods, or percutaneously or topically, for example in the form of ointments, solutions or tinctures, or in other ways, for example in the form of aerosols or nasal sprays.

The pharmaceutical preparations according to the invention are prepared in a manner known per se and familiar to one skilled in the art, pharmaceutically acceptable inert inorganic and/or organic carriers being used in addition to the compound(s) of the formulae I, II, Ia, Ib, Ic, Id, IIa, IIb or IIc and/or its (their) physiologically tolerable salts and/or its (their) prodrugs. For the production of pills, tablets, coated tablets and hard gelatin capsules it is possible to use, for example, lactose, cornstarch or derivatives thereof, talc, stearic acid or its salts, etc. Carriers for soft gelatin capsules and suppositories are, for example, fats, waxes, semisolid and liquid polyols, natural or hardened oils, etc. Suitable carriers for the production of solutions, for example injection solutions, or of emulsions or syrups are, for example, water, saline, alcohols, glycerol, polyols, sucrose, invert sugar, glucose, vegetable oils, etc. Suitable carriers for microcapsules, implants or rods are, for example, copolymers of glycolic acid and lactic acid. The pharmaceutical preparations normally contain about 0.5% to 90% by weight of the compounds of the formulae I, II, Ia, Ib, Ic, Id, IIa, IIb or IIc and/or their physiologically tolerable salts and/or their prodrugs. The amount of the active ingredient of the formulae I, II, Ia, Ib, Ic, Id, IIa, IIb or IIc and/or its physiologically tolerable salts and/or its prodrugs in the pharmaceutical preparations normally is from about 0.5 mg to about 1000 mg, preferably from about 1 mg to about 500 mg.

In addition to the active ingredients of the formulae I, II, Ia, Ib, Ic, Id, IIa, IIb or IIc and/or their physiologically acceptable salts and/or prodrugs and to carrier substances, the pharmaceutical preparations can contain additives such as, for example, fillers, disintegrants, binders, lubricants, wetting agents, stabilizers, emulsifiers, preservatives, sweeteners, colorants, flavorings, aromatizers, thickeners, diluents, buffer substances, solvents, solubilizers, agents for achieving a depot effect, salts for altering the osmotic pressure, coating agents or antioxidants. They can also contain two or more compounds of the formulae I, II, Ia, Ib, Ic, Id, IIa, IIb or IIc and/or their physiologically tolerable salts and/or their prodrugs. In case a pharmaceutical preparation contains two or more compounds of the formulae I, II, Ia, Ib, Ic, Id, IIa, IIb or IIc the selection of the individual compounds can aim at a specific overall pharmacological profile of the pharmaceutical preparation. For example, a highly potent compound with a shorter duration of action may be combined with a long-acting compound of lower potency. The flexibility permitted with respect to the choice of substituents in the compounds of the formulae I, II, Ia, Ib, Ic, Id, Ia, IIb or IIc allows a great deal of control over the biological and physico-chemical properties of the compounds and thus allows the selection of such desired compounds. Furthermore, in addition to at least one compound of the formulae I, II, Ia, Ib, Ic, Id, IIa, IIb or IIc and/or its physiologically tolerable salts and/or its prodrugs, the pharmaceutical preparations can also contain one or more other therapeutically or prophylactically active ingredients.

As inhibitors of factor Xa and/or factor VIIa the compounds of the formulae I, II, Ia, Ib, Ic, Id, IIa, IIb or IIc and their physiologically tolerable salts and their prodrugs are generally suitable for the therapy and prophylaxis of conditions in which the activity of factor Xa and/or factor VIIa plays a role or has an undesired extent, or which can favorably be influenced by inhibiting factor Xa and/or factor VIIa or decreasing their activities, or for the prevention, alleviation or cure of which an inhibition of factor Xa and/or factor VIIa or a decrease in their activity is desired by the physician. As inhibition of factor Xa and/or factor VIIa influences blood coagulation and fibrinolysis, the compounds of the formulae I, II, Ia, Ib, Ic, Id, IIa, IIb or IIc and their physiologically tolerable salts and their prodrugs are generally suitable for reducing blood clotting, or for the therapy and prophylaxis of conditions in which the activity of the blood coagulation system plays a role or has an undesired extent, or which can favorably be influenced by reducing blood clotting, or for the prevention, alleviation or cure of which a decreased activity of the blood coagulation system is desired by the physician. A specific subject of the present invention thus are the reduction or inhibition of unwanted blood clotting, in particular in an individual, by administering an effective amount of a compound I or a physiologically tolerable salt or a prodrug thereof, as well as pharmaceutical preparations therefor.

Conditions in which compounds of the formulae I, II, Ia, Ib, Ic, Id, IIa, IIb or IIc can be favorably used include, for example, cardiovascular disorders, thromboembolic diseases or complications associated, for example, with infection or surgery. The compounds of the present invention can also be used to reduce an inflammatory response. Examples of specific disorders for the treatment or prophylaxis of which the compounds of the formulae I, II, Ia, Ib, Ic, Id, IIa, IIb or IIc can be used are coronary heart disease, myocardial infarction, angina pectoris, vascular restenosis, for example restenosis following angioplasty like PTCA, adult respiratory distress syndrome, multi-organ failure, stroke and disseminated intravascular clotting disorder. Examples of related complications associated with surgery are thromboses like deep vein and proximal vein thrombosis, which can occur following surgery. In view of their pharmacological activity the compounds of the invention can replace or supplement other anticoagulant agents such as heparin. The use of a compound of the invention can result, for example, in a cost saving as compared to other anticoagulants. When using the compounds of the formulae I, II, Ia, Ib, Ic, Id, IIa, IIb or IIc the dose can vary within wide limits and, as is customary and is known to the physician, is to be suited to the individual conditions in each individual case. It depends, for example, on the specific compound employed, on the nature and severity of the disease to be treated, on the mode and the schedule of administration, or on whether an acute or chronic condition is treated or whether prophylaxis is carried out. An appropriate dosage can be established using clinical approaches well known in the medical art. In general, the daily dose for achieving the desired results in an adult weighing about 75 kg is from 0.01 mg/kg to 100 mg/kg, preferably from 0.1 mg/kg to 50 mg/kg, in particular from 0.1 mg/kg to 10 mg/kg, (in each case in mg per kg of body weight). The daily dose can be divided, in particular in the case of the administration of relatively large amounts, into several, for example 2, 3 or 4, part administrations. As usual, depending on individual behavior it may be necessary to deviate upwards or downwards from the daily dose indicated.

A compound of the formulae I, II, Ia, Ib, Ic, Id, IIa, IIb or IIc can also advantageously be used as an anticoagulant outside an individual. For example, an effective amount of a compound of the invention can be contacted with a freshly drawn blood sample to prevent coagulation of the blood sample. Further, a compound of the formulae I, II, Ia, Ib, Ic, Id, IIa, IIb or IIc and its salts can be used for diagnostic purposes, for example in in vitro diagnoses, and as an auxiliary in biochemical investigations. For example, a compound of the formulae I, II, Ia, Ib, Ic, Id, IIa, IIb or IIc can be used in an assay to identify the presence of factor Xa and/or factor VIIa or to isolate factor Xa and/or factor VIIa in a substantially purified form. A compound of the invention can be labeled with, for example, a radioisotope, and the labeled compound bound to factor Xa and/or factor VIIa is then detected using a routine method useful for detecting the particular label. Thus, a compound of the formulae I, II, Ia, Ib, Ic, Id, IIa, IIb or IIc or a salt thereof can be used as a probe to detect the location or amount of factor Xa and/or factor VIIa activity in vivo, in vitro or ex vivo.

Furthermore, the compounds of the formulae I, II, Ia, Ib, Ic, Id, Ia, IIb or IIc can be used as synthesis intermediates for the preparation of other compounds, in particular of other pharmaceutical active ingredients, which are obtainable from the compounds of the formulae I, II, Ia, Ib, Ic, Id, IIa, IIb or IIc, for example by introduction of substituents or modification of functional groups.

The general synthetic sequences for preparing the compounds useful in the present invention our outlined in the examples given below. Both an explanation of, and the actual procedure for, the various aspects of the present invention are described where appropriate. The following examples are intended to be merely illustrative of the present invention, and not limiting thereof in either scope or spirit. Those with skill in the art will readily understand that known variations of the conditions and processes described in the examples can be used to synthesize the compounds of the present invention.

It is understood that changes that do not substantially affect the activity of the various embodiments of this invention are included within the invention disclosed herein. Thus, the following examples are intended to illustrate but not limit the present invention.

EXAMPLES

When in the final step of the synthesis of a compound an acid such as trifluoroacetic acid or acetic acid was used, for example when trifluoroacetic acid was employed to remove a tBu group or when a compound was purified by chromatography using an eluent which contained such an acid, in some cases, depending on the work-up procedure, for example the details of a freeze-drying process, the compound was obtained partially or completely in the form of a salt of the acid used, for example in the form of the acetic acid salt or trifluoroacetic acid salt or hydrochloric acid salt.

Abbreviations Used:

As used throughout the description of the invention, the following terms, unless otherwise indicated, shall be understood to have the following meanings.

| | |
|---|---|
| tert-Butyl | tBu |
| 2,2'-bis(diphenylphoshino-1,1'-binaphthyl | Binap |
| Bis-(oxo-3-oxazolidinyl)-phosphoryl chloride | BOP-Cl |
| dibenzylidenacetone | dba |
| Dichloromethane | DCM |
| Dicyclohexyl-carbodiimide | DCC |
| Diethylphosphoryl cyanide | DEPC |
| Diisopropylethyl amine | DIPEA |
| 4-Dimethyaminopyridine | DMAP |
| N,N-Dimethylformamide | DMF |
| Dimethylsulfoxide | DMSO |
| 1,1'-Bis(diphenylphosphino)ferrocene | DPPF |
| O-(7-Azabenzotriazol-1-yl)-N,N,N',N'-tetramethyluronium-hexafluorophosphate | HATU |
| N-Bromosuccinimide | NBS |
| N-Chlorosuccinimide | NCS |
| N-Iodosuccinimide | NIS |
| N-Ethylmorpholine | NEM |
| Methanol | MeOH |
| Room temperature 20° C. to 25° C. | RT |
| Saturated | sat. |
| Tetrahydrofuran | THF |

-continued

| Trifluoroacetic acid | TFA |
|---|---|
| O-((Ethoxycarbonyl)cyanomethyleneamino)-N,N,N',N'-tetramethyluronium tetrafluoroborate | TOTU |

Example 1

1-[5-(5-Chloro-thiophen-2-yl)-isoxazol-3-ylmethyl]-5-pyrrol-1-yl-1H-[1,2,4]triazole-3-carboxylic acid (1-isopropyl-piperidin-4-yl)-amide (i) (1-Isopropyl-piperidin-4-yl)-carbamic acid tert-butyl ester To a solution of 5.0 g Piperidin-4-yl-carbamic acid tert-butyl ester in 15 ml methanol 7.34 ml acetone, 3.14 g Na(CN)BH$_3$ and 0.3 ml acetic acid were added. After stirring for 16 h at RT the solvent was removed under reduced pressure and the residue was partitioned between 30 ml of water and 30 ml of ethyl acetate. The organic layer was washed with saturated Na$_2$CO$_3$ solution, water and then dried over Na$_2$SO$_4$. Following filtration, the solvent was removed under reduced pressure to yields a white solid. Yield: 4.8 g. MS (ES$^+$): m/e=243.

(ii) 1-Isopropyl-piperidin-4-ylamine

To 4.8 g (1-Isopropyl-piperidin-4-yl)-carbamic acid tert-butyl ester in 15 ml methanol, 20 ml methanolic hydrochloric acid (8M) were added and the mixture was stirred for 16 h. Removal of the solvent under reduced pressure yielded a white solid, which was coevaporated twice with 20 ml toluene. The product was obtained as its hydrochloride. Yield: 5.42 g. MS (ES$^+$): m/e=143.

(iii) 5-Pyrrol-1-yl-1H-[1,2,4]triazole-3-carboxylic acid (1-isopropyl-piperidin-4-yl)-amide To 100 mg 5-Pyrrol-1-yl-1H-[1,2,4]triazole-3-carboxylic acid in 1 ml DMF and 0.3 ml NEt$_3$, 121 mg 1-Isopropyl-piperidin-4-ylamine dihydrochloride and 142 mg BOP-Cl were added at RT and the mixture was stirred for 16 h. After addition of 5 ml of water the mixture was filtered through a chem elut® cartridge by elution with ethyl acetate and then concentrated under reduced pressure. The obtained crude product was used without further purification in the next reaction step. Yield: 170 mg.

(iv) 1-[5-(5-Chloro-thiophen-2-yl)-isoxazol-3-ylmethyl]-5-pyrrol-1-yl-1H-[1,2,4triazole-3-carboxylic acid (1-isopropyl-piperidin-4-yl)-amide To a solution of 170 5-Pyrrol-1-yl-1H-[1,2,4]triazole-3-carboxylic acid (1-isopropyl-piperidin-4-yl)-amide in 1 ml DMF, 156 mg 3-Bromomethyl-5-(5-chloro-thiophen-2-yl)-isoxazole [prepared by adopting a procedure described by Ewing, William R.; Becker, Michael R.; Choi-Sledeski, Yong Mi; Pauls, Heinz W.; He, Wei; Condon, Stephen M.; Davis, Roderick S.; Hanney, Barbara A.; Spada, Alfred P.; Burns, Christopher J.; Jiang, John Z.; Li, Aiwen; Myers, Michael R.; Lau, Wan F.; Poli, Gregory B; PCT Int. Appl. (2001) 460 pp. WO 0107436 A2] and 183 mg Cs$_2$CO$_3$ were added and the mixture was stirred at room temperature for 1.5 h. After the addition of 2 ml sat. NaHCO$_3$ the mixture was filtered through a chem elut® cartridge by elution with ethyl acetate and then concentrated under reduced pressure. The residue was purified by preparative HPLC (C18 reverse phase column, elution with a H$_2$O/MeCN gradient with 0.1% TFA). The fractions containing the product were evaporated and lyophilized to yield a white solid. The product was obtained as its trifluoroacetate salt. Yield: 42 mg. MS (ES$^+$): m/e=500, chloro pattern.

Example 2

1-[5-(5-Chloro-thiophen-2-yl)-isoxazol-3-ylmethyl]-5-pyridin-2-yl-1H-[1,2,4]triazole-3-carboxylic acid (1-isopropyl-piperidin-4-yl)-amide The title compound was prepared analogously to example 1 with the difference that 5-Pyridin-2-yl-1H-[1,2,4]triazole-3-carboxylic acid was used instead of 5-Pyrrol-1-yl-1H-[1,2,4]triazole-3-carboxylic acid. MS (ES$^+$): m/e=512, chloro pattern.

Example 3

2-[5-(5-Chloro-thiophen-2-yl)-isoxazol-3-ylmethyl]-5-pyridin-2-yl-2H-[1,2,4]triazole-3-carboxylic acid (1-isopropyl-piperidin-4-yl)-amide This compound was isolated as a by-product from example 2. MS (ES$^+$): m/e=512, chloro pattern.

Example 4

1-[5-(5-Chloro-thiophen-2-yl)-isoxazol-3-ylmethyl]-5-phenyl-1H-[1,2,4]triazole-3-carboxylic acid (1-isopropyl-piperidin-4-yl)-amide The title compound was prepared analogously to example 1 with the difference that 5-Phenyl-1H-[1,2,4]triazole-3-carboxylic acid was used instead of 5-Pyrrol-1-yl-1H-[1,2,4]triazole-3triazole-3-carboxylic acid. MS (ES$^+$): m/e=511, chloro pattern.

Example 5

2-[5-(5-Chloro-thiophen-2-yl)-isoxazol-3-ylmethyl]-2H-tetrazole-5-carboxylic acid (1-isopropyl-piperidin-4-yl)-amide (i) 2-[5-(5-Chloro-thiophen-2-yl)-isoxazol-3-ylmethyl]-2H-tetrazole-5-carboxylic acid To a solution of 100 mg 2H-Tetrazole-5-carboxylic acid ethyl ester sodium salt in 1 ml DMF, 59 mg 3-Bromomethyl-5-(5-chloro-thiophen-2-yl)-isoxazole [prepared by adopting a procedure described by Ewing, William R.; Becker, Michael R.; Choi-Sledeski, Yong Mi; Pauls, Heinz W.; He, Wei; Condon, Stephen M.; Davis, Roderick S.; Hanney, Barbara A.; Spada, Alfred P.; Burns, Christopher J.; Jiang, John Z.; Li, Aiwen; Myers, Michael R.; Lau, Wan F.; Poli, Gregory B; PCT Int. Appl. (2001) 460 pp. WO 0107436 A2] were added and the mixture was stirred at room temperature for 16 h. Then the reaction mixture was concentrated under reduced pressure. The residue was taken-up in 1 ml THF and after addtion of 1 ml of a 1M NaOH solution stirred for 16 h at RT. The mixture was acidified with half concentrated hydrochloric acid to pH 3 and the precipitate collected by filtration. The product was obtained as a white solid, which was dried under reduced pressure. Yield: 49 mg.

(ii) 2-[5-(5-Chloro-thiophen-2-yl)-isoxazol-3-ylmethyl]-2H-tetrazole-5-carboxylic acid (1-isopropyl-piperidin-4-yl)-amide To a solution of 49 mg 2-[5-(5-Chloro-thiophen-2-yl)-isoxazol-3-ylmethyl]-2H-tetrazole-5-carboxylic acid, 0.1 ml N-NEM in 1 ml DCM, 53 mg TOTU were added and the mixture was stirred for 5 min at RT. Then 34 mg 1-Isopropyl-piperidin-4-ylamine hydrochloride were added and the reaction was further stirred for 2 h. The reaction mixture was concentrated under reduced pressure and the residue was directly purified by preparative HPLC (C18 reverse phase column, elution with a H₂O/MeCN gradient with 0.1% TFA). The fractions containing the product were evaporated and lyophilized to yield a white solid. The product was obtained as its trifluoroacetate salt. Yield: 18 mg. MS (ES⁺): m/e=436, chloro pattern.

Experimentals

Pharmacological Testing

The ability of the compounds of the formula I or II to inhibit factor Xa or factor VIIa or other enzymes like thrombin, plasmin, or trypsin can be assessed by determining the concentration of the compound of the formula I or II that inhibits enzyme activity by 50%, i.e. the IC50 value, which was related to the inhibition constant Ki. Purified enzymes were used in chromogenic assays. The concentration of inhibitor that causes a 50% decrease in the rate of substrate hydrolysis was determined by linear regression after plotting the relative rates of hydrolysis (compared to the uninhibited control) versus the log of the concentration of the compound of formulae I, II, Ia, Ib, Ic, Id, IIa, IIb or IId. For calculating the inhibition constant Ki, the IC50 value was corrected for competition with substrate using the formula $$Ki = IC50/\{1 + (\text{substrate concentration}/Km)\}$$

wherein Km is the Michaelis-Menten constant (Chen and Prusoff, Biochem. Pharmacol. 22 (1973) 3099–3108; I. H. Segal, Enzyme Kinetics, 1975, John Wiley & Sons, New York, 100–125; which were incorporated herein by reference).

a) Factor Xa Assay

In the assay for determining the inhibition of factor Xa activity TBS-PEG buffer (50 mM Tris-HCl, pH 7.8, 200 mM NaCl, 0.05% (w/v) PEG-8000, 0.02% (w/v) NaN3) was used. The IC50 was determined by combining in appropriate wells of a Costar half-area microtiter plate 25 µl human factor Xa (Enzyme Research Laboratories, Inc.; South Bend, Ind.) in TBS-PEG; 40 µl 10% (v/v) DMSO in TBS-PEG (uninhibited control) or various concentrations of the compound to be tested diluted in 10% (v/v) DMSO in TBS-PEG; and substrate S-2765 (N((α)-benzyloxycarbonyl-D-Arg-Gly-L-Arg-p-nitroanilide; Kabi Pharmacia, Inc.; Franklin, Ohio) in TBS-PEG.

The assay was performed by pre-incubating the compound of formula I or II plus enzyme for 10 min. Then the assay was initiated by adding substrate to obtain a final volume of 100 µl. The initial velocity of chromogenic substrate hydrolysis was measured by the change in absorbance at 405 nm using a Bio-tek Instruments kinetic plate reader (Ceres UV900HDi) at 25° C. during the linear portion of the time course (usually 1.5 min after addition of substrate). The enzyme concentration was 0.5 nM and substrate concentration was 140 µM.

b) Factor VIIa Assay

The inhibitory activity towards factor VIIa/tissue factor activity was determined using a chromogenic assay essentially as described previously (J. A. Ostrem et al., Biochemistry 37 (1998) 1053–1059 which was incorporated herein by reference). Kinetic assays were conducted at 25° C. in half-area microtiter plates (Costar Corp., Cambridge, Mass.) using a kinetic plate reader (Molecular Devices Spectramax 250). A typical assay consisted of 25 µl human factor VIIa and TF (5 nM and 10 nM, respective final concentration) combined with 40 µl of inhibitor dilutions in 10% DMSO/TBS-PEG buffer (50 mM Tris, 15 mM NaCl, 5 mM CaCl₂, 0.05% PEG 8000, pH 8.15). Following a 15 minute preincubation period, the assay was initiated by the addition of 35 µl of the chromogenic substrate S-2288 (D-Ile-Pro-Arg-p-nitroanilide, Pharmacia Hepar Inc., 500 µM final concentration). The results (inhibition constants Ki (FXa) for inhibition of factor Xa) are shown in Table 1.

TABLE 1

| Example | Ki(FXa) [µM] | Example | Ki(FXa) [µM] |
|---------|--------------|---------|--------------|
| 1 | 0.054 | 3 | 0.100 |
| 2 | 0.080 | 5 | 0.330 |

We claim:
1. A compound of the formula II,

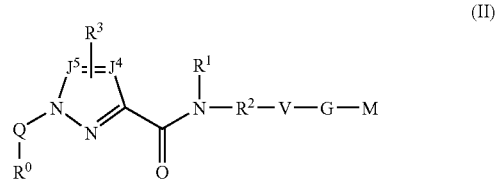

wherein J⁴ is N and J⁵ is C;
R⁰ is a monocyclic or bicyclic 4- to 15-membered heterocyclyl, containing one, two, three or four heteroatoms chosen from nitrogen, sulfur or oxygen, that is unsubstituted, mono-, di or trisubstituted independently of one another by R8, and the said monocyclic or bicyclic 4- to 15-membered heterocyclyl is additionally substituted by a monocyclic or bicyclic 4- to 15-membered heterocyclyl, containing one, two, three or four heteroatoms chosen from nitrogen, sulfur or oxygen the latter said monocyclic or bicyclic 4- to 15-membered heterocyclyl is unsubstituted or mono-, di- or trisubstituted independently of one another by R8;
R8 is 1) halogen,
2) —NO₂,
3) —CN,
4) —C(O)—NH₂,
5) —OH,
6) —NH₂,
7) —O—CF₃,
8) a monocyclic or bicyclic 6- to 14-membered aryl, that is mono-, di- or trisubstituted independently of one another by halogen or —O—(C₁–C₈)-alkyl,
9) —(C₁–C₈)-alkyl, that is unsubstituted or mono-, di- or trisubstituted independently of one another by halogen, NH₂, —OH or a methoxy group,
10) —O—(C₁–C₈)-alkyl, wherein alkyl is unsubstituted or mono-, di- or trisubstituted independently of one another by halogen, NH₂, —OH or a methoxy group,
11) —SO₂—CH₃ or
12) —SO₂—CF₃;
Q is a direct bond or —(C₁–C₆)-alkylene;
R¹ is hydrogen, —(C₁–C₄)-alkyl, that is unsubstituted or substituted one to three times by R13, —(C₁–C₃)-alkylene-C(O)—NH—R⁰, —(C₁–C₃)-alkylene-C(O)—O—R¹⁵, a monocyclic or bicyclic 6- to 14-membered aryl, that is mono-, di- or trisubstituted independently of one another by R8, a monocyclic or bicyclic 4- to 15-membered heterocyclyl, containing one, two, three or four heteroatoms chosen from nitrogen, sulfur or oxygen, —($C_1$–$C_3$)-perfluoroalkylene, —($C_1$–$C_3$)-alkylene-S(O)—($C_1$–$C_4$)-alkyl, —($C_1$–$C_3$)-alkylene-S(O)$_2$—($C_1$–$C_3$)-alkyl, —($C_1$–$C_3$)-alkylene-S(O)$_2$—N($R^{4'}$)—$R^{5'}$, —($C_1$–$C_3$)-alkylene-O—($C_1$–$C_3$)-alkyl, —($C_0$–$C_3$)-alkylene-($C_3$–$C_8$)-cycloalkyl, or —($C_0$–$C_3$)-alkylene-het, wherein het is a 3- to 7-membered cyclic residue, containing up to 1, 2, 3 or 4 heteroatoms chosen from nitrogen, sulfur or oxygen, that is unsubstituted, mono-, di- or trisubstituted independently of one another by R14;

$R^{4'}$ and $R^{5'}$ are independent of one another are identical or different and are hydrogen or —($C_1$–$C_4$)-alkyl;

$R^2$ is a direct bond or —($C_1$–$C_4$)-alkylene;

$R^1$ and $R^3$ together with the atoms to which they are bonded optionally form a 6- to 8-membered cyclic group, containing one, two, three or four heteroatoms chosen from nitrogen, sulfur and oxygen, and wherein, the cyclic group is unsubstituted, mono-, di- or trisubstituted independently of one another by R14; or $R^1$—N—$R^2$—V optionally form a 4- to 8-membered cyclic group, containing 1, 2, 3 or 4 heteroatoms chosen from nitrogen, sulfur or oxygen, wherein the cyclic group is unsubstituted, mono-, di- or trisubstituted independently of one another by R14;

R14 is halogen, —OH, =O, —($C_1$–$C_8$)-alkyl, —($C_1$–$C_4$)-alkoxy, —NO$_2$, —C(O)—OH, —CN, —NH$_2$, —C(O)—O—($C_1$–$C_4$)-alkyl, —($C_0$–$C_8$)-alkyl-SO$_2$—($C_1$–$C_4$)-alkyl, —($C_0$–$C_8$)-alkyl-SO$_2$—($C_1$–$C_3$)-perfluoroalkyl, —($C_0$–$C_8$)-alkyl-SO$_2$—N($R^{18}$)—$R^{21}$, —C(O)—NH—($C_1$–$C_8$)-alkyl, —C(O)—N—[($C_1$–$C_8$)-alkyl]$_2$, —$NR^{18}$—C(O)—NH—($C_1$–$C_8$)-alkyl, —C(O)—NH$_2$, —S—$R^{18}$, or —$NR^{18}$—C(O)—NH—[($C_1$–$C_8$)-alkyl]$_2$, wherein $R^{18}$ and $R^{21}$ are independently from each other hydrogen, —($C_1$–$C_3$)-perfluoroalkyl or —($C_1$–$C_6$)-alkyl, V is 1) a 3- to 7-membered cyclic residue, containing one, two, three or four heteroatoms chosen from nitrogen, sulfur or oxygen, wherein the cyclic residue is unsubstituted, mono-, di- or trisubstituted independently of one another by R14,
  2) a 6- to 14-membered aryl, that is unsubstituted, mono-, di- or trisubstituted independently of one another by R14, or
  3) a monocyclic or bicyclic 4- to 15-membered heterocyclyl, that is unsubstituted, mono-, di- or trisubstituted independently of one another by R14;

G is a direct bond, —(CH$_2$)$_m$—$NR^{10}$—SO$_2$—$NR^{10}$—(CH$_2$)$_n$—, —(CH$_2$)$_m$—CH(OH)—(CH$_2$)$_n$—, —(CH$_2$)$_m$—, —(CH$_2$)$_m$—O—(CH$_2$)$_n$—, —(CH$_2$)$_m$—C(O)—$NR^{10}$—(CH$_2$)$_n$—, —(CH$_2$)$_m$—SO$_2$—(CH$_2$)$_n$—, —(CH$_2$)$_m$—$NR^{10}$—C(O)—$NR^{10}$—(CH$_2$)$_n$—, —(CH$_2$)$_m$—$NR^{10}$—C(O)—(CH$_2$)$_n$—, —(CH$_2$)$_m$—C(O)—(CH$_2$)$_n$—, —(CH$_2$)$_m$—S—(CH$_2$)$_n$—, —(CH$_2$)$_m$—SO$_2$—$NR^{10}$—(CH$_2$)$_n$—, —(CH$_2$)$_m$—$NR^{10}$—SO$_2$—(CH$_2$)$_n$—, —(CH$_2$)$_m$—$NR^{10}$—, —(CH$_2$)$_m$—O—C(O)—$NR^{10}$—(CH$_2$)$_n$— or —(CH$_2$)$_m$—$NR^{10}$—C(O)—O—(CH$_2$)$_n$—;

n and m are independently of one another identical or different and are the integers zero, 1, 2, 3, 4, 5 or 6;

M is 1) hydrogen,
  2) —($C_1$–$C_8$)-alkyl, that is unsubstituted, mono-, di- or trisubstituted independently of one another by R14,
  3) —C(O)—N(R11)—R12,
  4) —(CH$_2$)$_m$—$NR^{10}$,
  5) a 6- to 14-membered aryl, that is unsubstituted, mono-, di- or trisubstituted independently of one another by R14,
  6) a monocyclic or bicyclic 4- to 15-membered heterocyclyl, that is unsubstituted, mono-, di- or trisubstituted independently of one another by R14,
  7) —($C_3$–$C_8$)-cycloalkyl, that is unsubstituted, mono-, di- or trisubstituted independently of one another by R14, or
  8) a 3- to 7-membered cyclic residue, containing one, two three or four heteroatoms chosen from nitrogen, sulfur or oxygen, wherein the cyclic residue is unsubstituted, mono-, di- or trisubstituted independently of one another by R14;

$R^3$ is
  1) hydrogen,
  2) halogen,
  3) —($C_1$–$C_4$)-alkyl, that is unsubstituted, mono-, di- or trisubstituted independently of one another by R13,
  4) —($C_1$–$C_3$)-perfluoroalkyl,
  5) phenyl, that is unsubstituted, mono-, di- or trisubstituted independently of one another by R13,
  6) —($C_0$–$C_4$)-alkylene-O—R19, wherein R19 is
    a) hydrogen,
    b) —($C_1$–$C_4$)-alkyl, that is unsubstituted, mono-, di- or trisubstituted independently of one another by R13,
    c) phenyl, that is unsubstituted, mono-, di- or trisubstituted independently of one another by R13,
    d) —CF$_3$ or
    e) —CHF$_2$,
  7) —NO$_2$,
  8) —CN,
  9) —SO$_s$—$R^{11}$, wherein s is 1 or 2,
  10) —SO$_t$—N($R^{11}$)—$R^{12}$, wherein t is 1 or 2,
  11) —($C_0$–$C_4$)-alkylene-C(O)—$R^{11}$,
  12) —($C_0$–$C_4$)-alkylene-C(O)—O—$R^{11}$,
  13) —($C_0$–$C_4$)-alkylene-C(O)—N($R^{11}$)—$R^{12}$,
  14) —($C_0$–$C_4$)-alkylene-N($R^{11}$)—$R^{12}$,
  15) —$NR^{10}$—SO$_2$—$R^{10}$,
  16) —S—$R^{10}$,
  17) —($C_0$–$C_2$)alkylene-C(O)—O—($C_2$–$C_4$)-alkylene-O—C(O)—($C_1$–$C_4$)-alkyl,
  18) —C(O)—O—C(R15, R16)—O—C(O)—R17,
  19) —($C_0$–$C_2$)alkylene-C(O)—O—($C_2$–$C_4$)-alkylene-O—C(O)—O—($C_1$–$C_6$)-alkyl,
  20) —C(O)—O—C(R15, R16)—O—C(O)—O—R17,
  21) —($C_0$–$C_4$)-alkylene-($C_6$–$C_{14}$)-aryl, wherein aryl is mono-, di- or trisubstituted independently of one another by R13,
  22) —($C_0$–$C_4$)-alkylene-($C_4$–$C_{15}$)-heterocyclyl, wherein heterocyclyl is unsubstituted or mono-, di- or trisubstituted independently of one another by R13
  23) —($C_0$–$C_4$)-alkylene-($C_3$–$C_8$)-cycloalkyl, wherein cycloalkyl is unsubstituted, mono-, di- or trisubstituted independently of one another by R13,
  24) —($C_0$–$C_4$)-alkylene-het, wherein het is unsubstituted or mono-, di- or trisubstituted independently of one another by R13,
  25) —($C_0$–$C_4$)-alkylene-O—CH$_2$—($C_1$–$C_3$)-perfluoroalkylene-CH$_2$—O—($C_0$–$C_4$)-alkyl,
  26) —SO$_w$—N($R^{11}$)—$R^{13}$, wherein w is 1 or 2,
  27) —($C_0$–$C_4$)-alkylene-C(O)—N($R^{11}$)—$R^{13}$,
  28) —($C_0$–$C_4$)-alkylene-N($R^{11}$)—$R^{13}$,
  29) =O or
  30) a residue from the following list

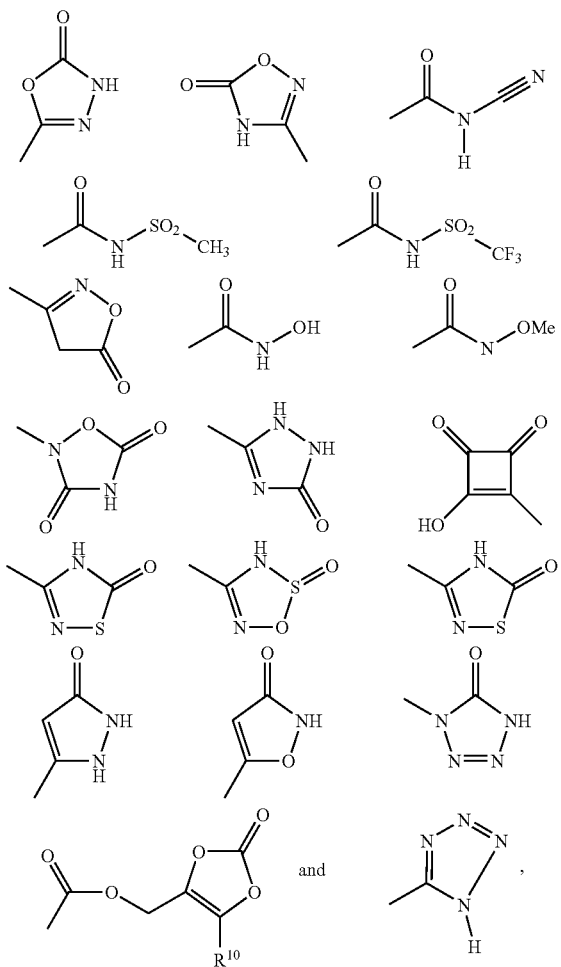

wherein Me is methyl, or if two —OR19 residues are attached to adjacent atoms they can form together with the atoms to which they are attached a 5- or 6-membered ring, that is unsubstituted or substituted one, two, three or four times by R13, provided that $R^3$ can be attached at any position on the ring of formulae I and II and can occur one, two or three times and is independently of one another identical or different, R11 and R12 are independently of one another identical or different and are
1) hydrogen,
2) —($C_1$–$C_6$)-alkyl, that is unsubstituted, mono-, di- or trisubstituted independently of one another by R13,
3) —($C_0$–$C_6$)-alkyl-($C_3$–$C_8$)-cycloalkyl,
4) —$SO_t$—$R^{10}$, wherein t is 1 or 2,
5) —($C_0$–$C_6$)-alkyl-($C_6$–$C_{14}$)-aryl, wherein alkyl and aryl independently from one another are unsubstituted or mono-, di- or trisubstituted by R13,
6) —($C_1$–$C_3$)-perfluoroalkyl,
7) —O—$R^{17}$, or
8) —($C_0$–$C_6$)-alkyl-($C_4$–$C_{15}$)-heterocyclyl, wherein alkyl and heterocyclyl independently from one another are unsubstituted, mono-, di- or trisubstituted by R13; or R11 and R12 together with the nitrogen atom to which they are bonded can form a 4- to 8-membered monocyclic heterocyclic ring which in addition to the nitrogen atom can contain one or two identical or different ring heteroatoms chosen from oxygen, sulfur and nitrogen, wherein the heterocyclic ring is unsubstituted, mono-, di- or trisubstituted independently of one another by R13;

R13 is halogen, —$NO_2$, —CN, =O, —OH, —$CF_3$, —C(O)—O—$R^{10}$, —C(O)—N($R^{10}$)—$R^{20}$, —N($R^{10}$)—$R^{20}$, —($C_3$–$C_8$)-cycloalkyl, —($C_0$–$C_3$)-alkylene-O—$R^{10}$, —Si—$(CH_3)_3$, —N($R^{10}$)—S(O)$_u$—$R^{10}$, wherein u is 1 or 2, —S—$R^{10}$, —$SO_r$—$R^{10}$, wherein r is 1 or 2, —S(O)$_v$—N($R^{10}$)—$R^{20}$, wherein v is 1 or 2, —C(O)—$R^{10}$, —($C_1$–$C_8$)-alkyl, —($C_1$–$C_8$)-alkoxy, phenyl, phenyloxy-, —O—$CF_3$, —($C_0$–$C_4$)-alkyl-C(O)—O—C(R15, R16)—O—C(O)—R17, —($C_1$–$C_4$)-alkoxy-phenyl, —($C_0$–$C_4$)-alkyl-C(O)—O—C(R15, R16)—O—C(O)—O—R17, —($C_1$–$C_3$)-perfluoroalkyl, —O—R15, —NH—C(O)—NH—$R^{10}$, —NH—C(O)—O—$R^{10}$, or a residue from the following list

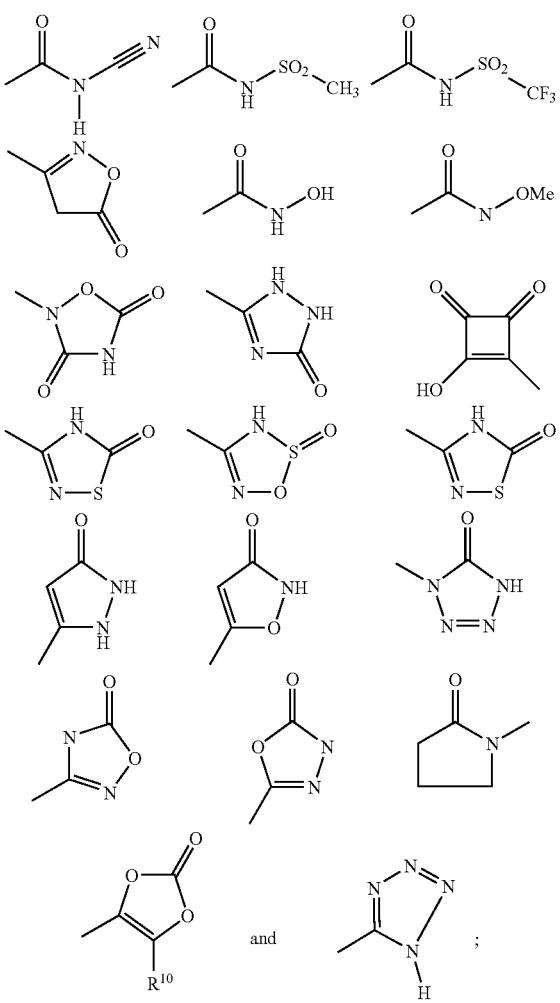

$R^{10}$ and $R^{20}$ are independently of one another hydrogen, —($C_1$–$C_6$)-alkyl, —($C_0$–$C_4$)-alkyl-OH, —($C_0$–$C_4$)-alkyl-O—($C_1$–$C_4$)-akyl or —($C_1$–$C_3$)-perfluoroalkyl;

R15 and R16 are independently of one another hydrogen, —($C_1$–$C_6$)-alkyl, or together with the carbon atom to which they are bonded they optionally form a 3- to 6 membered carbocyclic ring that is unsubstituted or substituted one to three times by $R^{10}$; and R17 is —$(C_1–C_6)$-alkyl —$(C_1–C_6)$-alkyl-OH, —$(C_1–C_6)$-alkyl-O—$(C_1–C_6)$-alkyl, —$(C_3–C_8)$-cycloalkyl, —$(C_1–C_6)$-alkyl-O—$(C_1–C_8)$-alkyl-$(C_3–C_8)$-cycloalkyl, —$(C_1–C_6)$-alkyl-$(C_3–C_8)$-cycloalkyl, wherein the ring is unsubstituted or substituted one, two or three times by —OH, —O—$(C_1–C_4)$-alkyl or $R^{10}$; or a stereoisomer or a mixture of stereoisomers in any ratio, or its physiologically tolerable salt.

2. The compound according to claim 1, wherein, $R_0$ is a monocyclic or bicyclic 4- to 15-membered heterocyclyl, containing one, two, three or four heteroatoms chosen from nitrogen, sulfur or oxygen, wherein said heterocyclyl is unsubstituted or mono-, di- or trisubstituted independently of one another by R8, and which is additionally substituted by a monocyclic or bicyclic 4- to 15-membered heterocyclyl, containing one, two, three or four hetereoatoms chosen from nitrogen, sulfur or oxygen, wherein heterocyclyl is unsubstituted, mono-, di- or trisubstituted independently of one another by R8;

M is 1) hydrogen,
2) —$(C_1–C_8)$-alkyl, that is unsubstituted, mono-, di- or trisubstituted independently of one another by R14,
3) —C(O)—N(R11)—R12,
4) —$(CH_2)_m$—$NR^{10}$,
5) —$(C_6–C_{14})$-aryl, that is unsubstituted, mono-, di- or trisubstituted independently of one another by R14,
6) —$(C_4–C_{15})$-heterocyclyl, that is unsubstituted, mono-, di- or trisubstituted independently of one another by R14,
7) —$(C_3–C_8)$-cycloalkyl, that is unsubstituted, mono-, di- or trisubstituted independently of one another by R14, or
8) a 3- to 7-membered cyclic residue, containing up to one, two, three or four heteroatoms chosen from nitrogen, sulfur or oxygen, wherein the cyclic residue is unsubstituted, mono-, di- or trisubstituted independently of one another by R14;

$R^3$ is
1) hydrogen,
2) halogen,
3) —$(C_1–C_4)$-alkyl, that is unsubstituted, mono-, di- or trisubstituted independently of one another by R13,
4) —$(C_1–C_3)$-perfluoroalkyl,
5) phenyl, that is unsubstituted, mono-, di- or trisubstituted independently of one another by R13,
6) —$(C_0–C_4)$-alkylene-O—R19, wherein R19 is
    a) hydrogen,
    b) —$(C_1–C_4)$-alkyl, that is unsubstituted, mono-, di- or trisubstituted independently of one another by R13,
    c) phenyl, that is unsubstituted, mono-, di- or trisubstituted independently of one another by R13,
    d) —$CF_3$ or
    e) —$CHF_2$,
7) —$NO_2$,
8) —CN,
9) —$SO_s$—$R^{11}$, wherein s is 1 or 2,
10) —$SO_t$—N($R^{11}$)—$R^{12}$, wherein t is 1 or 2,
11) —$(C_0–C_4)$-alkylene-C(O)—$R^{11}$,
12) —$(C_0–C_4)$-alkylene-C(O)—O—$R^{11}$,
13) —$(C_0–C_4)$-alkylene-C(O)—N($R^{11}$)—$R^{12}$,
14) —$(C_0–C_4)$-alkylene-N($R^{11}$)—$R^{12}$,
15) —$NR^{10}$—$SO_2$—$R^{10}$,
16) —S—$R^{10}$,
17) —$(C_0–C_2)$alkylene-C(O)—O—$(C_2–C_4)$-alkylene-O—C(O)—$(C_1–C_4)$-alkyl,
18) —C(O)—O—C(R15, R16)—O—C(O)—R17,
19) —$(C_0–C_2)$alkylene-C(O)—O—$(C_2–C_4)$-alkylene-O—C(O)—O—$(C_1–C_6)$-alkyl,
20) —C(O)—O—C(R15, R16)—O—C(O)—O—R17,
21) —$(C_0–C_4)$-alkylene-$(C_6–C_{14})$-aryl, wherein aryl is mono-, di- or trisubstituted independently of one another by R13,
22) —$(C_0–C_4)$-alkylene-$(C_4–C_{15})$-heterocyclyl, wherein heterocyclyl is unsubstituted, mono-, di- or trisubstituted independently of one another by R13,
23) —$(C_0–C_4)$-alkylene-$(C_3–C_8)$-cycloalkyl, wherein cycloalkyl is unsubstituted, mono-, di- or trisubstituted independently of one another by R13,
24) —$(C_0–C_4)$-alkylene-het, wherein het is unsubstituted, mono-, di- or trisubstituted independently of one another by R13,
25) —$(C_0–C_3)$-alkylene-O—$CH_2$—$(C_1–C_3)$-perfluoroalkylene-$CH_2$—O—$(C_0–C_3)$-alkyl,
26) —$SO_w$—N($R^{11}$)—$R^{13}$, wherein w is 1 or 2,
27) —$(C_0–C_4)$-alkylene-C(O)—N($R^{11}$)—$R^{13}$,
28) —$(C_0–C_4)$-alkylene-N($R^{11}$)—$R^{13}$, or
29) a residue from the following list

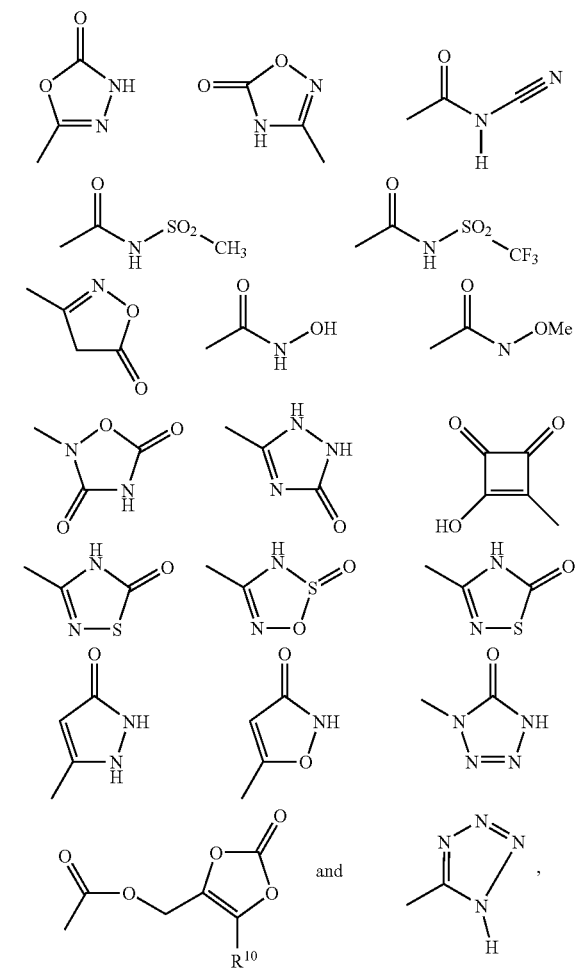

wherein Me is methyl, or if two —OR19 residues are attached to adjacent atoms they can form together with the atoms to which they are attached a 5- or 6-membered ring, that is unsubstituted or substituted one, two, three or four times by R13, provided that $R^3$ can be attached at any position on the ring of formulae I and II and can occur one, two or three times and is independently of one another identical or different; and $R^{10}$ and $R^{20}$ are independently of one another hydrogen, —$(C_1$–$C_6)$-alkyl or —$(C_1$–$C_3)$-perfluoroalkyl.

3. The compound according to claim 1, wherein, $R^0$ is acridinyl, azabenzimidazolyl, azaspirodecanyl, azepinyl, azetidinyl, aziridinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, carbazolyl, 4aH-carbazolyl, carbolinyl, chromanyl, chromenyl, cinnolinyl, decahydrochinolinyl, 4,5-dihydrooxa-zolinyl, dioxazolyl, dioxazinyl, 1,3-dioxolanyl, 1,3-dioxolenyl, 6H-1,5,2-dithiazinyl, dihydrofuro[2,3-b]-tetrahydrofuranyl, furanyl, furazanyl, imidazolidinyl, imidazolinyl, imidazolyl, 1H-indazolyl, indolinyl, indolizinyl, indolyl, 3H-indolyl, isobenzofuranyl, isochromanyl, isoindazolyl, isoindolinyl, isoindolyl, isoquinolinyl, isothiazolyl, isothiazolidinyl, isothiazolinyl, isoxazolyl, isoxazinyl, isoxazolidinyl, 2-isoxazolinyl, ketopiperazinyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, 1,2-oxa-thiepanyl, 1,2-oxathiolanyl, 1,4-oxazepanyl, 1,2-oxazinyl, 1,3-oxazinyl, 1,4-oxazinyl, oxazolidinyl, oxazolinyl, oxazolyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazolyl, pyridoimidazolyl, pyridothiazolyl, pyridyl, pyrimidinyl, pyrrolidinyl, pyrrolidinonyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, 1,4,5,6-tetrahydro-pyridazinyl, tetrahydropyridinyl, tetrahydrothiophenyl, tetrazinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, 1,2-thiazinyl, 1,3-thiazinyl, 1,4-thiazinyl, 1,3-thiazolyl, thiazolyl, thiazolidinyl, thiazolinyl, thienyl, thietanyl, thienothiazolyl, thienooxazolyl, thienoimidazolyl, thietanyl, thiomorpholinyl, thiophenolyl, thiophenyl, thiopyranyl, 1,2,3-triazinyl, 1,2,4-triazinyl, 1,3,5-triazinyl, 1,2,3-triazolyl, 1,2,4-triazolyl, 1,2,5-triazolyl, 1,3,4-triazolyl or xanthenyl, that is unsubstituted, mono-, di- or trisubstituted independently of one another by R8, and that is additionally substituted by acridinyl, azabenzimidazolyl, azaspirodecanyl, azepinyl, azetidinyl, aziridinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, carbazolyl, 4aH-carbazolyl, carbolinyl, chromanyl, chromenyl, cinnolinyl, decahydrochinolinyl, 4,5-dihydrooxa-zolinyl, dioxazolyl, dioxazinyl, 1,3-dioxolanyl, 1,3-dioxolenyl, 6H-1,5,2-dithiazinyl, dihydrofuro[2,3-b]-tetrahydrofuranyl, furanyl, furazanyl, imidazolidinyl, imidazolinyl, imidazolyl, 1H-indazolyl, indolinyl, indolizinyl, indolyl, 3H-indolyl, isobenzofuranyl, isochromanyl, isoindazolyl, isoindolinyl, isoindolyl, isoquinolinyl, isothiazolyl, isothiazolidinyl, isothiazolinyl, isoxazolyl, isoxazolinyl, isoxazolidinyl, 2-isoxazolinyl, ketopiperazinyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, 1,2-oxa-thiepanyl, 1,2-oxathiolanyl, 1,4-oxazepanyl, 1,2-oxazinyl, 1,3-oxazinyl, 1,4-oxazinyl, oxazolidinyl, oxazolinyl, oxazolyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazolyl, pyridoimidazolyl, pyridothiazolyl, pyridyl, pyrimidinyl, pyrrolidinyl, pyrrolidinonyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, 1,4,5,6-tetrahydro-pyridazinyl, tetrahydropyridinyl, tetrahydrothiophenyl, tetrazinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, 1,2-thiazinyl, 1,3-thiazinyl, 1,4-thiazinyl, 1,3-thiazolyl, thiazolyl, thiazolidinyl, thiazolinyl, thienyl, thietanyl, thienothiazolyl, thienooxazolyl, thienoimidazolyl, thietanyl, thiomorpholinyl, thiophenolyl, thiophenyl, thiopyranyl, 1,2,3-triazinyl, 1,2,4-triazinyl, 1,3,5-triazinyl, 1,2,3-triazolyl, 1,2,4-triazolyl, 1,2,5-triazolyl, 1,3,4-triazolyl or xanthenyl, that is unsubstituted, mono-, di- or trisubstituted independently of one another by R8;

$R^1$ is hydrogen, —$(C_1$–$C_4)$-alkyl, that is unsubstituted or substituted one to three times by R13, —$(C_1$–$C_3)$-alkylene-C(O)—NH—$R^0$, —$(C_1$–$C_3)$-alkylene-C(O)—O—R15, selected from phenyl, naphthyl, biphenylyl, anthryl or fluorenyl, wherein the aryl is mono-, di- or trisubstituted independently of one another by R8, a monocyclic or bicyclic 4- to 15-membered heterocyclyl, —$(C_1$–$C_3)$-perfluoroalkylene, —$(C_1$–$C_3)$-alkylene-S(O)—$(C_1$–$C_4)$-alkyl, —$(C_1$–$C_3)$-alkylene-S(O)$_2$—$(C_1$–$C_3)$-alkyl, —$(C_1$–$C_3)$-alkylene-S(O)$_2$—N($R^{4'}$)—$R^{5'}$, —$(C_1$–$C_3)$-alkylene-O—$(C_1$–$C_4)$-alkyl, —$(C_0$–$C_3)$-alkylene-$(C_3$–$C_8)$-cycloalkyl, or —$(C_0$–$C_3)$-alkylene-het, wherein het is a residue selected out of the group azepine, azetidine, aziridine, azirine, 1,4-diazepane, 1,2-diazepine, 1,3-diazepine, 1,4-diazepine, diaziridine, diazirine, dioxazole, dioxazine, dioxole, 1,3-dioxolene, 1,3-dioxolane, furan, imidazole, imidazoline, imidazolidine, isothiazole, isothiazolidine, isothiazoline, isoxazole, isoxazoline, isoxazolidine, 2-isoxazoline, ketopiperazine, morpholine, 1,4-oxazepane, 1,2-oxa-thiepane, 1,2-oxathiolane, 1,2-oxazine, 1,3-oxazine, 1,4-oxazine, oxazole, oxaziridine, oxirane, piperazine, piperidine, pyran, pyrazine, pyrazole, pyrazoline, pyrazolidine, pyridazine, pyridine, pyrimidine, pyrrole, pyrrolidine, pyrrolidinone, pyrroline, tetrahydropyridine, tetrazine, tetrazole, thiadiazine thiadiazole, 1,2-thiazine, 1,3-thiazine, 1,4-thiazine, 1,3-thiazole, thiazole, thiazolidine, thiazoline, thienyl, thietan, thiomorpholine, thiopyran, 1,2,3-triazine, 1,2,4-triazine, 1,3,5-triazine, 1,2,3-triazole or 1,2,4-triazole, wherein het is unsubstituted or mono-, di- or trisubstituted independently of one another by R14;

$R^1$ and R3 together with the atoms to which they are bonded optionally form a 6- to 8-membered cyclic residue selected from the group consisting of azocane, azocane-2-one, 1,2-diazepine, 1,3-diazepine, 1,4-diazepine, [1,4]diazocane, [1,2]diazocan-3-one, [1,3]diazocan-2-one, dioxazine, [1,4]dioxocane, dioxole, ketopiperazine, morpholine, 1,2-oxazine, 1,3-oxazine, 1,4-oxazine, oxocane, oxocan-2-one, piperazine, piperidine, pyran, pyrazine, pyridazine, pyrimidine and 5,6,7,8-tetrahydro-1H-azocin-2-one, that is unsubstituted, mono-, di- or trisubstituted independentlyl of one another by R14; or $R^1$—N—$R^2$—V optionally forms a 4- to 8-membered cyclic group selected from the group consisting of azepine, azetidine, dioxazole, dioxazine, 1,2-diazepine, 1,3-diazepine, 1,4-diazepine, imidazole, imidazoline, imidazolidine, isothiazole, isothiazolidine, isothiazoline, isoxazole, isoxazoline, isoxazolidine, 2-isoxazoline, ketopiperazine, morpholine, oxazole, piperazine, piperidine, pyrazine, pyrazole, pyrazoline, pyrazolidine, pyridazine, pyridine, pyrimidine, pyrrole, pyrrolidine, pyrrolidinone, pyrroline, tetrahydropyridine, tetrazine, tetrazole, thiazole, thiadiazole, thiazolidine, thiazoline, thiomorpholine, 1,2,3-triazine, 1,2,4-triazine, 1,3,5-triazine, 1,2,3-triazole and 1,2,4-triazole, that is unsubstituted mono-, di- or trisubstituted independently of one another by R14;

R14 as halogen is fluorine, chlorine, bromine, or iodine, —OH, =O, —($C_1$–$C_8$)-alkyl, —($C_1$–$C_4$)-alkoxy, —$NO_2$, —C(O)—OH, —CN, —$NH_2$, —C(O)—O—($C_1$–$C_4$)-alkyl, —($C_0$–$C_8$)-alkyl-$SO_2$-($C_1$–$C_4$)-alkyl, —($C_0$–$C_8$)-alkyl-$SO_2$—($C_1$–$C_3$)-perfluoroalkyl, —($C_0$–$C_8$)-alkyl-$SO_2$—N($R^{18}$)—$R^{21}$, —C(O)—NH—($C_1$–$C_8$)-alkyl, —C(O)—N—[($C_1$–$C_8$)-alkyl]$_2$, —$NR^{18}$—C(O)—NH—($C_1$–$C_8$)-alkyl, —C(O)—$NH_2$, —S—$R^{18}$, or —$NR^{18}$—C(O)—NH—[($C_1$–$C_8$)-alkyl]$_2$, wherein $R^{18}$ and $R^{21}$ are independently from each other hydrogen, —($C_1$–$C_3$)-perfluoroalkyl or —($C_1$–$C_6$)-alkyl;

V is
1) phenyl, naphthyl, biphenylyl, anthryl or fluorenyl, that is mono-, di- or trisubstituted independently of one another by R14,
2) acridinyl, azaindole 1H-pyrrolopyridine, azabenzimidazolyl, azaspirodecanyl, azepinyl, azetidinyl, aziridinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, carbazolyl, 4aH-carbazolyl, carbolinyl, chromanyl, chromenyl, cinnolinyl, decahydrochinolinyl, 1,4-diazepane, 4,5-dihydrooxa-zolinyl, dioxazolyl, dioxazinyl, 1,3-dioxolanyl, 1,3-dioxolenyl, 6H-1,5,2-dithiazinyl, dihydrofuro[2,3-b]-tetrahydrofuranyl, furanyl, furazanyl, imidazolidinyl, imidazolinyl, imidazolyl, 1H-indazolyl, indolinyl, indolizinyl, indolyl, 3H-indolyl, isobenzofuranyl, isochromanyl, isoindazolyl, isoindolinyl, isoindolyl, isoquinolinyl, isothiazolyl, isothiazolidinyl, isothiazolinyl, isoxazolyl, isoxazolinyl, isoxazolidinyl, 2-isoxazolinyl, ketopiperazinyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, 1,2-oxa-thiepanyl, 1,2-oxathiolanyl, 1,4-oxazepanyl, 1,2-oxazinyl, 1,3-oxazinyl, 1,4-oxazinyl, oxazolidinyl, oxazolinyl, oxazolyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazolyl, pyridoimidazolyl, pyridothiazolyl, pyridyl, pyrimidinyl, pyrrolidinyl, pyrrolidinonyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisochinolinyl, tetrahydrochinolinyl, 1,4,5,6-tetrahydro-pyridazinyl, tetrahydropyridinyl, tetrahydrothiophenyl, tetrazinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, 1,2-thiazinyl, 1,3-thiazinyl, 1,4-thiazinyl, 1,3-thiazolyl, thiazolyl, thiazolidinyl, thiazolinyl, thienyl, thietanyl, thienothiazolyl, thienooxazolyl, thienoimidazolyl, thietanyl, thiomorpholinyl, thiophenyl, thiopyranyl, 1,2,3-triazinyl, 1,2,3-triazolyl, 1,2,3-triazolyl, 1,2,4-triazolyl, 1,2,5-triazolyl, 1,3,4-triazolyl or xanthenyl, that is unsubstituted, mono-, di- or trisubstituted independently of one another by R14;

M is 1) hydrogen,
2) —($C_1$–$C_8$)-alkyl, that is unsubstituted, mono-, di- or trisubstituted independently of one another by R14,
3) —C(O)—N($R^{11}$)—$R^{12}$,
4) —($CH_2$)$_m$—$NR^{10}$,
5) —($C_6$–$C_{14}$)-aryl, that is unsubstituted, mono-, di- or trisubstituted independently of one another by R14,
6) —($C_4$–$C_{15}$)-heterocyclyl, that is unsubstituted, mono-, di- or trisubstituted independently of one another by R14, or
7) —($C_3$–$C_8$)-cycloalkyl, that is unsubstituted, mono-, di- or trisubstituted independently of one another by R14;

$R^3$ is
1) hydrogen,
2) halogen,
3) —($C_1$–$C_4$)-alkyl, that is unsubstituted, mono-, di- or trisubstituted independently of one another by R13,
4) —($C_1$–$C_3$)-perfluoroalkyl,
5) phenyl, that is unsubstituted, mono-, di- or trisubstituted independently of one another by R13,
6) —($C_0$–$C_4$)-alkylene-O—$R^{19}$, wherein $R^{19}$ is
   a) hydrogen,
   b) —($C_1$–$C_4$)-alkyl, that is unsubstituted, mono-, di- or trisubstituted independently of one another by R13,
   c) phenyl, that is unsubstituted, mono-, di- or trisubstituted independently of one another by R13,
   d) —$CF_3$ or
   e) —$CHF_2$,
7) —$NO_2$,
8) —CN,
9) —$SO_s$—$R^{11}$, wherein s is 1 or 2,
10) —$SO_t$—N($R^{11}$)—$R^{12}$, wherein t is 1 or 2,
11) —($C_0$–$C_4$)-alkylene-C(O)—$R^{11}$,
12) —($C_0$–$C_4$)-alkylene-C(O)—O—$R^{11}$,
13) —($C_0$–$C_4$)-alkylene-C(O)—N($R^{11}$)—$R^{12}$,
14) —($C_0$–$C_4$)-alkylene-N($R^{11}$)—$R^{12}$,
15) —$NR^{10}$—$SO_2$—$R^{10}$,
16) —S—$R^{10}$,
17) —($C_0$–$C_2$)alkylene-C(O)—O—($C_2$–$C_4$)-alkylene-O—C(O)—($C_1$–$C_4$)-alkyl,
18) —C(O)—O—C(R15, R16)—O—C(O)—R17,
19) —($C_0$–$C_2$)alkylene-C(O)—O—($C_2$–$C_4$)-alkylene-O—C(O)—O—($C_1$–$C_6$)-alkyl,
20) —C(O)—O—C(R15, R16)—O—C(O)—O—R17,
21) —($C_0$–$C_4$)-alkylene-($C_6$–$C_{14}$)-aryl, wherein aryl is mono-, di- or trisubstituted independently of one another by R13, 22) —(C₀–C₄)-alkylene-(C₄–C₁₅)-heterocyclyl, wherein heterocyclyl is unsubstituted, mono-, di- or trisubstituted independently of one another by R13,
23) —(C₀–C₄)-alkylene-(C₃–C₈)-cycloalkyl, wherein cycloalkyl is unsubstituted, mono-, di- or trisubstituted independently of one another by R13,
24) —(C₀–C₄)-alkylene-het, wherein het is unsubstituted, mono-, di- or trisubstituted independently of one another by R13,
25) —(C₀–C₄)-alkylene-O—CH₂—(C₁–C₃)-perfluoroalkylene-CH₂—O—(C₀–C₃)-alkyl,
26) —SO_w—N(R¹¹)—R¹³, wherein w is 1 or 2,
27) —(C₀–C₄)-alkylene-C(O)—N(R¹¹)—R¹³,
28) —(C₀–C₄)-alkylene-N(R¹¹)—R¹³, or
29) a residue from the following list

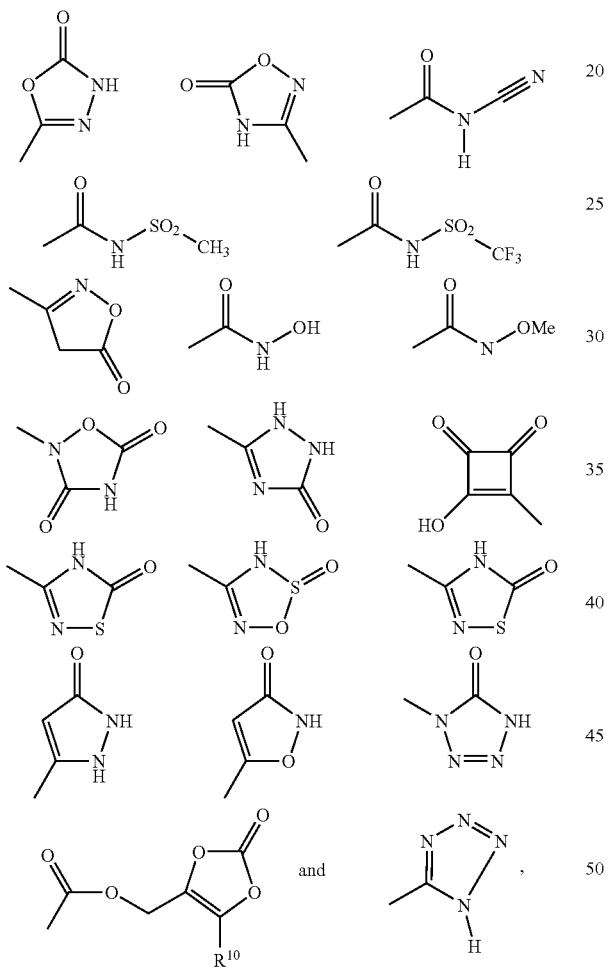

wherein Me is methyl, or if two —OR19 residues are attached to adjacent atoms they can form together with the atoms to which they are attached a 1,3-dioxole ring or a 2,3-dihydro-[1,4]dioxine ring, that is unsubstituted or substituted one, two, three of four times by R13,
provided that R³ is optionally attached at any position on the ring of formulae I or II and can occur one, two or three times, and is independently of one another identical or different; or
R¹¹ and R¹² together with the nitrogen to which they are bonded form a heterocyclic ring selected from the group consisting of azaspirodecan, azepine, azetidine, dioxazole, dioxazine, 1,4-diazepane, 1,2-diazepine, 1,3-diazepine, 1,4-diazepine, imidazole, imidazoline, imidazolidine, isothiazole, isothiazolidine, isothiazoline, isoxazole, isoxazoline, isoxazolidine, 2-isoxazoline, ketopiperazine, morpholine, [1,4]-oxazepane, oxazole, piperazine, piperidine, pyrazine, pyrazole, pyrazoline, pyrazolidine, pyridazine, pyridine, pyrimidine, pyrrole, pyrrolidine, pyrrolidinone, pyrroline, tetrahydropyridine, tetrazine, tetrazole, thiazole, thiadiazole, thiazolidine, thiazoline, thiomorpholine, thiophene, 1,2,3-triazine, 1,2,4-triazine, 1,3,5-triazine, 1,2,3-triazole or 1,2,4-triazole, that is unsubstituted, mono-, di- or trisubstituted independently of one another by R13; and R15 and R16 are independently of one another hydrogen, —(C₁–C₆)-alkyl, cyclopropyl, cyclobutyl, cyclopentyl or cyclohexyl, that is unsubstituted, substituted one to three times by R¹⁰.

4. The compound according to claim 1, wherein,
R⁰ is azabenzimidazolyl, benzimidazolyl, 1,3-benzodioxolyl, benzofuranyl, benzothiazolyl, benzothiophenyl, benzoxazolyl, chromanyl, cinnolinyl, 2-furyl, 3-furyl; imidazolyl, indolyl, indazolyl, isochromanyl, isoindolyl, isoquinolinyl, isothiazolyl, isoxazolyl, oxazolyl, phthalazinyl, pteridinyl, purinyl, pyrazinyl, pyrazolyl, pyridazinyl, pyridoimidazolyl, pyridopyridinyl, pyridopyrimidinyl, 2-pyridyl, 3-pyridyl, 4-pyridyl, pyrimidinyl, pyrrolyl; 2-pyrrolyl, 3-pyrrolyl, quinolinyl, quinazolinyl, quinoxalinyl, tetrazolyl, thiazolyl, 2-thienyl or 3-thienyl,
that is additionally substituted by acridinyl, azabenzimidazolyl, azaspirodecanyl, azepinyl, azetidinyl, aziridinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, carbazolyl, 4aH-carbazolyl, carbolinyl, chromanyl, chromenyl, cinnolinyl, decahydrochinolinyl, 4,5-dihydrooxa-zolinyl, dioxazolyl, dioxazinyl, 1,3-dioxolanyl, 1,3-dioxolenyl, 6H-1,5,2-dithiazinyl, dihydrofuro[2,3-b]-tetrahydrofuranyl, furanyl, furazanyl, imidazolidinyl, imidazolinyl, imidazolyl, 1H-indazolyl, indolinyl, indolizinyl, indolyl, 3H-indolyl, isobenzofuranyl, isochromanyl, isoindazolyl, isoindolinyl, isoindolyl, isoquinolinyl (benzimidazolyl), isothiazolyl, isothiazolidinyl, isothiazolinyl, isoxazolyl, isoxazolinyl, isoxazolidinyl, 2-isoxazolinyl, ketopiperazinyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, 1,2-oxa-thiepanyl, 1,2-oxathiolanyl, 1,4-oxazepanyl, 1,2-oxazinyl, 1,3-oxazinyl, 1,4-oxazinyl, oxazolidinyl, oxazolinyl, oxazolyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazolyl, pyridoimidazolyl, pyridothiazolyl, pyridyl, pyridyl, pyrimidinyl, pyrrolidinyl, pyrrolidinonyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydrochinolinyl, 1,4,5,6-tetrahydro-pyridazinyl, tetrahydropyridinyl, tetrahydrothiophenyl, tetrazinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, 1,2-thiazinyl, 1,3-thiazinyl, 1,4- thiazinyl, 1,3-thiazolyl, thiazolyl, thiazolidinyl, thiazolinyl, thienyl, thietanyl, thienothiazolyl, thienooxazolyl, thienoimidazolyl, thietanyl, thiomorpholinyl, thiophenyl, thiopyranyl, 1,2,3-triazinyl, 1,2,3-triazolyl, 1,2,3-triazolyl, 1,2,4-triazolyl, 1,2,5-triazolyl, 1,3,4-triazolyl or xanthenyl, that is unsubstituted or mono-, di- or trisubstituted independently of one another by R8;

R8 as
1) fluorine, chlorine or bromine,
2) —NO$_2$,
3) —CN,
4) —C(O)—NH$_2$,
5) —OH,
6) —NH$_2$,
7) —OCF$_3$,
8) a monocyclic or bicyclic 6- to 14-membered aryl, wherein aryl is as defined above and is mono-, di- or trisubstituted independently of one another by halogen or —O—(C$_1$–C$_8$)-alkyl,
9) —(C$_1$–C$_8$)-alkyl, wherein alkyl is unsubstituted or mono-, di- or trisubstituted independently of one another by halogen, NH$_2$, —OH or a methoxy residue, or
10) —O—(C$_1$–C$_8$)-alkyl, wherein alkyl is unsubstituted or mono-, di- or trisubstituted independently of one another by halogen, NH$_2$, —OH or a methoxy residue,
11) —SO$_2$CH$_3$, or
12) —SO$_2$CF$_3$;

Q is a direct bond or —(C$_0$–C$_6$)-alkylene;

R$^1$ is hydrogen, —(C$_1$–C$_4$)-alkyl, that is unsubstituted or substituted one to three times by R13, —(C$_1$–C$_3$)-alkylene-C(O)—NH—R$^0$, —(C$_1$–C$_3$)-alkylene-C(O)—O—R$^{15}$, —(C$_1$–C$_3$)-perfluoroalkylene, —(C$_1$–C$_3$)-alkylene-S(O)—(C$_1$–C$_4$)-alkyl, —(C$_1$–C$_3$)-alkylene-S(O)$_2$—(C$_1$–C$_3$)-alkyl, —(C$_1$–C$_3$)-alkylene-S(O)$_2$—N(R$^{4'}$)—R$^{5'}$, —(C$_1$–C$_3$)-alkylene-O—(C$_1$–C$_4$)-alkyl, —(C$_0$–C$_3$)-alkylene-(C$_3$–C$_8$)-cycloalkyl, or —(C$_0$–C$_3$)-alkylene-het, wherein het is a residue selected from the group consisting of azepine, azetidine, aziridine, azirine, 1,4-diazepane, 1,2-diazepine, 1,3-diazepine, 1,4-diazepine, diaziridine, diazirine, dioxazole, dioxazine, dioxole, 1,3-dioxolene, 1,3-dioxolane, furan, imidazole, imidazoline, imidazolidine, isothiazole, isothiazolidine, isothiazoline, isoxazole, isoxazoline, isoxazolidine, 2-isoxazoline, ketopiperazine, morpholine, 1,2-oxa-thiepane, 1,2-oxathiolane, 1,4-oxazepane, 1,2-oxazine, 1,3-oxazine, 1,4-oxazine, oxazole, oxaziridine, oxirane, piperazine, piperidine, pyran, pyrazine, pyrazole, pyrazoline, pyrazolidine, pyridazine, pyridine, pyrimidine, pyrrole, pyrrolidine, pyrrolidinone, pyrroline, tetrahydropyridine, tetrazine, tetrazole, thiadiazine thiadiazole, 1,2-thiazine, 1,3-thiazine, 1,4-thiazine, 1,3-thiazole, thiazole, thiazolidine, thiazoline, thienyl, thietan, thiomorpholine, thiopyran, 1,2,3-triazine, 1,2,4-triazine, 1,3,5-triazine, 1,2,3-triazole or 1,2,4-triazole, wherein het is unsubstituted, mono-, di- or trisubstituted independently of one another by R14, R$^1$—N—R$^2$—V can form a 4- to 8-membered cyclic group selected from the group consisting of azepine, azetidine, 1,4-diazepane, dioxazole, dioxazine, 1,2-diazepine, 1,3-diazepine, 1,4-diazepine, imidazole, imidazoline, imidazolidine, isothiazole, isothiazolidine, isothiazoline, isoxazole, isoxazoline, isoxazolidine, 2-isoxazoline, ketopiperazine, morpholine, 1,4-oxazepane, oxazole, piperazine, piperidine, pyrazine, pyrazole, pyrazoline, pyrazolidine, pyridazine, pyridine, pyrimidine, pyrrole, pyrrolidine, pyrrolidinone, pyrroline, tetrahydropyridine, tetrazine, tetrazole, thiazole, thiadiazole, thiazolidine, thiazoline, thiomorpholine, 1,2,3-triazine, 1,2,4-triazine, 1,3,5-triazine, 1,2,3-triazole and 1,2,4-triazole, that is unsubstituted, mono-, di- or trisubstituted independently of one another by R14;

R14 as halogen is fluorine, chlorine, bromine, or iodine, —OH, =O, —(C$_1$–C$_8$)-alkyl, —(C$_1$–C$_4$)-alkoxy, —NO$_2$, —C(O)—OH, —CN, —NH$_2$, —C(O)—O—(C$_1$–C$_4$)-alkyl, —(C$_0$–C$_8$)-alkyl-SO$_2$–(C$_1$–C$_4$)-alkyl, —(C$_0$–C$_8$)-alkyl-SO$_2$—(C$_1$–C$_3$)-perfluoroalkyl, —(C$_0$–C$_8$)-alkyl-SO$_2$—N(R$^{18}$)—R$^{21}$, —C(O)—NH—(C$_1$–C$_8$)-alkyl, —C(O)—N—[(C$_1$–C$_8$)-alkyl]$_2$, —NR$^{18}$—C(O)—NH—(C$_1$–C$_8$)-alkyl, —C(O)—NH$_2$, —S—R$^{18}$, or —NR$^{18}$—C(O)—NH—[(C$_1$–C$_8$)-alkyl]$_2$, wherein R$^{18}$ and R$^{21}$ are independently from each other hydrogen, —(C$_1$–C$_3$)-perfluoroalkyl or —(C$_1$–C$_6$)-alkyl;

V is
1) phenyl, that is unsubstituted, mono-, di- or trisubstituted independently of one another by R14, or
2) azaindole, 1H-pyrrolopyridine, azepine, azetidine, aziridine, azirine, 1,4-diazepane, 1,2-diazepane, 1,3-diazepine, 1,4-diazepine, diaziridine, diazirine, dioxazole, dioxazine, dioxole, 1,3-dioxolene, 1,3-dioxolane, furan, imidazole, imidazoline, imidazolidine, isothiazole, isothiazolidine, isothiazoline, isoxazole, isoxazoline, isoxazolidine, 2-isoxazoline, ketopiperazine, morpholine, 1,2-oxa-thiepane, 1,2-oxathiolane, 1,4-oxazepane, 1,2-oxazine, 1,3-oxazine, 1,4-oxazine, oxazole, oxaziridine, oxirane, piperazine, piperidine, pyran, pyrazine, pyrazole, pyrazoline, pyrazolidine, pyridazine, pyridine, pyrimidine, pyrrole, pyrrolidine, pyrrolidinone, pyrroline, tetrahydropyridine, tetrazine, tetrazole, thiadiazine, thiadiazole, 1,2-thiazine, 1,3-thiazine, 1,4-thiazine, 1,3-thiazole, thiazole, thiazolidine, thiazoline, thienyl, thietan, thiomorpholine, thiopyran, 1,2,3-triazine, 1,2,4-triazine, 1,3,5-triazine, 1,2,3-triazole or 1,2,4-triazole, which is as defined above and wherein het is unsubstituted or mono-, di- or trisubstituted independently of one another by R14;

M is
1) hydrogen,
2) —(C$_1$–C$_8$)-alkyl, that is unsubstituted, mono-, di- or trisubstituted independently of one another by R14,
3) —C(O)—N(R11)—R12,
4) —(CH$_2$)$_m$—NR$^{10}$,
5) phenyl or naphthyl, that is unsubstituted, mono-, di- or trisubstituted independently of one another by R14,
6) azepane, azepine, 1,4-diazepane, 1,2-diazepine, 1,3-diazepine, 1,4-diazepine, imidazole, isothiazole, isoxazole, isoxazolidine, 2-isoxazoline, ketomorpholine, ketopiperazine, morpholine, oxazole, [1,4]-oxazepane, piperazine, piperazinone, piperidine, piperidinone, pyrazine, pyridazine, pyridazinone, pyridine, pyridone, pyrimidine, pyrrolidine, pyrrolidinone, tetrahydropyran, 1,4,5,6-tetrahydro-pyridazinyl, tetrazine, tetrazole, thiadiazole, thiazole, thiophene, thiomorpholine, 1,2,3-triazine, 1,2,4-triazine, 1,3,5-triazine, 1,2,3-triazole or 1,2,4-triazole, that is unsubstituted, mono-, di- or trisubstituted independently of one another by R14, or
7) —(C$_3$–C$_8$)-cycloalkyl, that is unsubstituted, mono-, di- or trisubstituted independently of one another by R14;

R³ is
1) hydrogen,
2) halogen,
3) —(C₁–C₄)-alkyl, that is unsubstituted, mono-, di- or trisubstituted independently of one another by R13,
4) —(C₁–C₃)-perfluoroalkyl,
5) phenyl, that is unsubstituted, mono-, di- or trisubstituted independently of one another by R13,
6) —(C₀–C₄)-alkylene-O—R19, wherein R19 is
   a) hydrogen,
   b) —(C₁–C₄)-alkyl, that is unsubstituted, mono-, di- or trisubstituted independently of one another by R13, or
   c) phenyl, that is unsubstituted, mono-, di- or trisubstituted independently of one another by R13,
   d) —CF₃, or
   e) CHF₂,
7) —CN,
8) —SO$_s$—R¹¹, wherein s is 1 or 2,
9) —SO$_t$—N(R¹¹)—R¹², wherein t is 1 or 2,
10) —(C₀–C₄)-alkylene-C(O)—R¹¹,
11) —(C₀–C₄)-alkylene-C(O)—O—R¹¹,
12) —(C₀–C₄)-alkylene-C(O)—N(R¹¹)—R¹²,
13) —(C₀–C₄)-alkylene-N(R¹¹)—R¹²,
14) —NR¹⁰—SO₂—R¹⁰,
15) —(C₀–C₂)-alkylene-C(O)—O—(C₂–C₄)-alkylene-O—C(O)—(C₁–C₄)-alkyl,
16) —C(O)—O—C(R15, R16)—O—C(O)—R17,
17) —(C₀–C₂)alkylene-C(O)—O—(C₂–C₄)-alkylene-O—C(O)—O—(C₁–C₆)-alkyl,
18) —C(O)—O—C(R15, R16)—O—C(O)—O—R17,
19) —(C₀–C₄)-alkylene-(C₆–C₁₄)-aryl, wherein aryl is as defined above and is mono-, di- or trisubstituted independently of one another by R13,
20) —(C₀–C₄)-alkylene-(C₄–C₁₅)-heterocyclyl, wherein heterocyclyl is as defined above and is unsubstituted or mono-, di- or trisubstituted independently of one another by R13,
21) —(C₀–C₄)-alkylene-(C₃–C₈)-cycloalkyl, wherein cycloalkyl is unsubstituted or mono-, di- or trisubstituted independently of one another by R13,
22) —(C₀–C₄)-alkylene-het, wherein het is unsubstituted, mono-, di- or trisubstituted independently of one another by R13,
23) —(C₀–C₃)-alkylene-O—CH₂—CF₂—CH₂—O—(C₀–C₃)-alkyl, —(C₀–C₃)-alkylene-O—CH₂—CF₂—CF₂—CH₂—O—(C₀–C₃)-alkyl, or —(C₀–C₃)-alkylene-O—CH₂—(C₁–C₃)-perfluoro-alkylene-CH₂—OH,
24) —SO$_w$—N(R¹¹)—R¹³, wherein w is 1 or 2,
25) —(C₀–C₄)-alkylene-C(O)—N(R¹¹)—R¹³,
26) —(C₀–C₄)-alkylene-N(R¹¹)—R¹³, or
27) a residue from the following list

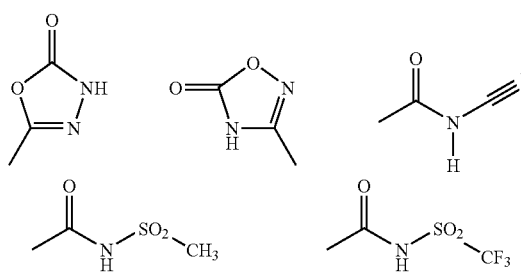

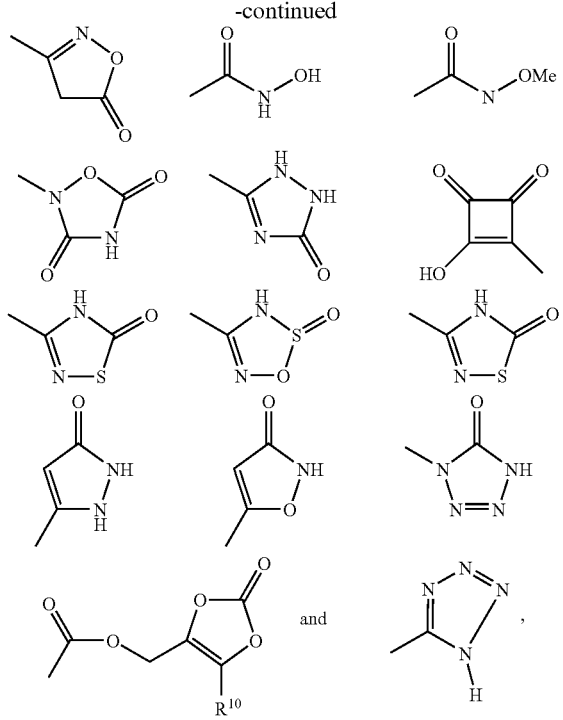

wherein Me is methyl, or if two —OR19 residues are attached to adjacent atoms they can form together with the atoms to which they are attached a 1,3-dioxole ring or a 2,3-dihydro-[1,4]dioxine ring, that is unsubstituted or substituted one, two, three or four times by R13, provided that R³ is optionally attached at any position on the ring of formulae I or II and can occur one, two or three times and is independently of one another identical or different, R11 and R12 are independently of one another identical or different and are
1) hydrogen,
2) —(C₁–C₆)-alkyl, that is unsubstituted, mono-, di- or trisubstituted independently of one another by R13,
3) —(C₀–C₆)-alkyl-(C₆–C₁₄)-aryl, wherein alkyl and aryl are independently from one another unsubstituted, mono-, di- or trisubstituted by R13,
4) —O—R¹⁷, or
5) —(C₀–C₆)-alkyl-(C₄–C₁₅)-heterocyclyl, wherein alkyl and heterocyclyl is independently from one another unsubstituted, mono-, di- or trisubstituted by R13, or R11 and R12 together to which they are bonded optionally form a ring selected out of the group azepine, azetidine, 1,4-diazepane, dioxazole, dioxazine, 1,2-diazepine, 1,3-diazepine, 1,4-diazepine, imidazole, imidazoline, imidazolidine, isothiazole, isothiazolidine, isothiazoline, isoxazole, isoxazoline, isoxazolidine, 2-isoxazoline, ketopiperazine, morpholine, [1,4]oxazepane, oxazole, piperazine, piperidine, pyrazine, pyrazole, pyrazoline, pyrazolidine, pyridazine, pyridine, pyrimidine, pyrrole, pyrrolidine, pyrrolidinone, pyrroline, tetrahydropyridine, tetrazine, tetrazole, thiazole, thiadiazole, thiazolidine, thiazoline, thiomorpholine, 1,2,3-triazine, 1,2,4-triazine, 1,3,5-triazine, 1,2,3-triazole or 1,2,4-triazole, that is unsubstituted, mono-, di- or trisubstituted independently of one another by R13;

R13 as halogen is fluorine, chlorine, bromine, or iodine, —NO$_2$, —CN, =O, —OH, —CF$_3$, —C(O)—O—R$^{10}$, —C(O)—N(R$^{10}$)—R$^{20}$, —N(R$^{10}$)—R$^{20}$, —(C$_0$–C$_3$)-alkylene-O—R$^{10}$, —Si—(CH$_3$)$_3$, —N(R$^{10}$)—S(O)$_2$—R$^{10}$, —S—R$^{10}$, —SO$_2$—R$^{10}$, —S(O)$_2$—N(R$^{10}$)—R$^{20}$, —C(O)—R$^{10}$, —(C$_1$–C$_8$)-alkyl, —(C$_1$–C$_8$)-alkoxy, phenyl, phenyloxy-, —O—CF$_3$, —(C$_1$–C$_3$)-perfluoroalkyl, —(C$_0$–C$_4$)-alkyl-C(O)—O—C(R15, R16)—O—C(O)—R17, —(C$_1$–C$_4$)-alkoxy-phenyl, —(C$_0$–C$_4$)-alkyl-C(O)—O—C(R15, R16)—O—C(O)—O—R17, —O—R15, —NH—C(O)—NH—R$^{10}$, —NH—C(O)—O—R$^{10}$, or a residue from the following list

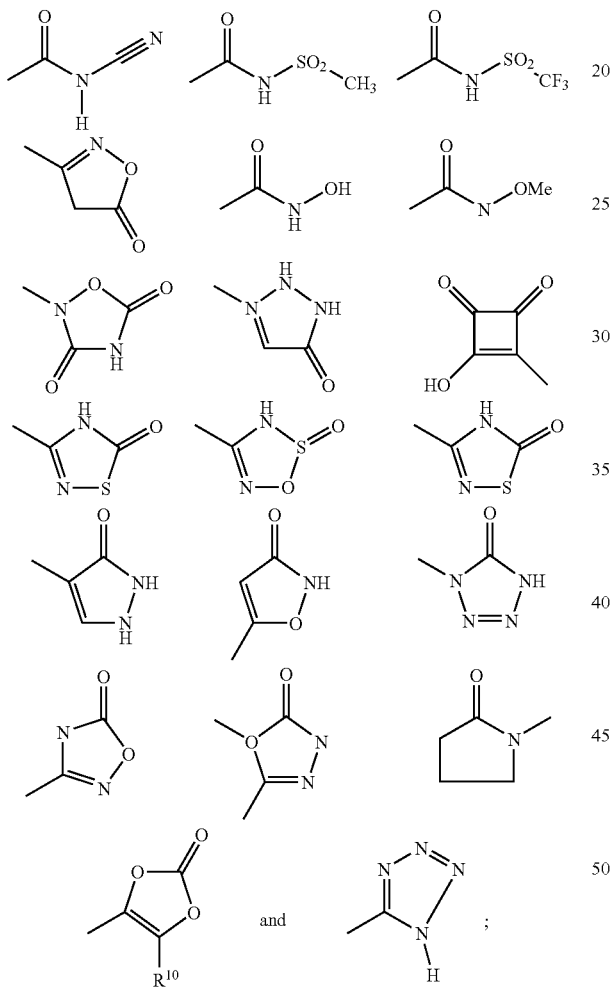

R15 and R16 are independently of one another hydrogen, —(C$_1$–C$_6$)-alkyl, or together form a ring selected from the group consisting of cyclopropyl, cyclobutyl, cyclopentyl and cyclohexyl, that is unsubstituted or substituted one to three times by R10.

5. The compound according to claim 1, wherein,

R0 is pyridyl, 2-pyridyl, 3-pyridyl, 4-pyridyl, pyrrolyl, 2-pyrrolyl, 3-pyrrolyl, furyl, 2-furyl, 3-furyl; thienyl, 2-thienyl, 3-thienyl, imidazolyl, pyrazolyl, oxazolyl, isoxazolyl, thiazolyl, thiadiazolyl, isothiazolyl, triazolyl, tetrazolyl, pyridazinyl or pyrazinyl, that is unsubstituted, mono-, di- or trisubstituted independently of one another by R8, and is additionally substituted by a residue selected from the group consisting of pyridyl, 2-pyridyl, 3-pyridyl, 4-pyridyl, pyrrolyl, 2-pyrrolyl, 3-pyrrolyl, furyl, 2-furyl, 3-furyl; thienyl, 2-thienyl, 3-thienyl, imidazolyl, pyrazolyl, oxazolyl, isoxazolyl, thiazolyl, thiadiazolyl, isothiazolyl, triazolyl, tetrazolyl, pyridazinyl and pyrazinyl, that is unsubstituted, mono-, di- or trisubstituted independently of one another by R8;

R8 is
1) F, Cl, Br or I,
2) —C(O)—NH$_2$,
3) —(C$_1$–C$_4$)-alkykl, that is unsubstituted, mono-, di- or trisubstituted independently of one another by halogen, —OH or a methoxy residue, or
4) —O—(C$_1$–C$_4$)-alkyl, that is unsubstituted, mono-, di- or trisubstitute independently of one another by halogen or a methoxy residue;

Q is a direct bond or —(C$_1$–C$_6$)-alkylene;

R$^1$ is hydrogen, —(C$_1$–C$_2$)-alkyl, —(C$_1$–C$_3$)-alkylene-C(O)—NH—R0, —(C$_1$–C$_3$)-perfluoroalkylene, —(C$_1$–C$_3$)-alkylene-C(O)—O—R$^{15}$, —(C$_1$–C$_3$)-alkylene-S(O)$_2$—(C$_1$–C$_3$)-alkyl or —(C$_1$–C$_3$)-alkylene-S(O)$_2$—N(R$^{4'}$)—R$^{5'}$;

R$^2$ is a direct bond or —(C$_1$–C$_2$)-alkylene;

R$^1$—N—R$^2$—V optionally form a 4- to 8-membered cyclic group selected from the group consisting of azetidine, azetidinone, piperidine, piperazine, pyridine, pyrimidine, pyrrolidine, pyrrolidinone, 1,2,3-triazine, 1,2,4-triazine, 1,3,5-triazine, 1,2,3-triazole, 1,2,4-triazole, tetrazine, tetrazole, 1,4-diazepane, 1,2-diazepine, 1,3-diazepine, 1,4-diazepine, azepine, ketopiperazine, 1,4-oxazepane, oxazole, isoxazole, isoxazolidine, 2-isoxazoline, morpholine, thiazole, isothiazole, thiadiazole and thiomorpholine, that is unsubstituted, mono-, di- or trisubstituted independently of one another by R14;

R14 is fluorine or chlorine, —OH, =O, —(C$_1$–C$_8$)-alkyl, —C(O)—OH, —CN, —NH$_2$, —C(O)—O—(C$_1$–C$_4$)-alkyl, —C(O)—NH—(C$_1$–C$_8$)-alkyl, —C(O)—N—[(C$_1$–C$_8$)-alkyl]$_2$, —C(O)—NH$_2$ or —N(R$^{18}$)—R$^{21}$, wherein R$^{18}$ and R$^{21}$ are independently from each other hydrogen, —(C$_1$–C$_3$)-perfluoroalkyl or —(C$_1$–C$_4$)-alkyl;

V is
1) azaindole, 1H-pyrrolopyridine, aziridine, azirine, azetidine, azetidinone, 1,4-diazepane, pyrrole, pyrrolidine, pyridonyl, imidazole, pyrazole, 1,2,3-triazole, 1,2,4-triazole, tetrazole, pyridine, pyrimidine, pyrazine, 1,2,3-triazine, 1,2,4-triazine, 1,3,5-triazine, tetrazine, tetrazole, azepine, diazirine, 1,2-diazepine, 1,3-diazepine, 1,4-diazepine, pyridazine, piperidine, piperazine, pyrrolidinone, ketopiperazine, furan, pyran, dioxole, 1,4-oxazepane, oxazole, isoxazole, 2-isoxazoline, isoxazolidine, morpholine, oxirane, oxaziridine, 1,3-dioxolene, 1,3-dioxolane, 1,2-oxazine, 1,3-oxazine, 1,4-oxazine, oxaziridine, thiophene, thiopyran, thietan, thiazole, isothiazole, isothiazoline, isothiazolidine, 1,2-oxathiolan, thiodiazole, thiopyran, 1,2-thiazine, 1,3-thiazole, 1,3-thiazine, 1,4-thiazine, thiadiazine or thiomorpholine, that is unsubstituted, mono-, di- or trisubstituted independently of one another by R14, or
2) phenyl, that is unsubstituted, mono-, di- or trisubstituted independently of one another by R14; or G is a direct bond, —(CH$_2$)$_m$—, or —(CH$_2$)$_m$—NR$^{10}$—;
m is the integer zero, 1, 2, 3 or 4;

M is
1) hydrogen,
2) —(C$_1$–C$_6$)-alkyl, that is unsubstituted, mono-, di- or trisubstituted independently of one another by R14,
3) —C(O)—N(R$^{11}$)—R$^{12}$,
4) heterocyclyl, that is selected from the group consisting of azepane, azepine, 1,4-diazepane, 1,2-diazepine, 1,3-diazepine, 1,4-diazepine, imidazole, isothiazole, isoxazole, isoxazolidine, 2-isoxazoline, ketomorpholine, ketopiperazine, morpholine, oxazole, [1,4]-oxazepane, piperazine, piperazinone, piperidine, piperidinone, pyrazine, pyridazine, pyridazinone, pyridine, pyridone, pyrimidine, pyrrolidine, pyrrolidinone, tetrahydropyran, 1,4,5,6-tetrahydro-pyridazinyl, tetrazine, tetrazole, thiadiazole, thiazole, thiomorpholine, thiophene, 1,2,3-triazine, 1,2,4-triazine, 1,3,5-triazine, 1,2,3-triazole or 1,2,4-triazole, that is unsubstituted, mono-, di- or trisubstituted independently of one another by R14, or
5) —(C$_3$–C$_6$)-cycloalkyl;

R$^3$ is
1) hydrogen,
2) halogen,
3) —(C$_1$–C$_4$)-alkyl, that is unsubstituted, mono-, di- or trisubstituted independently of one another by R13,
4) —(C$_1$–C$_3$)-perfluoroalkyl,
5) phenyl, that is unsubstituted, mono-, di- or trisubstituted independently of one another by R13,
6) —(C$_0$–C$_4$)-alkylene-O—R19, wherein R19 is
  a) hydrogen,
  b) —(C$_1$–C$_4$)-alkyl, that is unsubstituted, mono-, di- or trisubstituted independently of one another by R13,
  c) phenyl, that is unsubstituted, mono-, di- or trisubstituted independently of one another by R13,
  d) —CF$_3$ or
  e) —CHF$_2$,
7) —CN,
8) —SO$_s$—R$^{11}$, wherein s is 1 or 2,
9) —SO$_t$—N(R$^{11}$)—R$^{12}$, wherein t is 1 or 2,
10) —(C$_0$–C$_4$)-alkylene-C(O)—R$^{11}$,
11) —(C$_0$–C$_4$)-alkylene-C(O)—O—R$^{11}$,
12) —(C$_0$–C$_4$)-alkylene-C(O)—N(R$^{11}$)—R$^{12}$,
13) —(C$_0$–C$_4$)-alkylene-N(R$^{11}$)—R$^{12}$,
14) —NR$^{10}$—SO$_2$—R$^{10}$,
15) —(C$_0$–C$_2$)-alkylene-C(O)—O—(C$_2$–C$_4$)-alkylene-O—C(O)—(C$_1$–C$_4$)-alkyl,
16) —C(O)—O—C(R15, R16)—O—C(O)—R17,
17) —(C$_0$–C$_2$)alkylene-C(O)—O—(C$_2$–C$_4$)-alkylene-O—C(O)—O—(C$_1$–C$_6$)-alkyl,
18) —C(O)—O—C(R15, R16)—O—C(O)—O—R17,
19) —(C$_0$–C$_3$)-alkylene-(C$_3$–C$_6$)-cycloalkyl, wherein cycloalkyl is unsubstituted or mono-, di- or trisubstituted independently of one another by R13,
20) —(C$_0$–C$_3$)-alkylene-O—CH$_2$—CF$_2$—O—(C$_0$–C$_3$)-alkyl, —(C$_0$–C$_3$)-alkylene-O—CH$_2$—CF$_2$—CF$_2$—CH$_2$—O—(C$_0$–C$_3$)-alkyl, or —(C$_0$–C$_3$)-alkylene-O—CH$_2$—(C$_1$–C$_3$)-perfluoroalkylene-CH$_2$—OH,
21) —SO$_w$—N(R$^{11}$)—R$^{13}$, wherein w is 1 or 2,
22) —(C$_0$–C$_4$)-alkylene-C(O)—N(R$^{11}$)—R$^{13}$,
23) —(C$_0$–C$_4$)-alkylene-N(R$^{11}$)—R$^{13}$, or
24) a residue from the following list

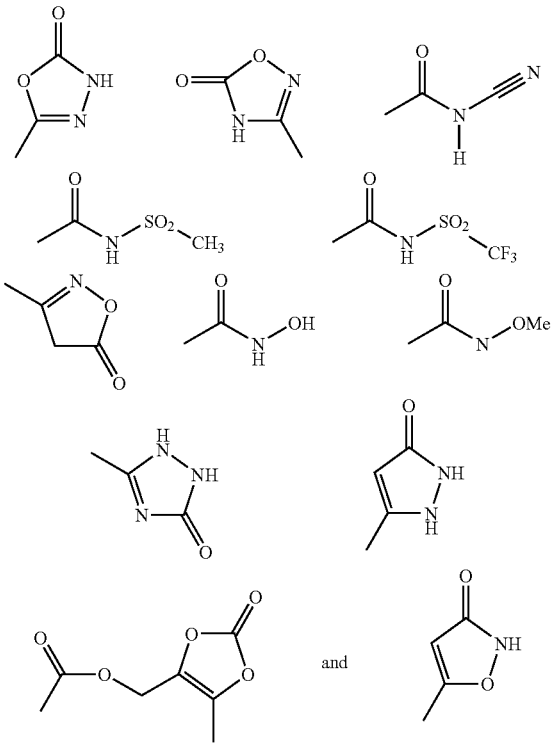

wherein Me is methyl, or if two —OR19 residues are attached to adjacent atoms they can form together with the atoms to which they are attached a 1,3-dioxole ring or a 2,3-dihydro-[1,4]dioxine ring, which is substituted one, two, three or four times by R13, provided that R$^3$ is optionally attached at any position on the ring of formula II;

R$^{11}$ and R$^{12}$ together with the nitrogen to which they are bonded optionally form a ring selected from the group consisting of azepine, azetidine, 1,4-diazepane, dioxazole, dioxazine, 1,2-diazepine, 1,3-diazepine, 1,4-diazepine, imidazole, imidazoline, imidazolidine, isothiazole, isothiazolidine, isothiazoline, isoxazole, isoxazoline, isoxazolidine, 2-isoxazoline, ketopiperazine, morpholine, [1,4]-oxazepane, oxazole, piperazine, piperidine, pyrazine, pyrazole, pyrazoline, pyrazolidine, pyridazine, pyridine, pyrimidine, pyrrole, pyrrolidine, pyrrolidinone, pyrroline, tetrahydropyridine, tetrazine, tetrazole, thiazole, thiadiazole, thiazolidine, thiazoline, thiomorpholine, thiophene, 1,2,3-triazine, 1,2,4-triazine, 1,3,5-triazine, 1,2,3-triazole and 1,2,4-triazole, that is unsubstituted, mono-, di- or trisubstituted independently of one another by R13;

R13 is fluorine or chlorine, —NO$_2$, —CN, =O, —OH, —CF$_3$, —C(O)—O—R$^{10}$, —C(O)—N(R$^{10}$)—R$^{20}$, —N(R$^{10}$)—R$^{20}$, —(C$_0$–C$_3$)-alkylene-O—R$^{10}$, —Si—(CH$_3$)$_3$, —N(R$^{10}$)—S(O)$_2$—R$^{10}$, —S—R$^{10}$, —SO$_2$—R$^{10}$, —S(O)$_2$—N(R$^{10}$)—R$^{20}$, —C(O)—R$^{10}$, —(C$_1$–C$_8$)-alkyl, —(C$_1$–C$_8$)-alkoxy, phenyl, phenyloxy-, —O—CF$_3$, —(C$_1$–C$_3$)-perfluoroalkyl, —NH—C(O)—NH—R$^{10}$, —(C$_0$–C$_4$)-alkyl-C(O)—O—C(R15, R16)—O—C(O)—R17, —(C$_1$–C$_4$)-alkoxy-phenyl, —(C$_0$–C$_4$)-alkyl-C(O)—O—C(R15, R16)—

O—C(O)—R17, —O—R15, —NH—C(O)—O—R¹⁰, or a residue from the following list

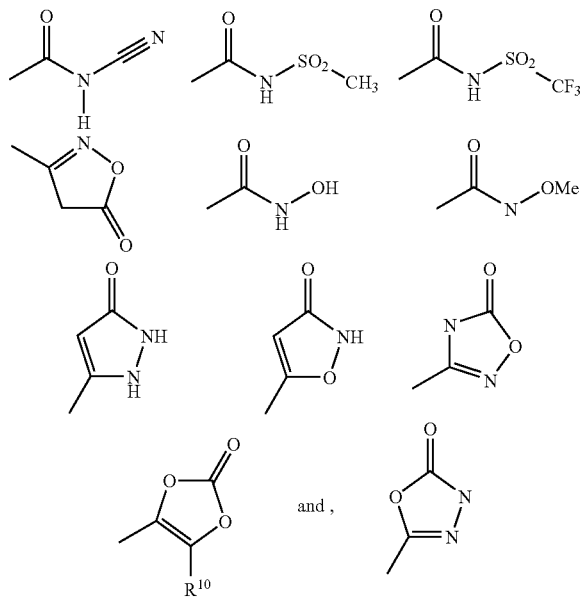

wherein Me is methyl; and

R15 and R16 are independently of one another hydrogen, —($C_1$–$C_6$)-alkyl, or together form a ring selected from the group consisting of cyclopropyl, cyclobutyl, cyclopentyl or cyclohexyl, that is unsubstituted or substituted one to three times by $R^{10}$.

6. The compound according to claim 1, wherein, $R^0$ is pyridyl, 2-pyridyl, 3-pyridyl, 4-pyridyl, pyrrolyl, 2-pyrrolyl, 3-pyrrolyl, furyl, 2-furyl, 3-furyl; thienyl, 2-thienyl, 3-thienyl, imidazolyl, pyrazolyl, oxazolyl, isoxazolyl, thiazolyl, thiadiazolyl, isothiazolyl, triazolyl, tetrazolyl, pyridazinyl or pyrazinyl, that is unsubstituted, mono-, di- or trisubstituted independently of one another by R8, and additionally is substituted by a residue selected from the group consisting of pyridyl, 2-pyridyl, 3-pyridyl, 4-pyridyl, pyrrolyl, 2-pyrrolyl, 3-pyrrolyl, furyl, 2-furyl, 3-furyl; thienyl, 2-thienyl, 3-thienyl, imidazolyl, pyrazolyl, oxazolyl, isoxazolyl, thiazolyl, thiadiazolyl, isothiazolyl, triazolyl, tetrazolyl, pyridazinyl and pyrazinyl, that is unsubstituted, mono-, di- or trisubstituted independently of one another by R8;

R8 is
  1) F, Cl, Br, or I,
     —C(O)—$NH_2$,
  3) —($C_1$–$C_4$)-alkyl, that is unsubstituted, mono-, di- or trisubstituted independently of one another by halogen, —OH or a methoxy residue, or
  4) —O—($C_1$–$C_4$)-alkyl, that is unsubstituted, mono-, di- or trisubstituted independently of one another by halogen or a methoxy residue;

Q is a direct bond or —($C_1$–$C_6$)-alkylene;
$R^1$ is hydrogen or —($C_1$–$C_2$)-alkyl;
$R^2$ is a direct bond or —($C_1$–$C_2$)-alkylene; or
$R^1$—N—$R^2$—V optionally forms a 4- to 7-membered cyclic group selected from the group consisting of piperidine, piperazine, pyridine, pyrimidine, pyrrolidine, pyrrolidinone, 1,2,3-triazine, 1,2,4-triazine, 1,3,5-triazine, 1,2,3-triazole, 1,2,4-triazole, tetrazine, tetrazole, 1,2-diazepin, 1,3-diazepine, 1,4-diazepine, azepine, ketopiperazine, oxazole, isoxazole, isoxazolidine, 2-isoxazoline, morpholine, thiazole, isothiazole, thiadiazole and thiomorpholine, thatis unsubstituted, mono-, di- or trisubstituted independently of one another by R14;

R14 is fluoro or chlorine, —($C_1$–$C_4$)-alkyl or —$NH_2$;

V is
  1) azaindolyl, 1H-pyrrolopyridyl, azetidine, azepine, aziridine, azirine, 1,4-diazepane, 1,2-diazepine, 1,3-diazepine, 1,4-diazepine, diazirine, 1,3-dioxolane, dioxazole, furan, imidazole, isoquinoline, isothiazole, isothiazolidine, isothiazoline, isoxazole, 2-isoxazoline, isoxazolidine, ketopiperazine, morpholine, 1,2-oxazine, 1,3-oxazine, 1,4-oxazine, oxazole, 1,2-oxathiolan, piperidine, pyran, pyrazine, pyrazole, pyridazine, piperazine, pyridine, pyridone, pyrimidine, pyrrole, pyrrolidine, pyrrolidinone, quinazoline, quinoline, tetrazine, tetrazole, thiadiazine, 1,2-thiazine, 1,3-thiazine, 1,4-thiazine, 1,3-thiazole, thietan, thiomorpholine, thiophene, thiopyran, 1,2,3-triazine, 1,2,4-triazine, 1,3,5-triazine, 1,2,3-triazole or 1,2,4-triazole, that is unsubstituted, mono-, di- or trisubstituted independently of one another by R14, or
  2) phenyl, that is unsubstituted, mono-, di- or trisubstituted independently of one another by R14;

G is a direct bond, —$(CH_2)_m$—, or —$(CH_2)_m$—$NR^{10}$—;
m is the integer zero, 1, 2, 3 or 4;
M is
  1) hydrogen,
  2) —($C_1$–$C_6$)-alkyl, wherein alkyl is unsubstituted or mono-, di- or trisubstituted independently of one another by R14,
  3) heterocyclyl, that is a residue selected from the group consisting of 1,4-diazepane, ketomorpholine, thiophene, pyridazone, piperidine, piperazine, pyridine, pyrimidine, pyrrolidine, pyrrolidinone, pyridonyl, imidazole, pyridazine, pyrazine, 1,2,3-triazine, 1,2,4-triazine, 1,3,5-triazine, 1,2,3-triazole, 1,2,4-triazole, tetrazine, tetrazole, 1,2-diazepine, 1,3-diazepine, 1,4-diazepine, azepine, ketopiperazine, oxazole, isoxazole, isoxazolidine, 2-isoxazoline, morpholine, thiazole, isothiazole, tetrahydropyran, 1,4,5,6-tetrahydro-pyridazinyl, thiadiazole and thiomorpholine, that is unsubstituted, mono-, di- or trisubstituted independently of one another by R14, or
  4) —($C_3$–$C_6$)-cycloalkyl;

$R^3$ is
  1) hydrogen,
  2) halogen,
  3) —($C_1$–$C_4$)-alkyl, that is unsubstituted, mono-, di- or trisubstituted independently of one another by R13,
  4) —($C_1$–$C_3$)-perfluoroalkyl,
  5) phenyl, that is unsubstituted, mono-, di- or trisubstituted independently of one another by R13,
  6) —($C_0$–$C_4$)-alkylene-O—R19, wherein R19 is
     a) hydrogen,
     b) —($C_1$–$C_4$)-alkyl, that is unsubstituted, mono-, di- or trisubstituted independently of one another by R13,
     c) phenyl, that is unsubstituted, mono-, di- or trisubstituted independently of one another by R13,
     d) —$CF_3$ or
     e) —$CHF_2$,
  7) —CN, 8) —SO$_s$—R$^{11}$, wherein s is 1 or 2,
9) —SO$_t$—N(R$^{11}$)—R$^{12}$, wherein t is 1 or 2,
10) —(C$_0$–C$_4$)-alkylene-C(O)—R$^{11}$,
11) —(C$_0$–C$_4$)-alkylene-C(O)—O—R$^{11}$,
12) —(C$_0$–C$_4$)-alkylene-C(O)—N(R$^{11}$)—R$^{12}$,
13) —(C$_0$–C$_4$)-alkylene-N(R$^{11}$)—R$^{12}$,
14) —NR$^{10}$—SO$_2$—R$^{10}$,
15) —(C$_0$–C$_2$)alkylene-C(O)—O—(C$_2$–C$_4$)-alkylene-O—C(O)—(C$_1$–C$_4$)-alkyl,
16) —C(O)—O—C(R15, R16)—O—C(O)—R17,
17) —(C$_0$–C$_2$)alkylene-C(O)—O—(C$_2$–C$_4$)-alkylene-O—C(O)—O—(C$_1$–C$_6$)-alkyl,
18) —C(O)—O—C(R15, R16)—O—C(O)—O—R17,
19) —(C$_0$–C$_4$)-alkylene-(C$_4$–C$_{15}$)-heterocyclyl, wherein heterocyclyl is a residue selected from the group consisting of pyridine, furan, thiazole or thiophene and is unsubstituted, mono-, di- or trisubstituted independently of one another by R13,
20) —(C$_0$–C$_3$)-alkylene-(C$_3$–C$_6$)-cycloalkyl, wherein cycloalkyl is unsubstituted, mono-, di- or trisubstituted independently of one another by R13,
21) —(C$_0$–C$_3$)-alkylene-O—CH$_2$—CF$_2$—CH$_2$—O—(C$_0$–C$_3$)-alkyl, —(C$_0$–C$_3$)-alkylene-O—CH$_2$—CF$_2$—CF$_2$—CH$_2$—O—(C$_0$–C$_3$)-alkyl, or —(C$_0$–C$_3$)-alkylene-O—CH$_2$—(C$_1$–C$_3$)-perfluoroalkylene-CH$_2$—OH,
22) —SO$_w$—N(R$^{11}$)—R$^{13}$, wherein w is 1 or 2,
23) —(C$_0$–C$_4$)-alkylene-C(O)—N(R$^{11}$)—R$^{13}$,
24) —(C$_0$–C$_4$)-alkylene-N(R$^{11}$)—R$^{13}$, or
25) a residue from the following list

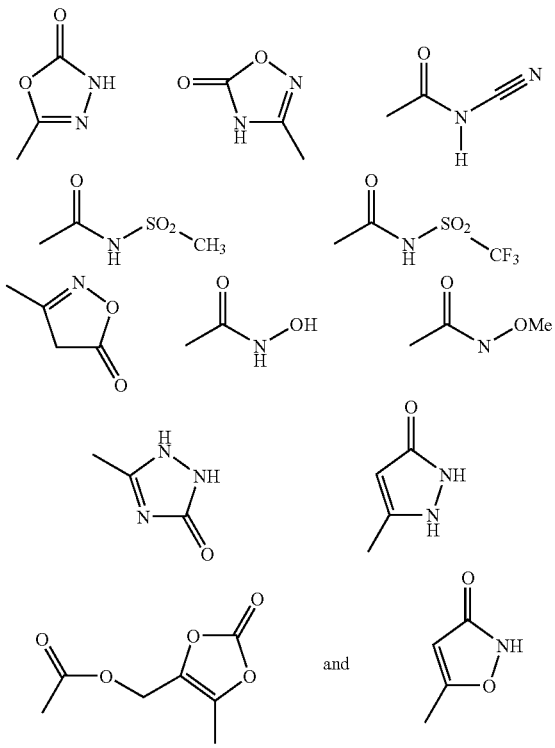

wherein Me is methyl, provided that R$^3$ is optionally attached at any position on the ring of formula II;

R11 and R12 are independently of one another identical or different and are
1) hydrogen,
2) —(C$_1$–C$_4$)-alkyl, that is unsubstituted, mono-, di- or trisubstituted independently of one another by R13,
3) —(C$_0$–C$_6$)-alkyl-(C$_3$–C$_6$)-cycloalkyl,
5) —(C$_0$–C$_6$)-alkyl-(C$_4$–C$_{15}$)-heterocyclyl, wherein alkyl and heterocyclyl independently from one another are unsubstituted, mono-, di- or trisubstituted by R13 and wherein heterocyclyl is selected from the group consisting of azetidine, cyclopropyl, cyclobutyl, 4,5-dihydro-oxazol, imidazolidine, morpholine, (1,4)-oxazepane, oxazolidine, piperidine, piperazine, pyrrolidine, tetrahydrothiophene, thiazolidine and thiomorpholine, or
7) —O—R$^{17}$;
R11 and R12 together with the nitrogen to which they are bonded form a heterocyclic ring, that is selected from the group consisting of azetidine, cyclopropyl, cyclobutyl, 4,5-dihydro-oxazole, imidazolidine, morpholine, (1,4)-oxazepane, oxazolidine, piperidine, piperazine, pyrrolidine, tetrahydrothiophene, thiazolidine and thiomorpholine, that is unsubstituted, mono-, di- or trisubstituted independently of one another by R13;
R13 is fluorine, —CN, =O, —OH, —CF$_3$, —C(O)—O—R$^{10}$, —C(O)—N(R$^{10}$)—R$^{20}$, —N(R$^{10}$)—R$^{20}$, —(C$_3$–C$_6$)-cycloalkyl, —(C$_0$–C$_3$)-alkylene-O—R$^{10}$, —Si—(CH$_3$)$_3$, —S—R$^{10}$, —SO$_2$—R$^{10}$, —S(O)$_2$—N(R$^{10}$)—R$^{20}$, —(C$_1$–C$_3$)-perfluoroalkyl, or a residue from the following list

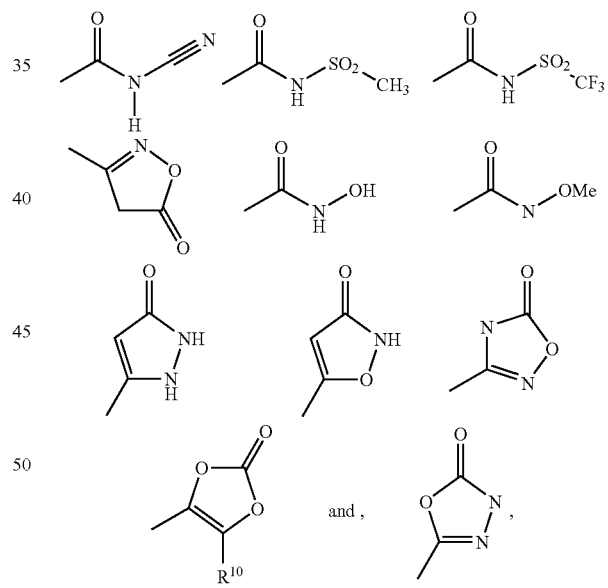

wherein Me is methyl;
R$^{10}$ and R$^{20}$ are independently of one another hydrogen, —(C$_1$–C$_4$)-alkyl or —(C$_1$–C$_3$)-perfluoroalkyl; and
R$^{15}$ and R$^{16}$ are independently of one another hydrogen, —(C$_1$–C$_4$)-alkyl, or together form a ring selected from the group consisting of cyclopropyl, cyclobutyl, cyclopentyl or cyclohexyl, wherein each ring is unsubstituted or substituted one to three times by R$^{10}$.
7. The compound according to claim 1, wherein,
R0 is thienyl, thiadiazolyl, isoxazolyl or thiazolyl, that is substituted by a residue selected from the group consisting of thienyl, 2-thienyl and 3-thienyl, that is unsubstituted, mono- or disubstituted independently of one another by R8;
R8 is F, Cl, or Br, —OCH$_3$, —C(O)—NH$_2$ or —O—CF$_3$;
Q is a direct bond, methylene or ethylene;
R$^1$ is hydrogen;
R$^2$ is a direct bond or methylene;
R$^1$—N—R$^2$—V optionally forms a 4- to 8-membered cyclic group selected from the group consisting of azetidine, pyrrolidine, piperidine or piperazine;
R14 is fluorine or chlorine, methyl, ethyl or —NH$_2$;
V is
1) azaindolyl, 1H-pyrrolopyridyl, azetidine, 1,4-diazepane, isoxazole, isoquinoline, piperazine, piperidine, pyrazine, pyridazine, pyrimidine, pyrrolidine, quinazoline, quinoline or tetrahydropyrane, that is unsubstituted, mono- or disubstituted independently of one another by R14, or
2) phenyl, that is unsubstituted, mono- or disubstituted independently of one another by R14;
G is a direct bond, —(CH$_2$)$_m$—, or —(CH$_2$)$_m$—NR$^{10}$—;
m is the integer zero, 1 or 2;
M is hydrogen, —(C$_2$–C$_4$)-alkyl, azepanyl, cyclopropyl, cyclobutyl, cyclopentyl, cyclohexyl, imidazolyl, ketomorpholinyl, morpholinyl, [1,4]oxazepanyl, piperidinyl, piperidenyl, pyrazinyl, pyrazolyl, pyridazinyl, pyridyl, pyrimidyl, pyrrolidinyl, 1,4,5,6-tetrahydro-pyridazinyl, or tetrahydropyranyl, that is unsubstituted, mono- or disubstituted independently of one another by R14;
R$^3$ is
1) hydrogen,
2) halogen,
3) —(C$_1$–C$_4$)-alkyl, that is unsubstituted, mono-, di- or trisubstituted independently of one another by R13,
4) —(C$_1$–C$_3$)-perfluoroalkyl,
5) phenyl, that is unsubstituted, mono-, di- or trisubstituted independently of one another by R13,
6) —(C$_0$–C$_4$)-alkylene-O—R19, wherein R19 is
   a) hydrogen,
   b) —(C$_1$–C$_4$)-alkyl, that is unsubstituted, mono-, di- or trisubstituted independently of one another by R13,
   c) phenyl, that is unsubstituted, mono-, di- or trisubstituted independently of one another by R13,
   d) —CF$_3$ or
   d) —CHF$_2$,
7) —CN,
8) —SO$_s$—R$^{11}$, wherein s is 1 or 2,
9) —SO$_t$—N(R$^{11}$)—R$^{12}$, wherein t is 1 or 2,
10) —(C$_0$–C$_4$)-alkylene-C(O)—R$^{11}$,
11) —(C$_0$–C$_4$)-alkylene-C(O)—O—R$^{11}$,
12) —(C$_0$–C$_4$)-alkylene-C(O)—N(R$^{11}$)—R$^{12}$,
13) —(C$_0$–C$_4$)-alkylene-N(R$^{11}$)—R$^{12}$,
14) —NR$^{10}$—SO$_2$—R$^{10}$,
15) —(C$_0$–C$_2$)alkylene-C(O)—O—(C$_2$–C$_4$)-alkylene-O—C(O)-(C$_1$–C$_4$)-alkyl,
16) —C(O)—O—C(R15, R16)—O—C(O)—R17,
17) —(C$_0$–C$_2$)alkylene-C(O)—O—(C$_2$–C$_4$)-alkylene-O—C(O)—O—(C$_1$–C$_6$)-alkyl,
18) —C(O)—O—C(R15, R16)—O—C(O)—O—R17,
19) —(C$_0$–C$_4$)-alkylene-(C$_4$–C$_{15}$)-heterocyclyl, wherein heterocyclyl is selected from the group consisting of pyrrolyl, pyridyl, furanyl and thienyl that is unsubstituted, mono-, di- or trisubstituted by R13;
20) —(C$_0$–C$_3$)-alkylene-(C$_3$–C$_6$)-cycloalkyl is unsubstituted or mono-, di- or trisubstituted independently of one another by R13,
21) a residue from the following list

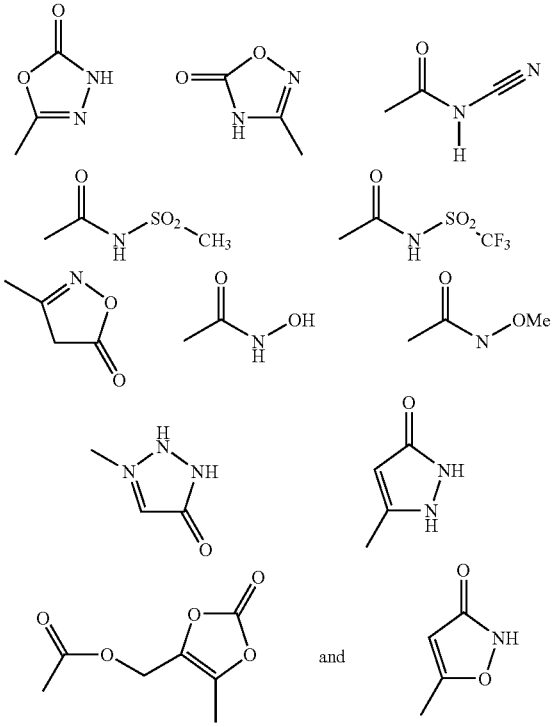

wherein Me is methyl,
provided that R$^3$ is optionally attached at any position on the ring of formulae I or II;
R11 and R12 are independently of one another identical or different and are
1) hydrogen,
2) —(C$_1$–C$_4$)-alkyl, that is unsubstituted, mono-, di- or trisubstituted independently of one another by R13,
3) —(C$_0$–C$_6$)-alkyl-(C$_3$–C$_6$)-cycloalkyl,
8) —(C$_0$–C$_6$)—(C$_4$–C$_{15}$)-heterocyclyl, wherein alkyl and heterocyclyl independently from one another are unsubstituted, mono-, di- or trisubstituted by R13 and wherein heterocyclyl is selected from the group consisting of azetidinyl, 4,5-dihydro-oxazolinyl, imidazolidinyl, morpholinyl, (1,4)-oxazepanyl, pyrrolidinyl and tetrahydrothiophenyl or
7) —O—R$^{17}$;
R11 and R12 together with the nitrogen to which they are bonded optionally form a ring, that is selected from the group consisting of azetidine, imidazolidine, morpholine, (1,4)-oxazepane, oxazolidine, piperazine, piperidine, pyrrolidine, tetrahydrothiazol, thiazolidine and thiomorpholine, that is unsubstituted, mono- or disubstituted independently of one another by R13;
R13 is fluorine or chlorine, —CN, =O, —OH, —CF$_3$, —C(O)—O—R$^{10}$, —C(O)—N(R$^{10}$)—R$^{20}$, —N(R$^{10}$)—R$^{20}$, —(C$_3$–C$_6$)-cycloalkyl, —(C$_0$–C$_3$)-alkylene-O—R$^{10}$, —Si—(CH$_3$)$_3$, —S—R$^{10}$, —SO$_2$—R$^{10}$, —(C$_1$–C$_4$)-alkyl, —(C$_1$–C$_3$)-perfluoroalkyl, —S(O)$_2$—N(R$^{10}$)—R$^{20}$, or a residue from the following list

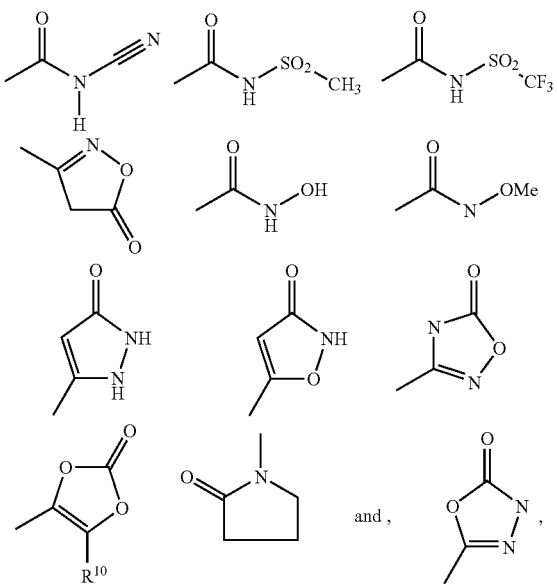

wherein Me is methyl;
$R^{10}$ and $R^{20}$ are independently of one another hydrogen, —$(C_1$–$C_4)$-alkyl or —$(C_1$–$C_3)$-perfluoroalkyl; and $R^{15}$ and $R^{16}$ are independently of one another hydrogen, —$(C_1$–$C_4)$-alkyl, or together form a ring selected from the group consisting of cyclopropyl, cyclobutyl, cyclopentyl or cyclohexyl, that is unsubstituted or substituted one to three times by $R^{10}$.

8. The compound according to claim 1, which is:
1-[5-(5-Chloro-thiophen-2-yl)-isoxazol-3-ylmethyl]-5-pyrrol-1-yl-1H-[1,2,4]triazole-3-carboxylic acid (1-isopropyl-piperidin-4-yl)-amide;

1-[5-(5-Chloro-thiophen-2-yl)-isoxazol-3-ylmethyl]-5-pyridin-2-yl-1H-[1,2,4]triazole-3-carboxylic acid (1-isopropyl-piperidin-4-yl)-amide;

2-[5-(5-Chloro-thiophen-2-yl)-isoxazol-3-ylmethyl]-5-pyridin-2-yl-2H-[1,2,4]triazole-3-carboxylic acid (1-isopropyl-piperidin-4-yl)-amide; or 1-[5-(5-Chloro-thiophen-2-yl)-isoxazol-3-ylmethyl]-5-phenyl-1H-[1,2,4]triazole-3-carboxylic acid (1-isopropyl-piperidin-4-yl)-amide.

9. A pharmaceutical preparation, comprising at least one compound of the formulae II or IIb according to claim 1, or a stereoisomeric form thereof, or a mixture of the stereoisomeric forms thereof in any ratio, or a physiologically tolerable salt thereof, and a pharmaceutically acceptable carrier.

* * * * *